United States Patent
Gotoh et al.

(10) Patent No.: US 9,790,428 B2
(45) Date of Patent: Oct. 17, 2017

(54) PIPERIDINE DERIVATIVE, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Yasuyuki Gotoh, Tokyo (JP); Takahiro Kobayashi, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 15/364,475

(22) Filed: Nov. 30, 2016

(65) Prior Publication Data

US 2017/0158961 A1 Jun. 8, 2017

(30) Foreign Application Priority Data

Dec. 3, 2015 (JP) .................................. 2015-236621

(51) Int. Cl.
| | | |
|---|---|---|
| *G02F 1/1333* | (2006.01) | |
| *C09K 19/54* | (2006.01) | |
| *C07D 211/42* | (2006.01) | |
| *C07D 211/94* | (2006.01) | |
| *C09K 19/30* | (2006.01) | |
| *C09K 19/34* | (2006.01) | |
| *G02F 1/1337* | (2006.01) | |

(52) U.S. Cl.
CPC ............ *C09K 19/54* (2013.01); *C07D 211/42* (2013.01); *C07D 211/94* (2013.01); *C09K 19/3001* (2013.01); *C09K 19/3003* (2013.01); *C09K 19/3068* (2013.01); *C09K 19/3402* (2013.01); *G02F 1/133365* (2013.01); *C09K 2019/301* (2013.01); *C09K 2019/3004* (2013.01); *C09K 2019/308* (2013.01); *C09K 2019/3009* (2013.01); *C09K 2019/3016* (2013.01); *C09K 2019/3077* (2013.01); *C09K 2019/3083* (2013.01); *C09K 2019/3422* (2013.01); *G02F 1/133723* (2013.01); *G02F 2001/133302* (2013.01); *G02F 2202/022* (2013.01)

(58) Field of Classification Search
CPC ................ C09K 19/54; C09K 19/3001; C09K 19/3003; C09K 19/3068; C09K 19/3402; C09K 2019/3004; C09K 2019/3009; C09K 2019/301; C09K 2019/3016; C09K 2019/3077; C09K 2019/308; C09K 2019/3083; C09K 2019/3422; G02F 1/1333; G02F 1/133723; G02F 1/133365; G02F 2001/133302; G02F 2202/022; C07D 211/42; C07D 211/94
USPC ......................... 252/299.01, 299.61; 428/1.1
See application file for complete search history.

(56) References Cited

U.S. PATENT DOCUMENTS

| | | |
|---|---|---|
| 2004/0085490 A1 | 5/2004 | Li et al. |
| 2016/0131947 A1 * | 5/2016 | Park et al. ........ G02F 1/133711 349/128 |

FOREIGN PATENT DOCUMENTS

| | | | | |
|---|---|---|---|---|
| DE | 10 2011 013 007 A1 * | 10/2011 | ............. | C09K 19/54 |
| DE | 10 2013 017 174 A1 * | 4/2014 | ............. | C09K 19/52 |

* cited by examiner

*Primary Examiner* — Geraldina Visconti

(74) *Attorney, Agent, or Firm* — Wenderoth, Lind & Ponack, L.L.P.

(57) ABSTRACT

Provided is a compound having an effect on preventing photolysis of a liquid crystal composition and having a high solubility in the liquid crystal composition, a liquid crystal composition containing the compound and a liquid crystal display device including the composition. The compound is represented by formula (1), the liquid crystal composition contains the compound, and the liquid crystal display device uses the composition:

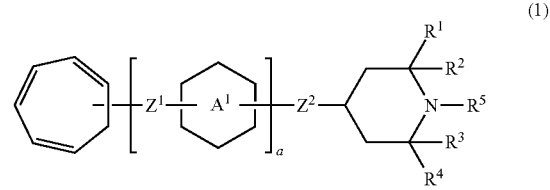

(1)

wherein in formula (1), $R^1$, $R^2$, $R^3$ and $R^4$ are independently hydrogen or alkyl having 1 to 4 carbons; $R^5$ is hydrogen, hydroxy, oxy radical, alkyl having 1 to 10 carbons or alkoxy having 1 to 10 carbons; ring $A^1$ is 1,4-cyclohexylene, 1,4-cyclohexenylene or the like; $Z^1$ and $Z^2$ are independently a single bond or alkylene having 1 to 10 carbons; and a is 0, 1, 2 or 3.

17 Claims, No Drawings

PIPERIDINE DERIVATIVE, LIQUID CRYSTAL COMPOSITION AND LIQUID CRYSTAL DISPLAY DEVICE

TECHNICAL FIELD

The invention relates to a piperidine derivative, a liquid crystal composition and a liquid crystal display device. In particular, the invention relates to cycloheptatriene having a substituent such as piperidinyl, a liquid crystal composition containing the compound and having a positive or negative dielectric anisotropy and a liquid crystal display device including the composition.

BACKGROUND ART

In a liquid crystal display device, a classification based on an operating mode for liquid crystal molecules includes a phase change (PC) mode, a twisted nematic (TN) mode, a super twisted nematic (STN) mode, an electrically controlled birefringence (ECB) mode, an optically compensated bend (OCB) mode, an in-plane switching (IPS) mode, a vertical alignment (VA) mode, a fringe field switching (FFS) mode and a field-induced photo-reactive alignment (FPA) mode. A classification based on a driving mode in the device includes a passive matrix (PM) and an active matrix (AM). The PM is classified into static, multiplex and so forth. The AM is classified into a thin film transistor (TFT), a metal insulator metal (MIM) and so forth. The TFT is classified into amorphous silicon and polycrystal silicon. The latter is classified into a high temperature type and a low temperature type according to a production process. A classification based on a light source includes a reflective type utilizing natural light, a transmissive type utilizing backlight and a transflective type utilizing both the natural light and the backlight.

The liquid crystal display device includes a liquid crystal composition having a nematic phase. The composition has suitable characteristics. An AM device having good characteristics can be obtained by improving characteristics of the composition. Table 1 below summarizes a relationship in two characteristics. The characteristics of the composition will be further described based on a commercially available AM device. A temperature range of the nematic phase relates to a temperature range in which the device can be used. A preferred maximum temperature of the nematic phase is about 70° C. or higher, and a preferred minimum temperature of the nematic phase is about −10° C. or lower. Viscosity of the composition relates to a response time of the device. A short response time is preferred for displaying moving images on the device. A shorter response time even by one millisecond is desirable. Accordingly, a small viscosity of the composition is preferred. A small viscosity at a low temperature is further preferred.

TABLE 1

Characteristics of Composition and AM Device

| No. | Characteristics of Composition | Characteristics of AM Device |
|---|---|---|
| 1 | Wide temperature range of a nematic phase | Wide usable temperature range |
| 2 | Small viscosity[1] | Short response time |
| 3 | Suitable optical anisotropy | Large contrast ratio |
| 4 | Large positive or negative dielectric anisotropy | Low threshold voltage, small electric power consumption and large contrast ratio |
| 5 | Large specific resistance | Large voltage holding ratio and large contrast ratio |
| 6 | High stability to ultraviolet light and heat | Long service life |
| 7 | Large elastic constant | Large contrast ratio and short response time |

[1]Time for injecting a composition into a liquid crystal device can be shortened.

An optical anisotropy of the composition relates to a contrast ratio in the device. According to a mode of the device, a large optical anisotropy or a small optical anisotropy, more specifically, a suitable optical anisotropy is required. A product ($\Delta n \times d$) of the optical anisotropy ($\Delta n$) of the composition and a cell gap (d) in the device is designed so as to maximize the contrast ratio. A suitable value of the product depends on a type of the operating mode. A composition having the large optical anisotropy is preferred for a device having a small cell gap. A large dielectric anisotropy in the composition contributes to a low threshold voltage, a small electric power consumption and a large contrast ratio in the device. Accordingly, the large positive or negative dielectric anisotropy is preferred. A large specific resistance in the composition contributes to a large voltage holding ratio and the large contrast ratio in the device. Accordingly, a composition having the large specific resistance at room temperature and also at a high temperature in an initial stage is preferred. A composition having the large specific resistance at room temperature and also at a high temperature after the device has been used for a long period of time is preferred. Stability of the composition to ultraviolet light and heat relates to a service life of the device. When the stability is high, the device has a long service life. Such characteristics are preferred for an AM device used in a liquid crystal projector, a liquid crystal television and so forth.

In a liquid crystal display device having a polymer sustained alignment (PSA) mode, a liquid crystal composition containing a polymer is used. First, a composition to which a small amount of a polymerizable compound is added is injected into the device. Then, the composition is irradiated with ultraviolet light while voltage is applied between substrates of the device. The polymerizable compound is polymerized to form a network structure of the polymer in the liquid crystal composition. In the composition, alignment of liquid crystal molecules can be controlled by the polymer, and therefore a response time of the device is shortened and also image persistence is improved. Such an effect of the polymer can be expected for a device having the mode such as the TN mode, the ECB mode, the OCB mode, the IPS mode, the VA mode, the FFS mode and the FPA mode.

The liquid crystal composition is prepared by mixing a liquid crystal compound. An additive such as a polymerizable compound, a polymerization initiator, a polymerization inhibitor, an optically active compound, an antioxidant, an ultraviolet light absorber, a light stabilizer, a heat stabilizer, and an antifoaming agent is added when necessary. Among the additives, the light stabilizer is effective in preventing the liquid crystal compound from being decomposed by backlight, or light from the sun. The high voltage holding ratio of the device is maintained by the effect, and therefore the service life of the device is increased. Although a hindered amine light stabilizer (HALS; hindered amine light stabilizer) is suitable for such a purpose, a more superior light stabilizer is expected to be developed.

CITATION LIST

Patent Literature

Patent literature No. 1: JP 2004-507607 A.

SUMMARY OF INVENTION

Technical Problem

A first objective of the invention is to provide a compound having an effect on preventing photolysis of a liquid crystal composition, and having a high solubility in the liquid crystal composition. A second objective is to provide a liquid crystal composition containing the compound, and satisfying at least one of characteristics including a high maximum temperature of a nematic phase, a low minimum temperature of the nematic phase, a small viscosity, a suitable optical anisotropy, a large positive or negative dielectric anisotropy, a large specific resistance, a high stability to ultraviolet light, a high stability to heat and a large elastic constant. The objective is also to provide a liquid crystal composition having stability to light. A third objective is to provide a liquid crystal display device including the composition, and having a wide temperature range in which the device can be used, a short response time, a high voltage holding ratio, a low threshold voltage, a large contrast ratio, a small flicker rate and a long service life.

Solution to Problem

The invention concerns a compound represented by formula (1), a liquid crystal composition containing the compound and a liquid crystal display device including the composition:

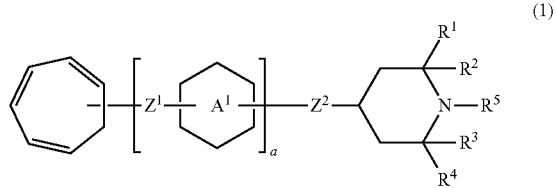

(1)

wherein, in formula (1), $R^1$, $R^2$, $R^3$ and $R^4$ are independently hydrogen or alkyl having 1 to 4 carbons, and $R^5$ is hydrogen, hydroxy, oxy radical, alkyl having 1 to 10 carbons or alkoxy having 1 to 10 carbons;

ring $A^1$ is 1,4-cyclohexylene, 1,4-cyclohexenylene, 3,4-dihydro-2H-pyrane-2,5-diyl, 3,4-dihydro-2H-pyrane-3,6-diyl, 3,6-dihydro-2H-pyrane-2,5-diyl, tetrahydropyran-2,5-diyl, 1,3-dioxane-2,5-diyl, 1,2-phenylene, 1,3-phenylene, 1,4-phenylene, pyridine-2,5-diyl, pyrimidine-2,5-diyl, decahydronaphthalene-2,6-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl or naphthalene-2,7-diyl, and in the rings, at least one piece of hydrogen may be replaced by fluorine, chlorine, alkyl having 1 to 5 carbons, alkoxy having 1 to 5 carbons, or alkyl having 1 to 5 carbons in which at least one piece of hydrogen is replaced by fluorine or chlorine, and one piece of hydrogen may be replaced by a monovalent group represented by formula (P-1);

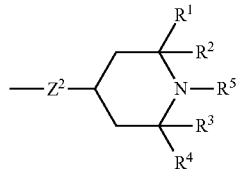

(P-1)

wherein, in formula (P-1), $R^1$, $R^2$, $R^3$ and $R^4$ are independently hydrogen or alkyl having 1 to 4 carbons, and $R^5$ is hydrogen, hydroxy, oxy radical, alkyl having 1 to 10 carbons or alkoxy having 1 to 10 carbons;

$Z^2$ is a single bond or alkylene having 1 to 10 carbons, and in the alkylene, at least one piece of —$CH_2$— may be replaced by —O—, —S—, —CO—, —COO— or —OCO—, and at least one piece of —$CH_2$—$CH_2$— may be replaced by —CH=CH— or —C≡C—, and in the groups, at least one piece of hydrogen may be replaced by fluorine or chlorine; and in formula (1), $Z^1$ and $Z^2$ are independently a single bond or alkylene having 1 to 10 carbons, and in the alkylene, at least one piece of —$CH_2$— may be replaced by —O—, —S—, —CO—, —COO— or —OCO—, and at least one piece of —$CH_2$—$CH_2$— may be replaced by —CH=CH— or —C≡C—, and in the groups, at least one piece of hydrogen may be replaced by fluorine or chlorine; and a is 0, 1, 2 or 3.

Advantageous Effects of Invention

A first advantage of the invention is to provide a compound having an effect on preventing photolysis of a liquid crystal composition, and having a high solubility in the liquid crystal composition. A second advantage is to provide a liquid crystal composition containing the compound, and satisfying at least one of characteristics including a high maximum temperature of a nematic phase, a low minimum temperature of the nematic phase, a small viscosity, a suitable optical anisotropy, a large positive or negative dielectric anisotropy, a large specific resistance, a high stability to ultraviolet light, a high stability to heat and a large elastic constant. The advantage is also to provide a liquid crystal composition having stability to light. A third advantage is to provide a liquid crystal display device including the composition, and having a wide temperature range in which the device can be used, a short response time, a high voltage holding ratio, a low threshold voltage, a large contrast ratio, a small flicker rate and a long service life.

DESCRIPTION OF EMBODIMENTS

Usage of terms herein is as described below. Terms "liquid crystal compound," "liquid crystal composition" and "liquid crystal display device" may be occasionally abbreviated as "compound," "composition" and "device," respectively. "Liquid crystal compound" is a generic term for a compound having a liquid crystal phase such as a nematic phase and a smectic phase, and a compound having no liquid crystal phase but to be mixed with a composition for the purpose of adjusting physical properties of the composition such as a maximum temperature, a minimum temperature, viscosity and dielectric anisotropy. The compound has a six-membered ring such as 1,4-cyclohexylene and 1,4-phenylene, and has rod-like molecular structure. "Liquid crystal display device" is a generic term for a liquid crystal display panel and a liquid crystal display module. "Polymerizable compound" is a compound to be added for the purpose of forming a polymer in the composition.

The liquid crystal composition is prepared by mixing a plurality of liquid crystal compounds. To the liquid crystal composition, an additive is added for the purpose of further adjusting physical properties. The additive such as the polymerizable compound, a polymerization initiator, a polymerization inhibitor, an optically active compound, an antioxidant, an ultraviolet light absorber, a light stabilizer, a heat stabilizer, a dye, and an antifoaming agent is added when necessary. The liquid crystal compound and the additive are mixed in such a procedure. A proportion (content) of the liquid crystal compounds is expressed in terms of weight percent (% by weight) based on the weight of the liquid crystal composition containing no additive, even after the additive has been added. A proportion (amount of addition) of the additive is expressed in terms of weight percent (% by weight) based on the weight of the liquid crystal composition containing no additive. Weight parts per million (ppm) may be occasionally used. A proportion of the polymerization initiator and the polymerization inhibitor is exceptionally expressed based on the weight of the polymerizable compound.

"Clearing point" is a transition temperature between a liquid crystal phase and an isotropic phase in the liquid crystal compound. "Minimum temperature of the liquid crystal phase" is a transition temperature between a solid and the liquid crystal phase (such as the smectic phase and the nematic phase) in the liquid crystal compound. "Maximum temperature of the nematic phase" is a transition temperature between the nematic phase and the isotropic phase in a mixture of the liquid crystal compound and a base liquid crystal, or in the liquid crystal composition, and may be occasionally abbreviated as "maximum temperature." "Minimum temperature of the nematic phase" may be occasionally abbreviated as "minimum temperature." An expression "increase the dielectric anisotropy" means that a value of dielectric anisotropy positively increases in a liquid crystal composition having a positive dielectric anisotropy, and the value of dielectric anisotropy negatively increases in a liquid crystal composition having a negative dielectric anisotropy. An expression "having a large voltage holding ratio" means that the composition has a large voltage holding ratio at room temperature and also at a temperature close to the maximum temperature in an initial stage, and the composition has the large voltage holding ratio at room temperature and also at a temperature close to the maximum temperature even after the device has been used for a long period of time. In the composition or the device, the characteristics may be occasionally examined before and after an aging test (including an acceleration deterioration test).

A compound represented by formula (1) may be occasionally abbreviated as "compound (1)." At least one compound selected from the group of compounds represented by formula (1) may be occasionally abbreviated as "compound (1)." "Compound (1)" means one compound, a mixture of two compounds or a mixture of three or more compounds represented by formula (1). A same rule applies also to any other compound represented by any other formula. In formulas (1) to (15), symbols such as $A^1$, $B^1$ and $C^1$ surrounded by a hexagonal shape correspond to rings such as ring $A^1$, ring $B^1$ and ring $C^1$, respectively. The hexagonal shape represents a six-membered ring such as cyclohexane or benzene. The hexagonal shape may occasionally represent a condensed ring such as naphthalene or a bridged ring such as adamantane.

In formulas of component compounds, a symbol of a terminal group $R^{11}$ is used for a plurality of compounds. In the compounds, two groups represented by two of arbitrary $R^{11}$ may be identical or different. For example, in one case, $R^{11}$ of compound (2) is ethyl and $R^{11}$ of compound (3) is ethyl. In another case, $R^{11}$ of compound (2) is ethyl and $R^{11}$ of compound (3) is propyl. A same rule applies also to symbols such as $R^{12}$, $R^{13}$ and $Z^{11}$. In compound (8), when i is 2, two of rings $D^1$ exist. In the compound, two groups represented by two of rings $D^1$ may be identical or different. A same rule applies also to two of arbitrary rings $D^1$ when i is larger than 2. A same rule applies also to any other symbols.

An expression "at least one piece of 'A'" means that the number of 'A' is arbitrary. An expression "at least one piece of 'A' may be replaced by 'B'" means that, when the number of 'A' is 1, a position of 'A' is arbitrary, and also when the number of 'A' is 2 or more, positions thereof can be selected without limitation. A same rule applies also to an expression "at least one piece of 'A' is replaced by 'B'." An expression "at least one piece of 'A' may be replaced by 'B', 'C' or 'D'" includes a case where arbitrary 'A' is replaced by 'B', a case where arbitrary 'A' is replaced by 'C', and a case where arbitrary 'A' is replaced by 'D', and also a case where a plurality of pieces of 'A' are replaced by at least two pieces of 'B', 'C' and/or 'D'. For example, "alkyl in which at least one piece of —$CH_2$— may be replaced by —O— or —CH=CH—" includes alkyl, alkoxy, alkoxyalkyl, alkenyl, alkoxyalkenyl and alkenyloxyalkyl. In addition, a case where replacement of two successive —$CH_2$— by —O— results in forming —O—O— is not preferred. In the alkyl or the like, a case where replacement of —$CH_2$— of a methyl part (—$CH_2$—H) by —O— results in forming —O—H is not preferred, either.

An expression "$R^{11}$ and $R^{12}$ are independently alkyl having 1 to 10 carbons or alkenyl having 2 to 10 carbons, and in the alkyl and the alkenyl, and at least one piece of —$CH_2$— may be replaced by —O—, and in the groups, at least one piece of hydrogen may be replaced by fluorine" may be occasionally used. In the expression, "in the groups" may be interpreted literally. In the expression, "the groups" means alkyl, alkenyl, alkoxy, alkenyloxy and the like. More specifically, "the groups" represents all the groups described before the term "in the groups." The commonsense interpretation applies also to the term "in the monovalent group" or the term "in the divalent group." For example, "the monovalent group" represents all the groups described before the term "in the monovalent group."

Halogen means fluorine, chlorine, bromine and iodine. Preferred halogen is fluorine and chlorine. Further preferred halogen is fluorine. Alkyl of the liquid crystal compound is straight-chain alkyl or branched-chain alkyl, but includes no cyclic alkyl. In general, straight-chain alkyl is preferred to branched-chain alkyl. A same rule applies also to a terminal group such as alkoxy and alkenyl. With regard to the configuration of 1,4-cyclohexylene, trans is preferred to cis for increasing the maximum temperature. Then, 2-fluoro-1,4-phenylene means two divalent groups described below. In a chemical formula, fluorine may be leftward (L) or rightward (R). A same rule also applies to an asymmetrical divalent group formed by removing two pieces of hydrogen from a ring, such as tetrahydropyran-2,5-diyl.

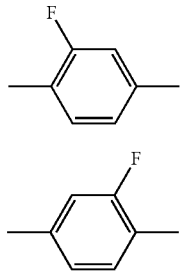

(L)

(R)

The invention includes items described below.

Item 1. A compound represented by formula (1):

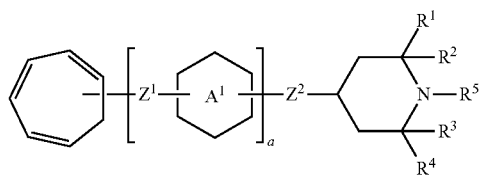

(1)

wherein, in formula (1), $R^1$, $R^2$, $R^3$ and $R^4$ are independently hydrogen or alkyl having 1 to 4 carbons, and $R^5$ is hydrogen, hydroxy, oxy radical, alkyl having 1 to 10 carbons or alkoxy having 1 to 10 carbons;

ring $A^1$ is 1,4-cyclohexylene, 1,4-cyclohexenylene, 3,4-dihydro-2H-pyrane-2,5-diyl, 3,4-dihydro-2H-pyrane-3,6-diyl, 3,6-dihydro-2H-pyrane-2,5-diyl, tetrahydropyran-2,5-diyl, 1,3-dioxane-2,5-diyl, 1,2-phenylene, 1,3-phenylene, 1,4-phenylene, pyridine-2,5-diyl, pyrimidine-2,5-diyl, decahydronaphthalene-2,6-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl or naphthalene-2,7-diyl, and in the rings, at least one piece of hydrogen may be replaced by fluorine, chlorine, alkyl having 1 to 5 carbons, alkoxy having 1 to 5 carbons, or alkyl having 1 to 5 carbons in which at least one piece of hydrogen is replaced by fluorine or chlorine, and one piece of hydrogen may be replaced by a monovalent group represented by formula (P-1);

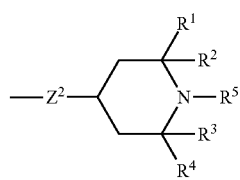

(P-1)

wherein, in formula (P-1), $R^1$, $R^2$, $R^3$ and $R^4$ are independently hydrogen or alkyl having 1 to 4 carbons, and $R^5$ is hydrogen, hydroxy, oxy radical, alkyl having 1 to 10 carbons or alkoxy having 1 to 10 carbons;

$Z^2$ is a single bond or alkylene having 1 to 10 carbons, and in the alkylene, at least one piece of —$CH_2$— may be replaced by —O—, —S—, —CO—, —COO— or —OCO—, and at least one piece of —$CH_2$—$CH_2$— may be replaced by —CH=CH— or —C≡C—, and in the groups, at least one piece of hydrogen may be replaced by fluorine or chlorine; and in formula (1), $Z^1$ and $Z^2$ are independently a single bond or alkylene having 1 to 10 carbons, and in the alkylene, at least one piece of —$CH_2$— may be replaced by —O—, —S—, —CO—, —COO— or —OCO—, and at least one piece of —$CH_2$—$CH_2$— may be replaced by —CH=CH— or —C≡C—, and in the groups, at least one piece of hydrogen may be replaced by fluorine or chlorine; and a is 0, 1, 2 or 3.

Item 2. The compound according to item 1, wherein, in formula (1), $R^1$, $R^2$, $R^3$ and $R^4$ are independently hydrogen or alkyl having 1 to 4 carbons, and $R^5$ is hydrogen, hydroxy, oxy radical, alkyl having 1 to 10 carbons or alkoxy having 1 to 10 carbons;

ring $A^1$ is 1,4-cyclohexylene, 1,4-cyclohexenylene, 3,4-dihydro-2H-pyrane-2,5-diyl, 3,4-dihydro-2H-pyrane-3,6-diyl, 3,6-dihydro-2H-pyrane-2,5-diyl, tetrahydropyran-2,5-diyl, 1,3-dioxane-2,5-diyl, 1,2-phenylene, 1,3-phenylene, 1,4-phenylene, pyridine-2,5-diyl, pyrimidine-2,5-diyl, decahydronaphthalene-2,6-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl or naphthalene-2,7-diyl, and in the rings, at least one piece of hydrogen may be replaced by fluorine, chlorine, alkyl having 1 to 5 carbons, alkoxy having 1 to 5 carbons, or alkyl having 1 to 5 carbons in which at least one piece of hydrogen is replaced by fluorine or chlorine;

$Z^1$ and $Z^2$ are independently a single bond or alkylene 1 to 10 carbons, and in the alkylene, at least one piece of —$CH_2$— may be replaced by —O—, —S—, —CO—, —COO— or —OCO—, and at least one piece of —$CH_2$—$CH_2$— may be replaced by —CH=CH— or —C≡C—, and in the groups, at least one piece of hydrogen may be replaced by fluorine or chlorine; and a is 0, 1, 2 or 3.

Item 3. The compound according to item 1, wherein, in formula (1), $R^1$, $R^2$, $R^3$ and $R^4$ are independently hydrogen or alkyl having 1 to 4 carbons, and $R^5$ is hydrogen, hydroxy, oxy radical, alkyl having 1 to 10 carbons or alkoxy having 1 to 10 carbons;

ring $A^1$ is 1,4-cyclohexylene, 1,4-cyclohexenylene, tetrahydropyran-2,5-diyl, 1,3-dioxane-2,5-diyl, 1,2-phenylene, 1,3-phenylene, 1,4-phenylene, pyrimidine-2,5-diyl or pyridine-2,5-diyl, and in the rings, at least one piece of hydrogen may be replaced by fluorine, chlorine, alkyl having 1 to 5 carbons, alkoxy having 1 to 5 carbons, or alkyl having 1 to 5 carbons in which at least one piece of hydrogen is replaced by fluorine or chlorine;

$Z^1$ and $Z^2$ are independently a single bond or alkylene having 1 to 10 carbons, and in the alkylene, at least one piece of —$CH_2$— may be replaced by —O—, —S—, —CO—, —COO— or —OCO—, and at least one piece of —$CH_2$—$CH_2$— may be replaced by —CH=CH— or —C≡C—, and in the groups, at least one piece of hydrogen may be replaced by fluorine or chlorine; and a is 1, 2 or 3.

Item 4. The compound according to item 1, wherein, in formula (1), $R^1$, $R^2$, $R^3$ and $R^4$ are independently hydrogen or alkyl having 1 to 4 carbons, and $R^5$ is hydrogen, hydroxy, oxy radical, alkyl having 1 to 10 carbons or alkoxy having 1 to 10 carbons;

ring $A^1$ is 1,4-cyclohexylene, 1,4-cyclohexenylene 1,2-phenylene, 1,3-phenylene or 1,4-phenylene, and the rings, at least one piece of hydrogen may be replaced by fluorine, chlorine, alkyl having 1 to 5 carbons, alkoxy having 1 to 5 carbons, or alkyl having 1 to 5 carbons in which at least one piece of hydrogen is replaced by fluorine or chlorine;

$Z^1$ and $Z^2$ are independently a single bond or alkylene having 1 to 10 carbons, and in the alkylene, at least one piece of $-CH_2-$ may be replaced by $-O-$, $-CO-$, $-OCO-$ or $-OCO-$, and at least one piece of $-CH_2-CH_2-$ may be replaced by $-CH=CH-$, and in the groups, at least one piece of hydrogen may be replaced by fluorine or chlorine; and a is 1, 2 or 3.

Item 5. The compound according to item 1, represented by formula (1a), formula (1b) or formula (1c):

(1a)

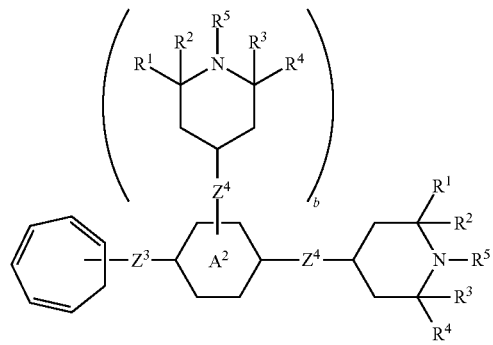

(1b)

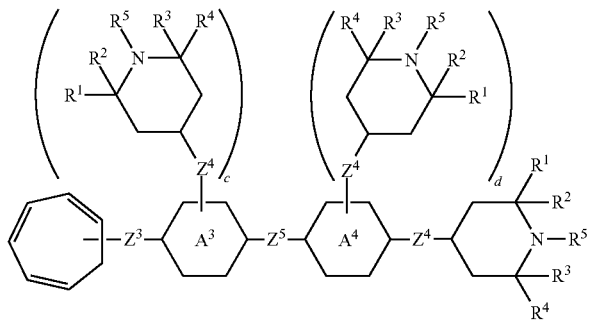

(1c)

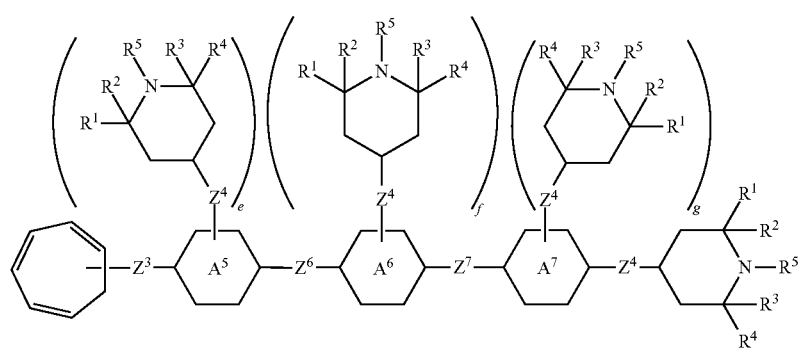

wherein, in formula (1a), formula (1b) or formula (1c), $R^1$, $R^2$, $R^3$ and $R^4$ are independently hydrogen or alkyl having 1 to 4 carbons, and $R^5$ is hydrogen, hydroxy, oxy radical, alkyl having 1 to 10 carbons or alkoxy having 1 to 10 carbons;

ring $A^2$, ring $A^3$, ring $A^4$, ring $A^5$, ring $A^6$ and ring $A^7$ are independently 1,4-cyclohexylene, 1,4-cyclohexenylene or 1,4-phenylene, and in the rings, at least one piece of hydrogen may be replaced by fluorine or chlorine;

$Z^3$, $Z^4$, $Z^5$, $Z^6$ and $Z^7$ are independently a single bond or alkylene having 1 to 10 carbons, and in the alkylene, at least one piece of $-CH_2-$ may be replaced by $-O-$, $-CO-$, $-COO-$ or $-OCO-$, and at least one piece of $-CH_2-CH_2-$ may be replaced by $-CH=CH-$, and in the groups, at least one piece of hydrogen may be replaced by fluorine or chlorine; and b, c, d, e, f and g are 0 or 1, a sum of c and d is 0 or 1, and a sum of e, f, and g is 0 or 1.

Item 6. The compound according to any one of items 1 to 5, represented by formula (1d), formula (1e) or formula (1f):

(1d)

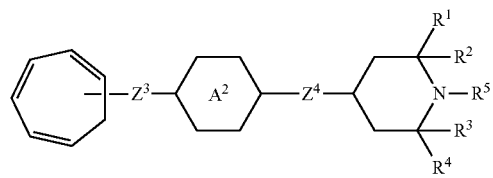

(1e)

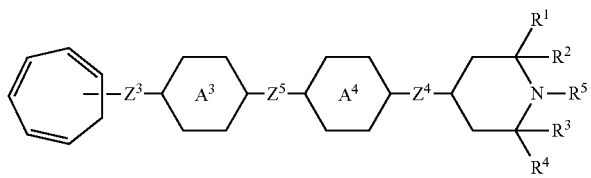

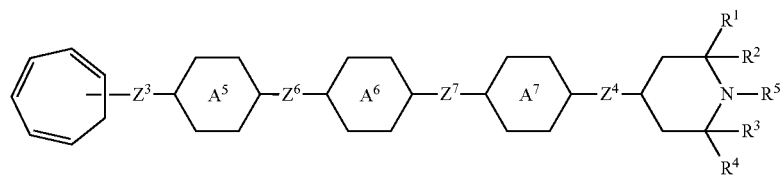
(1f)

wherein, in formula (1d), formula (1e) or formula (1f), $R^1$, $R^2$, $R^3$ and $R^4$ are independently hydrogen or alkyl having 1 to 4 carbons, and $R^5$ is hydrogen, hydroxy, oxy radical, alkyl having 1 to 10 carbons or alkoxy having 1 to 10 carbons;

ring $A^2$, ring $A^3$, ring $A^4$, ring $A^5$, ring $A^6$ and ring $A^7$ are independently 1,4-cyclohexylene, 1,4-cyclohexenylene or 1,4-phenylene, and in the rings, at least one piece of hydrogen may be replaced by fluorine; and $Z^3$, $Z^4$, $Z^5$, $Z^6$ and $Z^7$ are independently a single bond, —COO—, —OCO—, —CH$_2$O—, —OCH$_2$—, —CF$_2$O—, —OCF$_2$—, —CH$_2$CH$_2$— or —CH=CH—.

Item 7. The compound according to item 6, wherein, in formula (1d), formula (1e) or formula (1f), $R^1$, $R^2$, $R^3$ and $R^4$ are independently hydrogen or alkyl having 1 to 4 carbons, and $R^5$ is hydrogen, hydroxy, oxy radical, alkyl having 1 to 10 carbons or alkoxy having 1 to 10 carbons;

ring $A^2$, ring $A^3$, ring $A^4$, ring $A^5$, ring $A^6$ and ring $A^7$ are independently 1,4-phenylene or 1,4-phenylene in which at least one piece of hydrogen is replaced by fluorine; and $Z^3$, $Z^5$, $Z^6$ and $Z^7$ are independently a single bond, —COO—, —OCO—, —CH$_2$O—, —OCH$_2$— or —CH$_2$CH$_2$—, and $Z_4$ is —COO—.

Item 8. The compound according to any one of items 1 to 7, represented by formula (1g) or formula (1h):

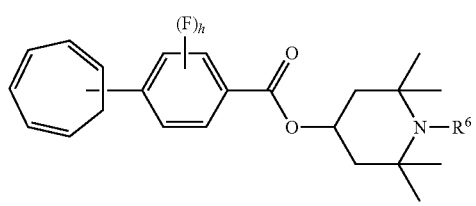
(1g)

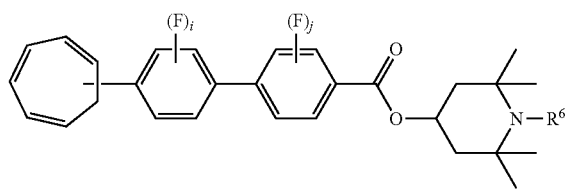
(1h)

wherein, in formula (1g) or formula (1h), $R^6$ is hydrogen, hydroxy, oxy radical, alkyl having 1 to 10 carbons or alkoxy having 1 to 10 carbons; and h, i and j are independently 0, 1 or 2.

Item 9. The compound according to any one of items 1 to 8, represented by formula (1i) or formula (1j):

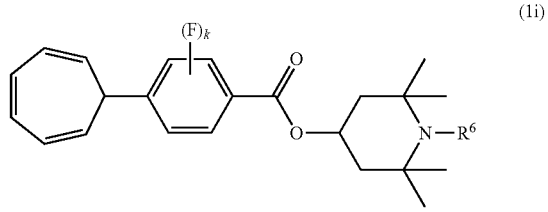
(1i)

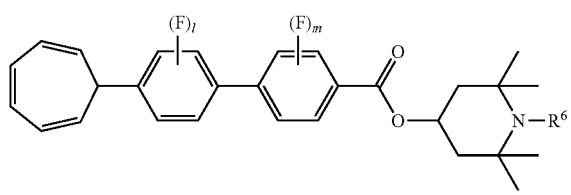
(1j)

wherein, in formula (1i) or formula (1j), $R^6$ is hydrogen, hydroxy, oxy radical, alkyl having 1 to 10 carbons or alkoxy having 1 to 10 carbons; and k, l and m are independently 0, 1 or 2.

Item 10. The compound according to any one of items 1 to 8, represented by formula (1k):

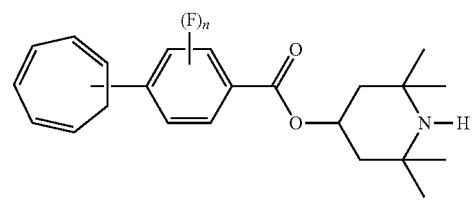
(1k)

wherein, in formula (1k), n is 0, 1 or 2.

Item 11. The compound according to any one of items 1 to 10, represented by formula (1l):

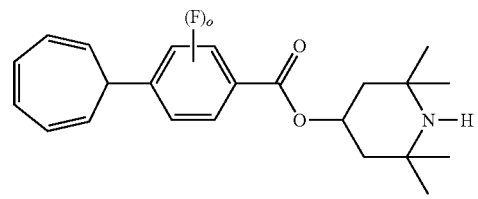
(1l)

wherein, in formula (1l), o is 0, 1 or 2.

Item 12. A liquid crystal composition, containing at least one compound according to any one of items 1 to 11.

Item 13. The liquid crystal composition according to item 12, further containing at least one compound selected from the group of compounds represented by formula (2) to formula (4):

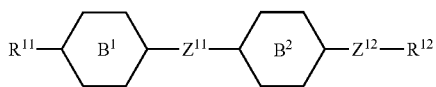
(2)

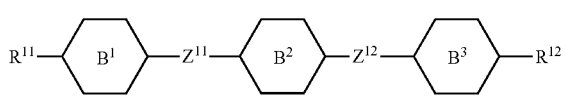
(3)

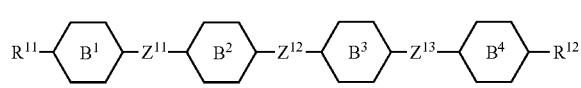
(4)

wherein, in formula (2) to formula (4), $R^{11}$ and $R^{12}$ are independently alkyl having 1 to 10 carbons or alkenyl having 2 to 10 carbons, and in the alkyl or the alkenyl, at least one piece of —$CH_2$— may be replaced by —O—, and at least one piece of hydrogen may be replaced by fluorine;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —$CH_2CH_2$—, —CH=CH—, —C≡C— or —COO—.

Item 14. The liquid crystal composition according to item 12 or 13, further containing at least one compound selected from the group of compounds represented by formula (5) to formula (7):

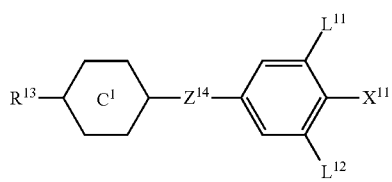
(5)

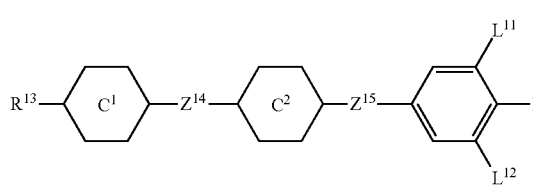
(6)

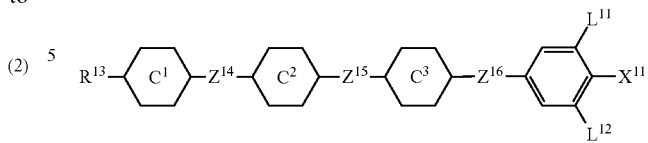
(7)

wherein, in formula (5) to formula (7), $R^{13}$ is alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $C^1$, ring $C^2$ and ring $C^3$ are independently 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl;

$Z^{14}$, $Z^{15}$ and $Z^{16}$ are independently a single bond, —$CH_2CH_2$—, —CH=CH—, —C≡C—, —COO—, —$CF_2O$—, —$OCF_2$—, —$CH_2O$— or —$(CH_2)_4$—; and $L^{11}$ and $L^{12}$ are independently hydrogen or fluorine.

Item 15. The liquid crystal composition according to item 12 or 13, further containing at least one compound selected from the group of compounds represented by formula (8):

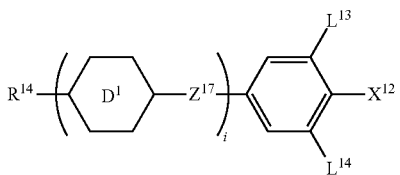
(8)

wherein, in formula (8), $R^{14}$ is alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine;

$X^{12}$ is —C≡N or —C≡C—C≡N; ring $D^1$ is 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl; $Z^{17}$ is a single bond, —$CH_2CH_2$—, —COO—, —$CF_2O$—, —$OCF_2$— or —$CH_2O$—; $L^{13}$ and $L^{14}$ are independently hydrogen or fluorine; and i is 1, 2, 3 or 4.

Item 16. The liquid crystal composition according to item 12 or 13, further containing at least one compound selected from the group of compounds represented by formula (9) to formula (15):

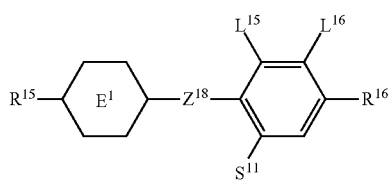
(9)

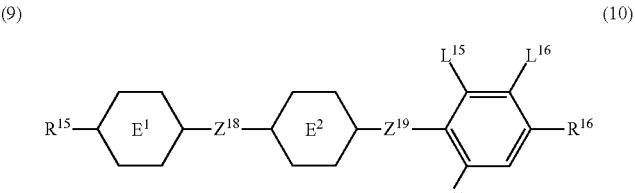
(10)

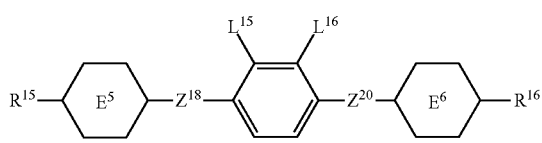
(11)

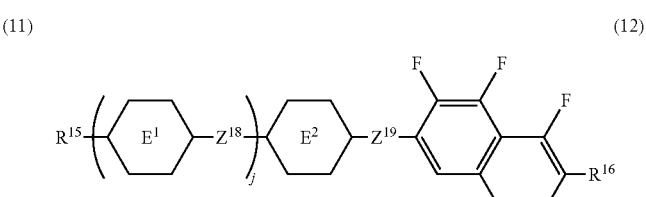
(12)

-continued

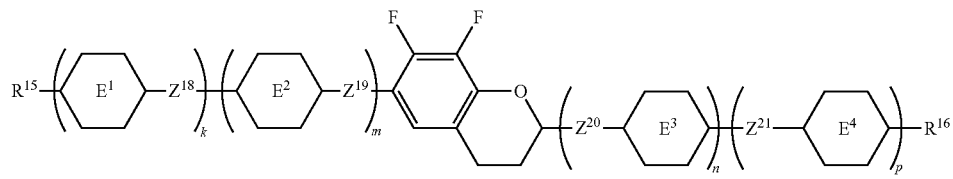

(13)

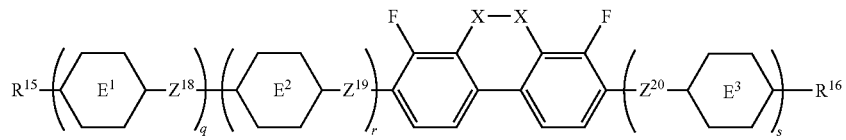

(14)

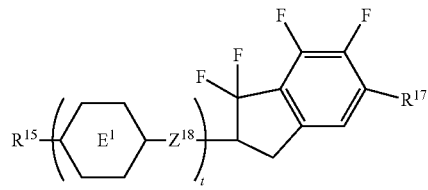

(15)

wherein, in formula (9) to formula (15), $R^{15}$ and $R^{16}$ are independently alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine;

$R^{17}$ is hydrogen, fluorine, alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine;

ring $E^1$, ring $E^2$, ring $E^3$ and ring $E^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

ring $E^5$ and ring $E^6$ are independently 1,4-cyclohexylene, 1,4-cyclohexenylene, 1,4-phenylene, tetrahydropyran-2,5-diyl or decahydronaphthalene-2,6-diyl; $Z'8$, $Z^{19}$, $Z^{20}$ and $Z^{21}$ are independently a single bond, —$CH_2CH_2$—, —COO—, —$CH_2O$—, —$OCF_2$— or —$OCF_2CH_2CH_2$—;

$L^{15}$ and $L^{16}$ are independently fluorine or chlorine;

$S^{11}$ is hydrogen or methyl;

X is —CHF— or —$CF_2$—; and j, k, m, n, p, q, r and s are independently 0 or 1, a sum of k, m, n and p is 1 or 2, a sum of q, r and s is 0, 1, 2 or 3, and t is 1, 2 or 3.

Item 17. A liquid crystal display device including at least one of the liquid crystal composition according to anyone of items 12 to 16.

The invention further includes the following items: (a) the liquid crystal composition further containing one, two or at least three of additives such as a polymerizable compound, a polymerization initiator, a polymerization inhibitor, an optically active compound, an antioxidant, an ultraviolet light absorber, a light stabilizer different from compound (1), a heat stabilizer and an antifoaming agent; (b) a polymerizable composition prepared by adding a polymerizable compound to the liquid crystal composition; (c) a liquid crystal composite prepared by polymerizing the polymerizable composition; (d) a liquid crystal display device having a polymer sustained alignment (PSA) mode, containing the liquid crystal composite. (e) Use as the light stabilizer of compound (1); (f) use as the heat stabilizer of compound (1); (g) use as a combination of the light stabilizer different from compound (1) and compound (1); and (h) use as an optical activity composition by adding the optically active compound to the liquid crystal composition.

An aspect of compound (1), synthesis of compound (1), the liquid crystal composition and the liquid crystal display device will be described in order.

1. Aspect of Compound (1)

Compound (1) according to the invention has a piperidine ring and a cycloheptatriene ring. The compound is useful as a hindered amine-based light stabilizer. The piperidine ring of compound (1) is suitable for trapping a decomposition product generated by a photoreaction of the liquid crystal compound. The cycloheptatriene ring of compound (1) is effective in preventing the liquid crystal compound from being decomposed by backlight, or light from the sun. The compound can be added to a mixture of the liquid crystal compounds, namely, the liquid crystal composition. The reason is that the compound has a high solubility in the liquid crystal composition. Compound (1) is likely to be also effective as the heat stabilizer.

When the liquid crystal display device is used for a long period of time, the liquid crystal compound tends to decompose by light to generate a decomposition product. The product is an impurity, and therefore is not preferred for the device. The reason is that the impurity causes reduction of a contrast ratio, generation of display unevenness, and a phenomenon such as image persistence. The phenomenon can be easily visually identified, and is also very marked even if a degree thereof is slight. Accordingly, a light stabilizer which can suppress an amount of the generated impurity to be smaller even by 1% in comparison with a conventional light stabilizer is preferred. Compound (1) is such a light stabilizer.

Specific examples of preferred compound (1) will be described. Specific examples of preferred substituent R, ring A and bonding group Z in compound (1) are applied also to a subordinate formula of compound (1). In compound (1), characteristics can be arbitrarily adjusted by suitably combining kinds of the groups. The characteristics of the compound have no significant difference, and therefore compound (1) may contain a larger amount of isotope such as $^2$H (deuterium) and $^{13}$C than natural abundance.

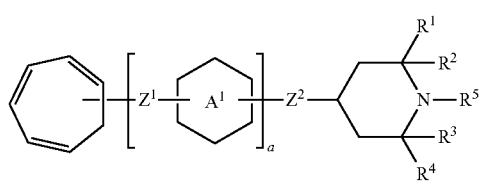

(1)

In formula (1), a straight line crossing the cycloheptatriene ring means that, when a is 1, bonding group $Z^1$ is bonded to any carbon on the cycloheptatriene ring. A same rule applies also to a case where a is 2 or 3. The straight line means that, when a is 0, bonding group $Z^2$ is bonded to any carbon of the cycloheptatriene ring. The straight line crossing ring $A^1$ means that bonding groups $Z^1$ and $Z^2$ are bonded to any carbon on ring $A^1$.

In formula (1) or formula (P-1), $R^1$, $R^2$, $R^3$ and $R^4$ are independently hydrogen or alkyl having 1 to 4 carbons. Preferred $R^1$, $R^2$, $R^3$ and $R^4$ are hydrogen, methyl, ethyl or a combination thereof. Further preferred $R^1$, $R^2$, $R^3$ and $R^4$ are hydrogen, methyl or a combination thereof. Particularly preferred $R^1$, $R^2$, $R^3$ and $R^4$ are methyl. More specifically, a preferred piperidyl group is 2,2,6,6-tetramethyl-4-piperidyl.

In formula (1) or formula (P-1), $R^5$ is hydrogen, hydroxy, oxy radical, alkyl having 1 to 10 carbons or alkoxy having 1 to 10 carbons. Hydroxy means —OH, and the oxy radical means a free radical having a part of >N—O—.. Preferred $R^5$ is hydrogen, hydroxy, oxy radical, alkyl having 1 to 3 carbons or alkoxy having 1 to 3 carbons. Further preferred $R^5$ is hydrogen, hydroxy, oxy radical, methyl, ethyl, propyl, isopropyl, methoxy or ethoxy. Particularly preferred $R^5$ is hydrogen, hydroxy, oxy radical, methyl or methoxy. Most preferred R5 is hydrogen, methyl or methoxy. Most preferred $R^5$ is also hydrogen, hydroxy] or methyl. Most preferred $R^5$ is also hydroxy, methyl or methoxy.

In formula (1), ring $A^1$ is 1,4-cyclohexylene, 1,4-cyclohexenylene, decahydronaphthalene-2,6-diyl, 3,4-dihydro-2H-pyrane-3,6-diyl, 3,4-dihydro-2H-pyrane-2,5-diyl, 3,6-dihydro-2H-pyrane-2,5-diyl, tetrahydropyran-2,5-diyl, 1,3-dioxane-2,5-diyl, 1,2-phenylene, 1,3-phenylene, 1,4-phenylene, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, pyrimidine-2,5-diyl or pyridine-2,5-diyl, and in the rings, at least one piece of hydrogen may be replaced by fluorine, chlorine, alkyl having 1 to 5 carbons, alkoxy having 1 to 5 carbons, or alkyl having 1 to 5 carbons in which at least one piece of hydrogen is replaced by fluorine or chlorine, and one piece of hydrogen may be replaced by a monovalent group represented by formula (P-1).

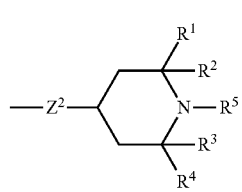

(P-1)

Preferred ring $A^1$ is 1,4-cyclohexylene, 1,4-cyclohexenylene, 1,4-phenylene, naphthalene-1,4-diyl or naphthalene-2,6-diyl, and in the rings, at least one piece of hydrogen may be replaced by fluorine. Further preferred ring $A^1$ is 1,4-cyclohexylene, 1,4-phenylene or naphthalene-2,6-diyl. Most preferred ring $A^1$ is 1,4-phenylene.

In formula (1) or formula (P-1), $Z^1$ and $Z^2$ are independently a single bond or alkylene having 1 to 10 carbons, and in the alkylene, at least one piece of —$CH_2$— may be replaced by —O—, —S—, —CO—, —COO— or —OCO—, and at least one piece of —$CH_2$—$CH_2$— may be replaced by —CH=CH— or —C≡C—, and in the groups, at least one piece of hydrogen may be replaced by fluorine or chlorine.

Preferred $Z^1$ or $Z^2$ is a single bond, —COO—, —OCO—, —$CH_2$O—, —O$CH_2$—, —$CF_2$O—, —O$CF_2$—, —$CH_2CH_2$— or —CH=CH—. Further preferred $Z^1$ or $Z^2$ is a single bond, —COO— or —OCO—. Particularly preferred $Z^1$ or $Z^2$ is a single bond or —COO—. Most preferred Z' is a single bond. Most preferred $Z^2$ is —COO—.

In formula (1), a is 0, 1, 2 or 3. Preferred a is 0 or 1. Further preferred a is 1.

Compound (1) having objective characteristics can be obtained by suitably selecting a combination of substituent R, ring A, bonding group Z and subscript a with reference to the preferred examples described above. Specific examples of preferred compound (1) include the compound described in item 2, item 3 or the like.

2. Synthesis of Compound (1)

A method for preparing compound (1) will be described. Compound (1) can be prepared by suitably combining methods of synthetic organic chemistry. The methods are described in books such as Houben-Weyl (Houben-Weyl, Methoden der Organische Chemie, Georg-Thieme Verlag, Stuttgart), Organic Syntheses (Organic Syntheses, John Wily & Sons, Inc.), Organic Reactions (Organic Reactions, John Wily & Sons Inc.), Comprehensive Organic Synthesis (Pergamon Press), and New Experimental Chemistry Course (Shin Jikken Kagaku Koza in Japanese) (Maruzen Co., Ltd.).

2-1. Formation of Bonding Group Z

First, a scheme is shown for a method for forming bonding group $Z^1$ or $Z^2$. Next, reactions described in the scheme in methods (1) to (11) are described. In the scheme, $MSG^1$ (or $MSG^2$) is a monovalent organic group having at least one ring. The monovalent organic groups represented by a plurality of $MSG^1$ (or $MSG^2$) used in the scheme may be identical or different. Compounds (1A) to (1J) correspond to compound (1).

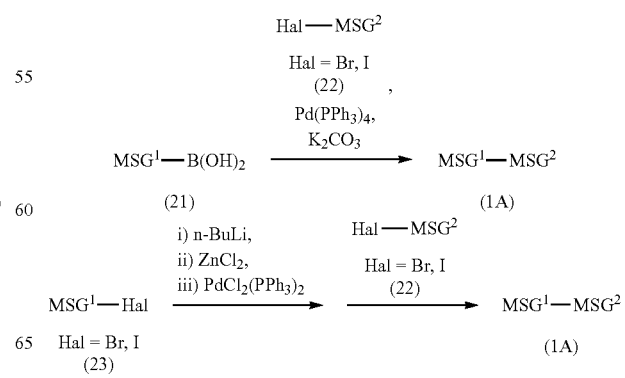

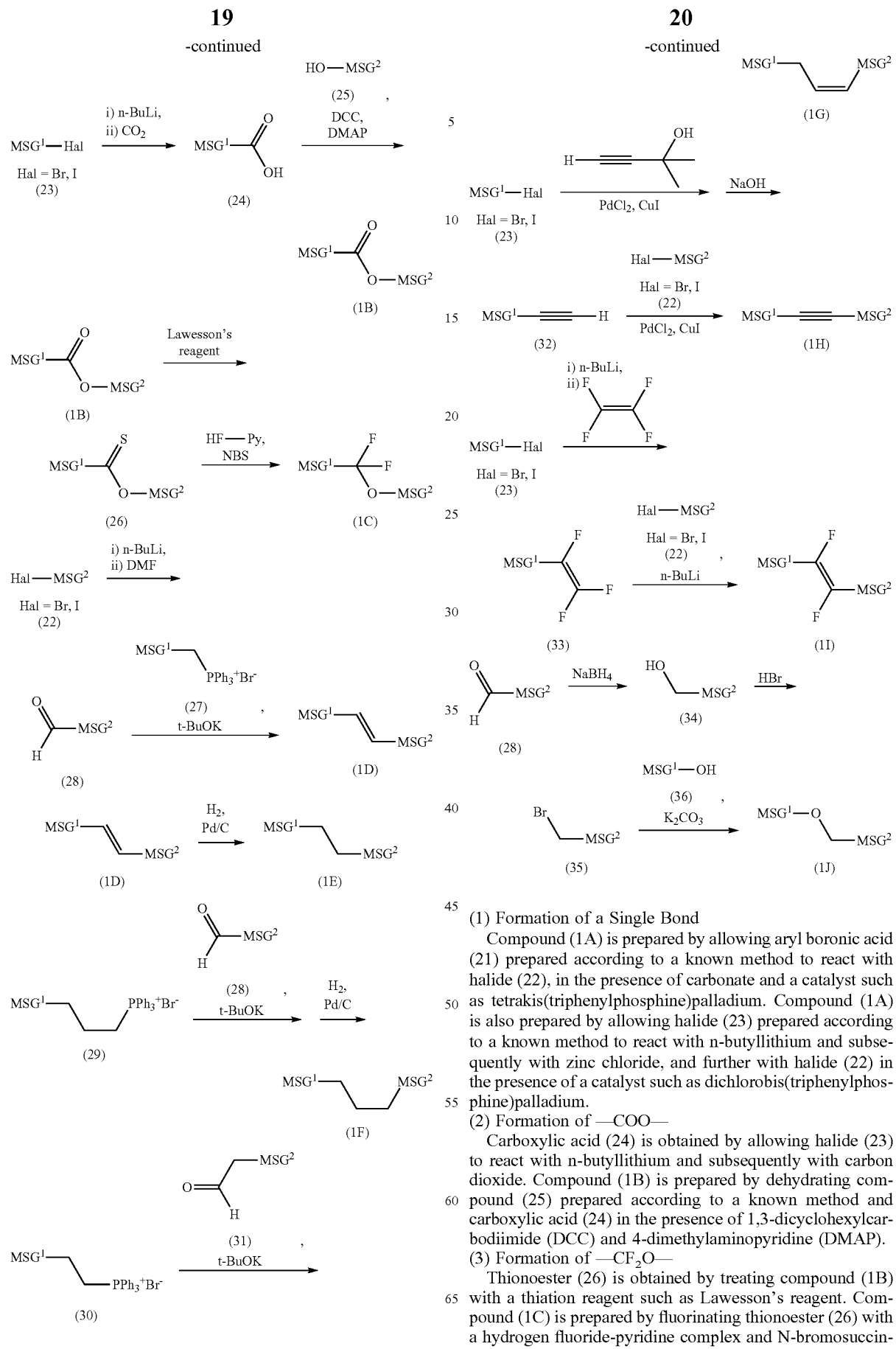

(1) Formation of a Single Bond

Compound (1A) is prepared by allowing aryl boronic acid (21) prepared according to a known method to react with halide (22), in the presence of carbonate and a catalyst such as tetrakis(triphenylphosphine)palladium. Compound (1A) is also prepared by allowing halide (23) prepared according to a known method to react with n-butyllithium and subsequently with zinc chloride, and further with halide (22) in the presence of a catalyst such as dichlorobis(triphenylphosphine)palladium.

(2) Formation of —COO—

Carboxylic acid (24) is obtained by allowing halide (23) to react with n-butyllithium and subsequently with carbon dioxide. Compound (1B) is prepared by dehydrating compound (25) prepared according to a known method and carboxylic acid (24) in the presence of 1,3-dicyclohexylcarbodiimide (DCC) and 4-dimethylaminopyridine (DMAP).

(3) Formation of —CF$_2$O—

Thionoester (26) is obtained by treating compound (1B) with a thiation reagent such as Lawesson's reagent. Compound (1C) is prepared by fluorinating thionoester (26) with a hydrogen fluoride-pyridine complex and N-bromosuccinimide (NBS). Refer to M. Kuroboshi et al., Chem. Lett., 1992, 827. Compound (1C) is also prepared by fluorinating thionoester (26) with (diethylamino)sulfur trifluoride (DAST). Refer to W. H. Bunnelle et al., J. Org. Chem. 1990, 55, 768. The bonding group can also be formed according to the method described in Peer. Kirsch et al., Angew. Chem. Int. Ed. 2001, 40, 1480.

(4) Formation of —CH═CH—

Aldehyde (28) is obtained by treating halide (22) with n-butyllithium and then allowing the treated halide to react with formamide such as N,N-dimethylformamide (DMF). Phosphorus ylide is generated by treating phosphonium salt (27) prepared according to a known method with a base such as potassium t-butoxide. Compound (1D) is prepared by allowing the phosphorus ylide to react with aldehyde (28). A cis isomer may be formed depending on reaction conditions, and the cis isomer is isomerized into a trans isomer according to a known method, when necessary.

(5) Formation of —$CH_2CH_2$—

Compound (1E) is prepared by hydrogenating compound (1D) in the presence of a catalyst such as palladium on carbon.

(6) Formation of —$(CH_2)_4$—

A compound having —$(CH_2)_2$—CH═CH— is obtained by using phosphonium salt (29) in place of phosphonium salt (27) according to the method in method (4). Compound (1F) is prepared by performing catalytic hydrogenation of the compound obtained.

(7) Formation of —$CH_2$CH═CH$CH_2$—

Compound (1G) is prepared according to method (4) by using phosphonium salt (30) in place of phosphonium salt (27), and aldehyde (31) in place of aldehyde (28). A trans isomer may be formed depending on reaction conditions, and the trans isomer is isomerized into a cis isomer according to a known method, when necessary.

(8) Formation of —C≡C—

Compound (32) is obtained by allowing halide (23) to react with 2-methyl-3-butyn-2-ol in the presence of a catalyst including dichloropalladium and copper halide, and then performing deprotection under basic conditions. Compound (1H) is prepared by allowing compound (32) to react with halide (22) in the presence of the catalyst including dichloropalladium and copper halide.

(9) Formation of —CF═CF—

Compound (33) is obtained by treating halide (23) with n-butyllithium, and then allowing the treated halide to react with tetrafluoroethylene. Compound (1I) is prepared by treating halide (22) with n-butyllithium, and then allowing the treated halide to react with compound (33).

(10) Formation of —OCH$_2$—

Compound (34) is obtained by reducing aldehyde (28) with a reducing agent such as sodium borohydride. Bromide (35) is obtained by brominating compound (34) with hydrobromic acid or the like. Compound (1J) is prepared by allowing bromide (35) to react with compound (36) in the presence of a base such as potassium carbonate.

(11) Formation of —$CF_2CF_2$—

A compound having —$(CF_2)_2$— is obtained by fluorinating diketone (—COCO—) with sulfur tetrafluoride, in the presence of a hydrogen fluoride catalyst, according to the method described in J. Am. Chem. Soc., 2001, 123, 5414.

2-2. Raw Materials of a Ring

Raw materials of a cyclohepta-1,3,5-triene ring are tropylium tetrafluoro borate, 2,4,6-cycloheptatriene-1-carbonitrile and so forth, which are available from Aldrich. Raw materials of a 2,2,6,6-tetramethylpiperidine ring are 4-hydroxy-2,2,6,6-tetramethylpiperidine, 2,2,6,6-tetramethyl-4-piperidone and so forth, which are available from Sigma-Aldrich Co., LLC.

3. Liquid Crystal Composition 3-1. Component Compound

A liquid crystal composition of the invention will be described. The composition contains at least one compound (1) as component A. The composition may contain two, three or more compounds (1). A preferred proportion of compound (1) is about 0.01% by weight or more based on the weight of the liquid crystal composition for maintaining a high stability to ultraviolet light, and about 5% by weight or less based thereon for allowing dissolution into the liquid crystal composition. A further preferred proportion is in the range of about 0.05% by weight to about 2% by weight. A most preferred proportion is in the range of about 0.05% by weight to about 1% by weight.

TABLE 2

Dielectric Anisotropy of Component Compound

| Component of Compound | Component Compound | Dielectric Anisotropy |
|---|---|---|
| Component A | Compound (1) | No |
| Component B | Compound (2) to Compound (4) | Small |
| Component C | Compound (5) to Compound (7) | Positively large |
| Component D | Compound (8) | Positively large |
| Component E | Compound (9) to Compound (15) | Negatively large |

The composition preferably contains compound (1) as component A, and further contains the liquid crystal compound selected from components B, C, D and E shown in Table 2. When the composition is prepared, components B, C, D and E are preferably selected by taking into account a positive or negative dielectric anisotropy and magnitude of the dielectric anisotropy. The composition may contain a liquid crystal compound different from compounds (1) to (15). The composition needs not contain such a liquid crystal compound.

Component B includes a compound in which two terminal groups are alkyl or the like. Specific examples of preferred component B include compounds (2-1) to (2-11), compounds (3-1) to (3-19) and compounds (4-1) to (4-7). In the compounds, $R^{11}$ and $R^{12}$ are independently alkyl having 1 to 10 carbons or alkenyl having 2 to 10 carbons, and in the alkyl and the alkenyl, at least one piece of —$CH_2$— may be replaced by —O—, and in the groups, at least one piece of hydrogen may be replaced by fluorine.

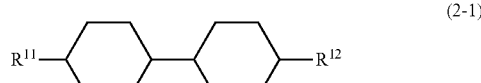

(2-1)

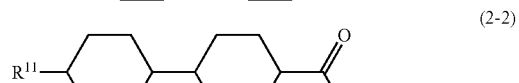

(2-2)

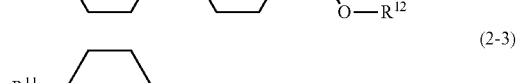

(2-3)

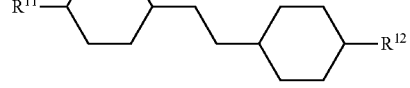

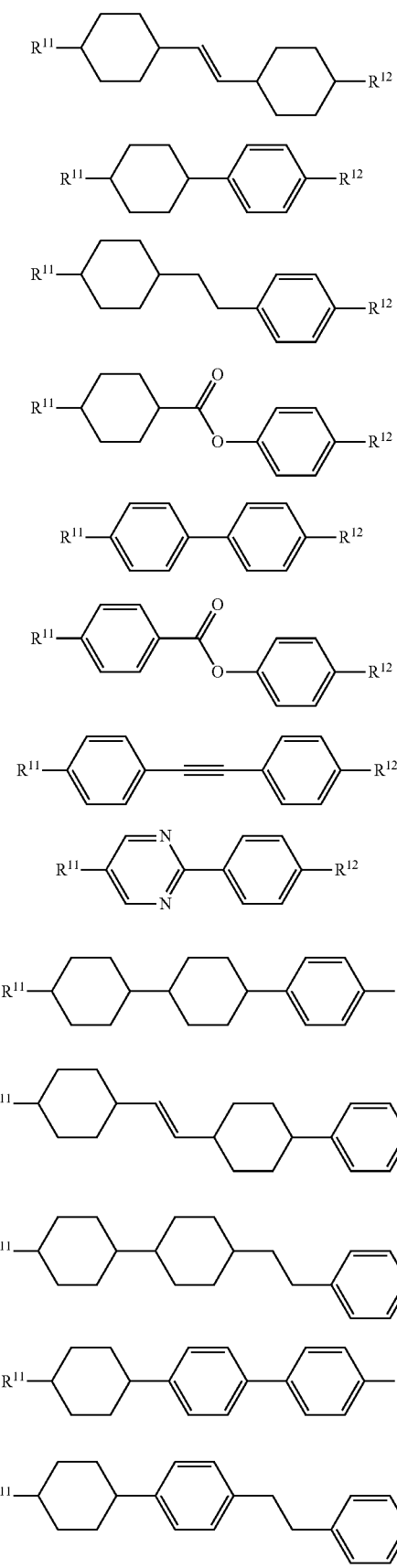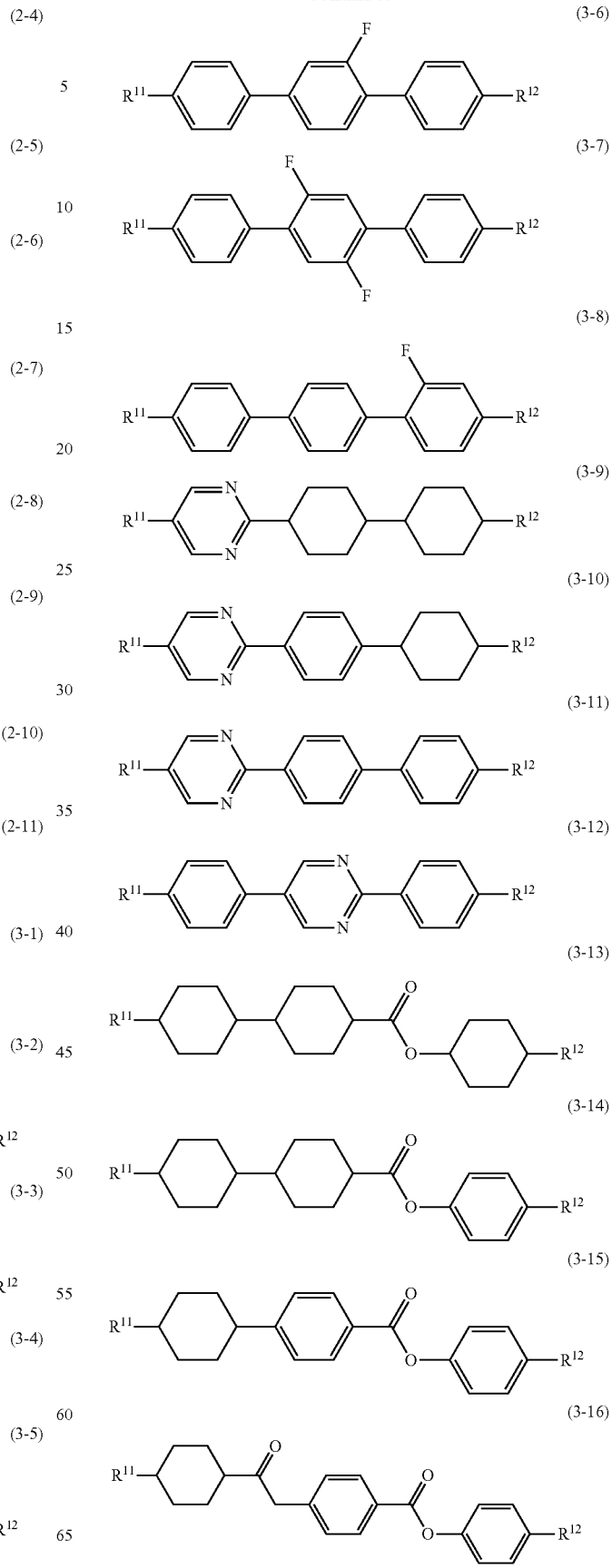

-continued

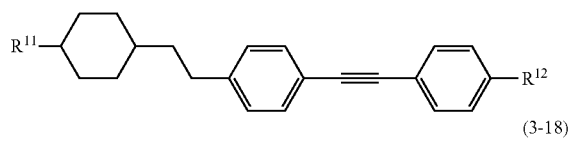
(3-17)

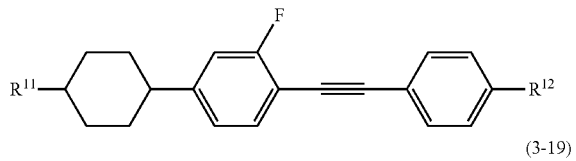
(3-18)

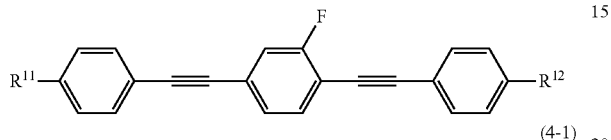
(3-19)

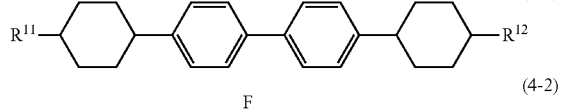
(4-1)

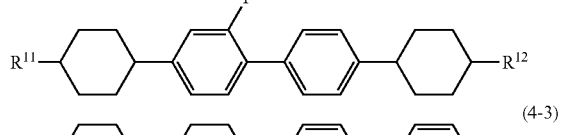
(4-2)

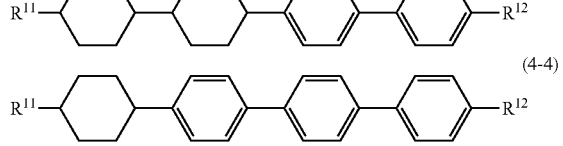
(4-3)

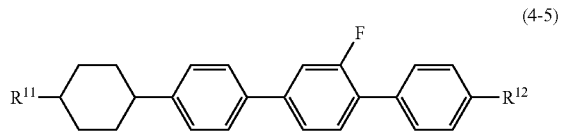
(4-4)

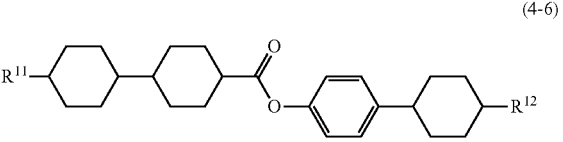
(4-5)

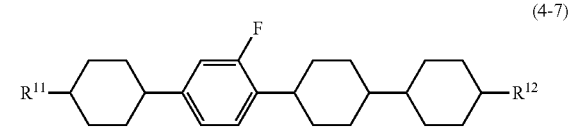
(4-6)

(4-7)

Component B has a small dielectric anisotropy. Component B is close to neutrality. Compound (2) is effective in decreasing the viscosity or adjusting the optical anisotropy. Compounds (3) and (4) are effective in extending the temperature range of the nematic phase by increasing the maximum temperature, or in adjusting the optical anisotropy.

As a content of component B is increased, the viscosity of the composition is decreased, and the dielectric anisotropy is decreased. Thus, as long as a desired value of threshold voltage of the device is met, the content is preferably as large as possible. When a composition for the IPS mode, the VA mode or the like is prepared, the content of component B is preferably about 30% by weight or more, and further preferably about 40% by weight or more, based on the weight of the liquid crystal composition.

Component C is a compound having a halogen-containing group or a fluorine-containing group at a right terminal. Specific examples of preferred component C include compounds (5-1) to (5-16), compounds (6-1) to (6-113) and compounds (7-1) to (7-57). In the compounds, $R^{13}$ is alkyl having 1 to 10 carbons or alkenyl having 2 to 10 carbons, and in the alkyl and the alkenyl, at least one piece of —$CH_2$— may be replaced by —O—, and in the groups, at least one piece of hydrogen may be replaced by fluorine. $X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$.

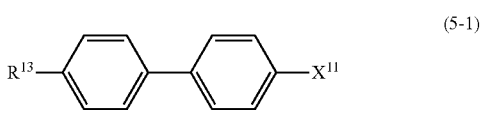
(5-1)

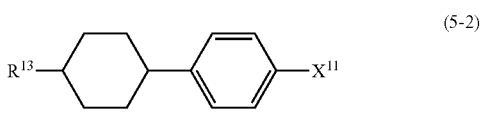
(5-2)

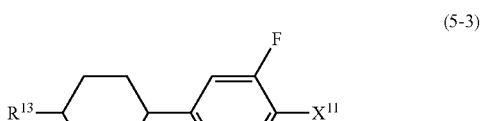
(5-3)

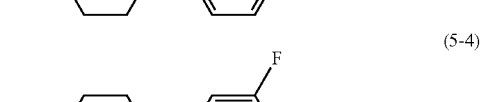
(5-4)

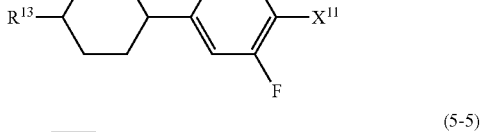
(5-5)

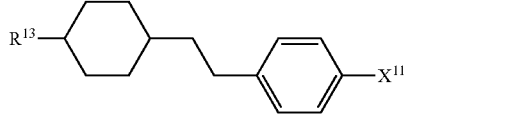
(5-6)

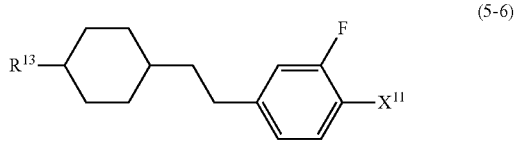
(5-7)

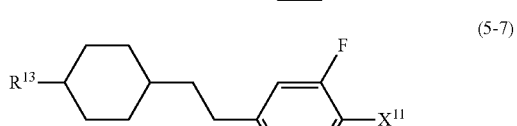
(5-8)

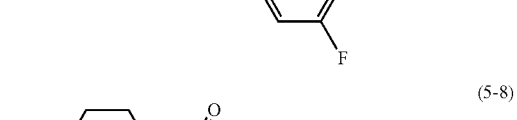
(5-9)

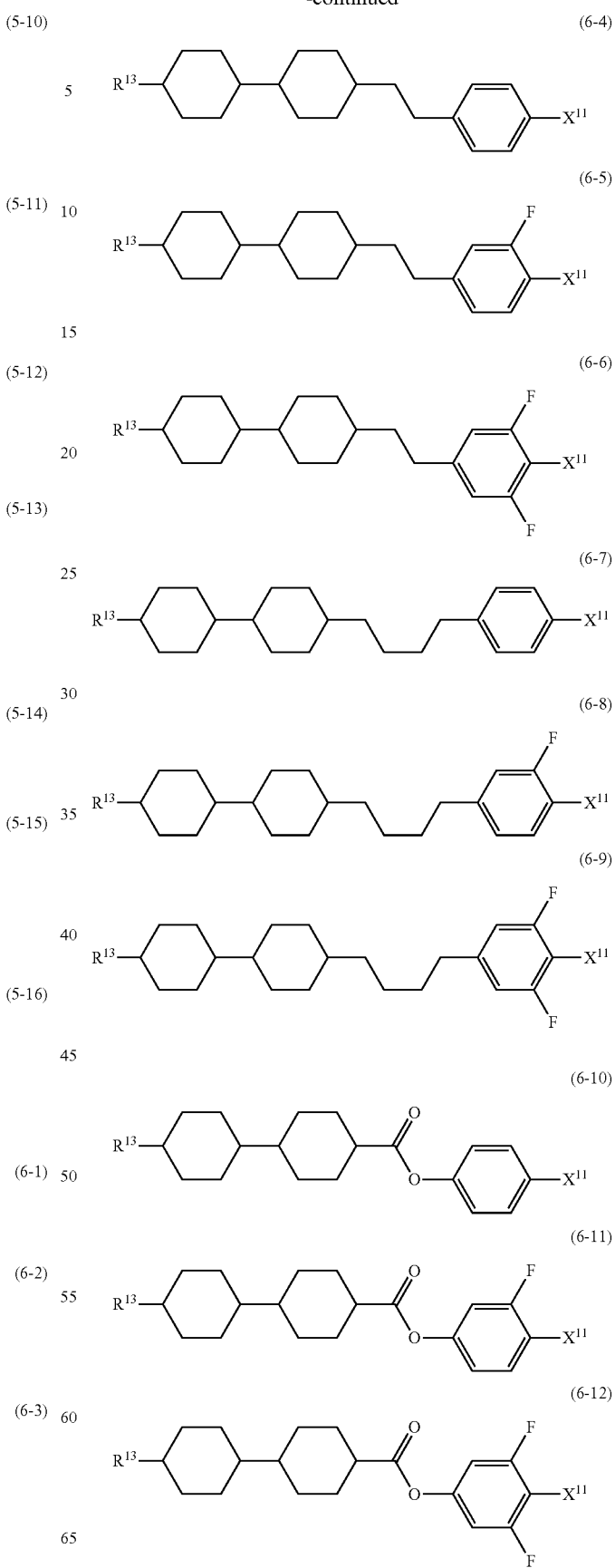

(6-13) 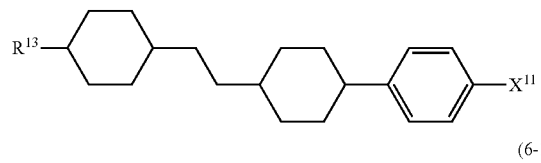
(6-14) 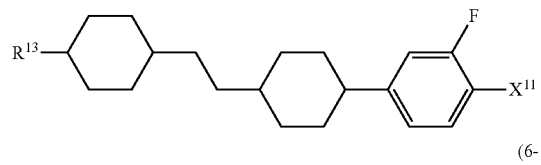
(6-15) 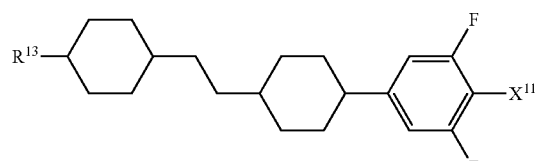
(6-16) 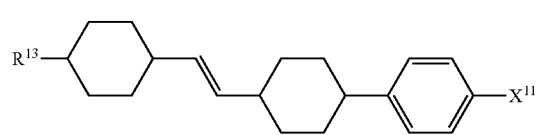
(6-17) 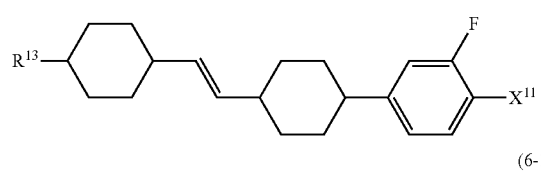
(6-18) 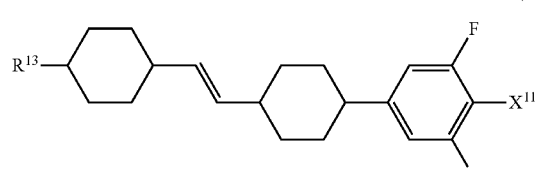
(6-19) 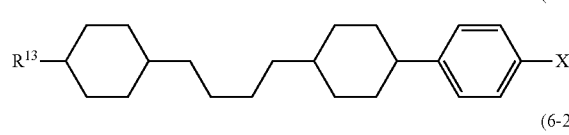
(6-20) 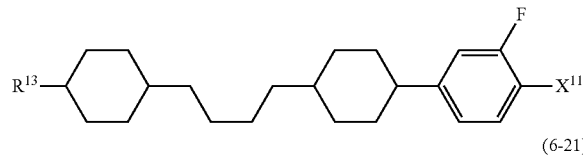
(6-21) 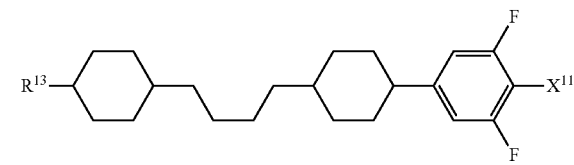
(6-22) 
(6-23) 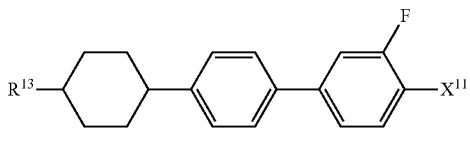
(6-24) 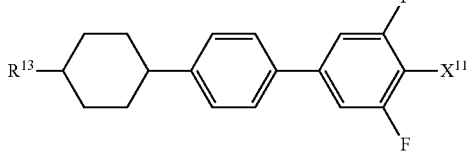
(6-25) 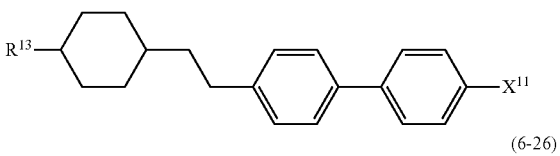
(6-26) 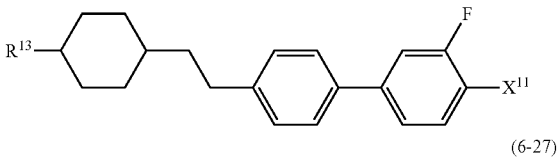
(6-27) 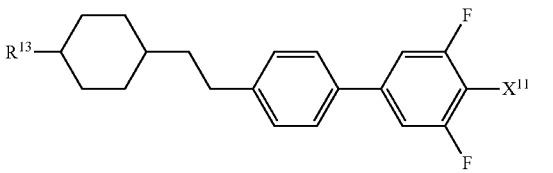
(6-28) 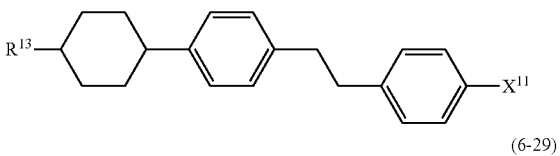
(6-29) 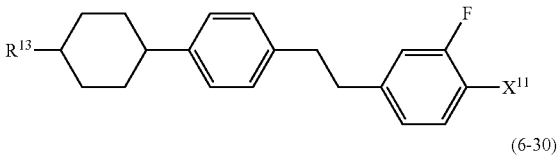
(6-30) 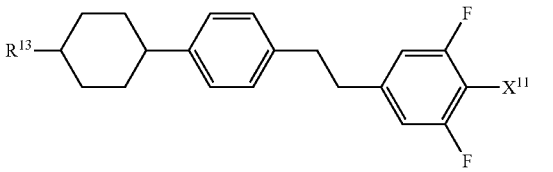
(6-31) 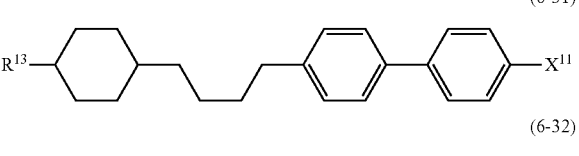
(6-32) 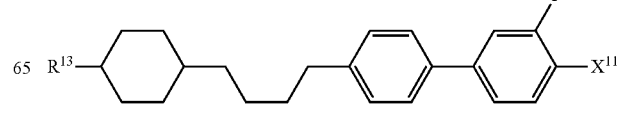

(6-33) 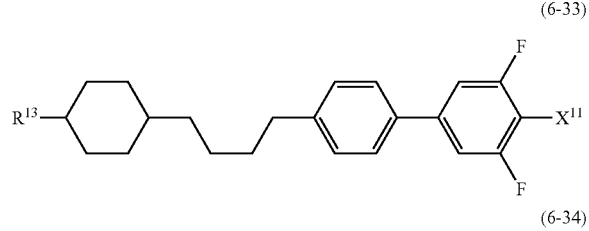
(6-34) 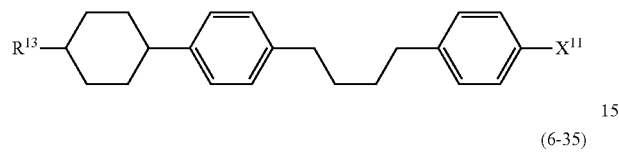
(6-35) 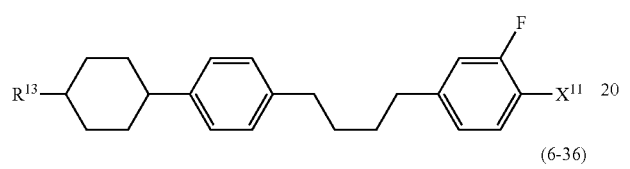
(6-36) 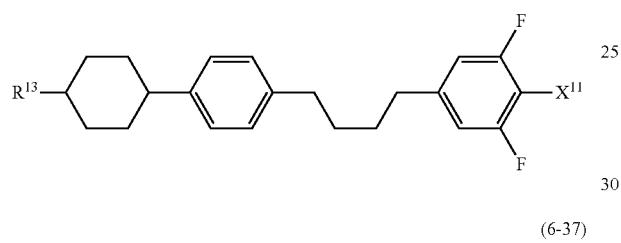
(6-37) 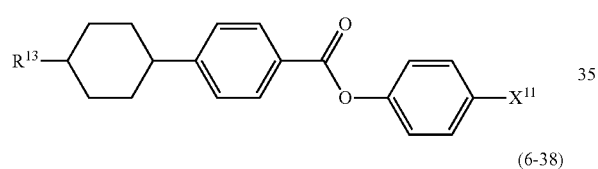
(6-38) 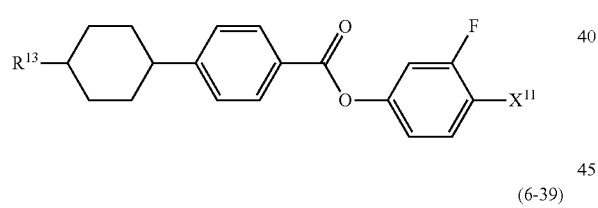
(6-39) 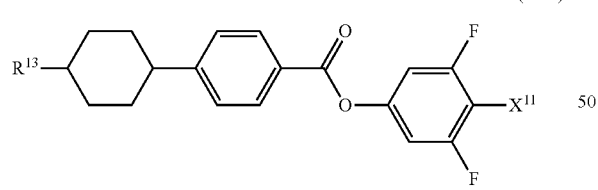
(6-40) 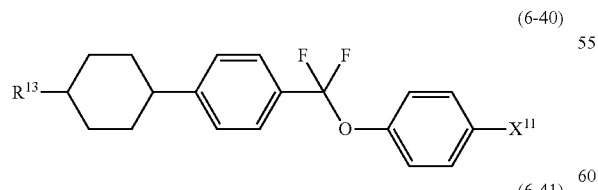
(6-41) 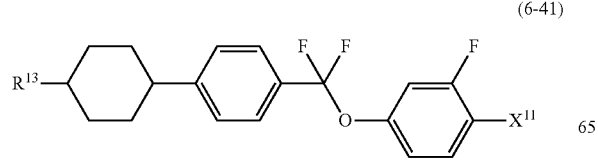
(6-42) 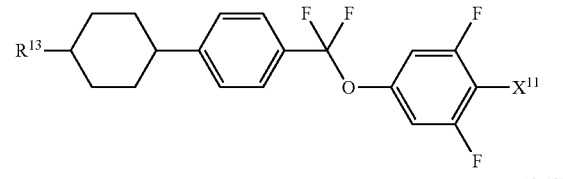
(6-43) 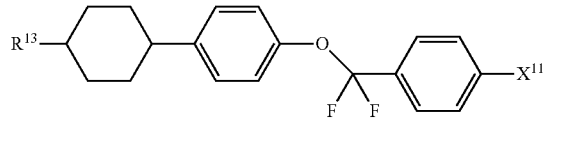
(6-44) 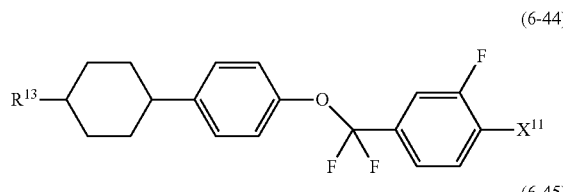
(6-45) 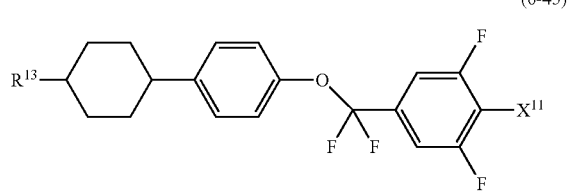
(6-46) 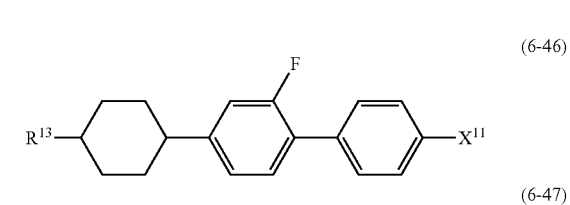
(6-47) 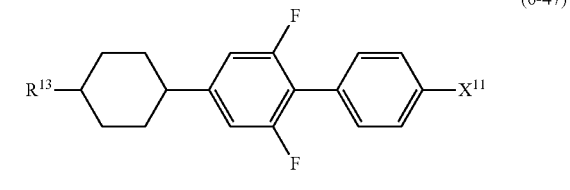
(6-48) 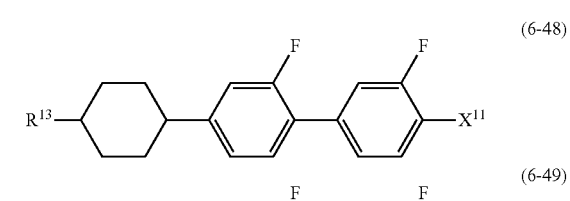
(6-49) 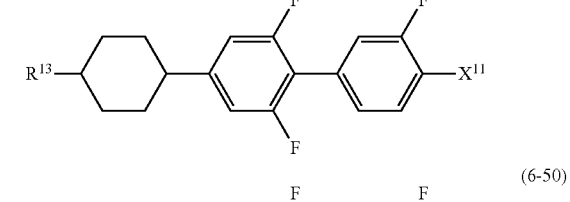
(6-50)

(6-51) 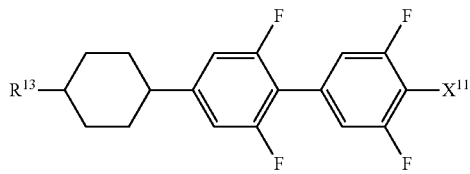
(6-52) 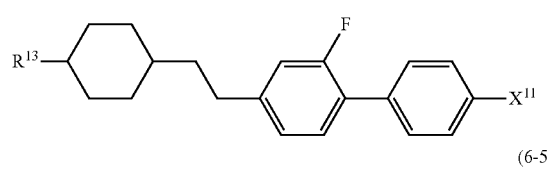
(6-53) 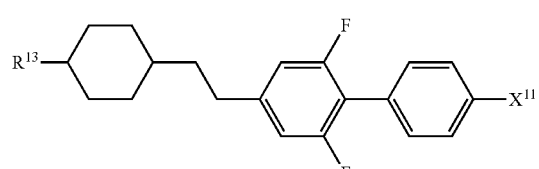
(6-54) 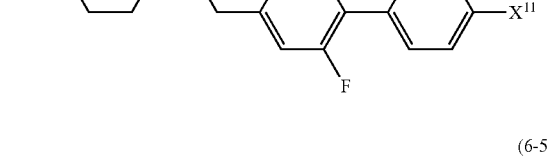
(6-55) 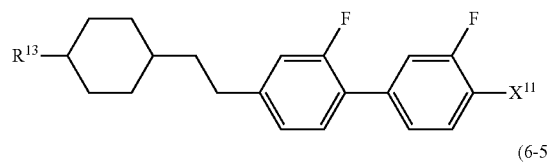
(6-56) 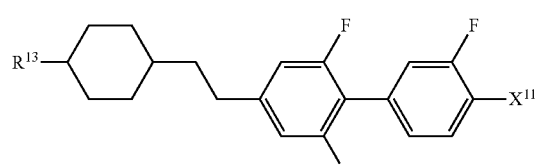
(6-57) 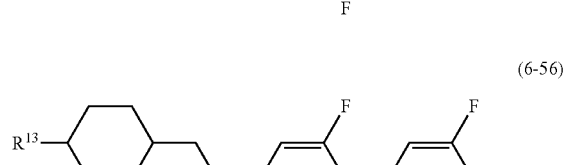
(6-58) 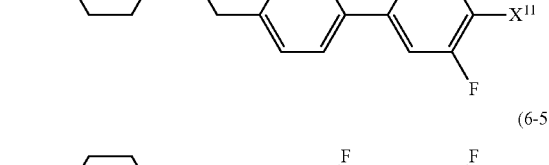
(6-59) 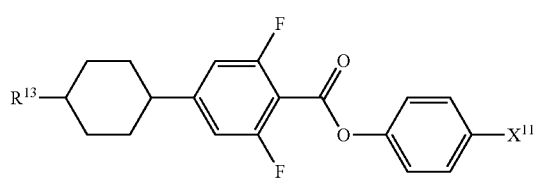
(6-60) 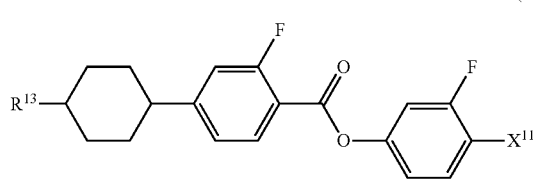
(6-61) 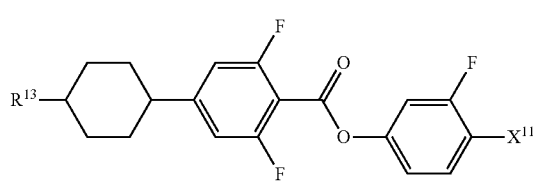
(6-62) 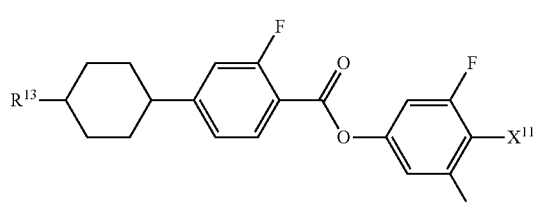
(6-63) 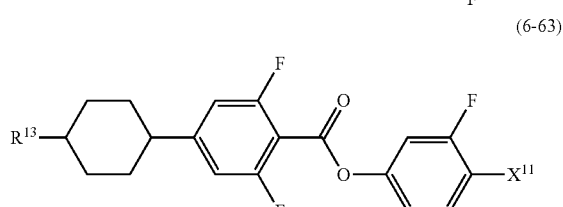
(6-64) 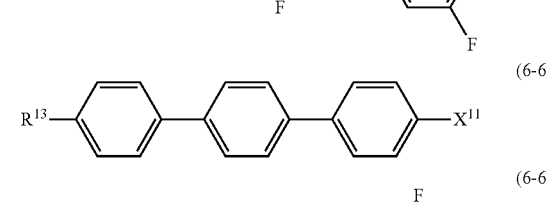
(6-65) 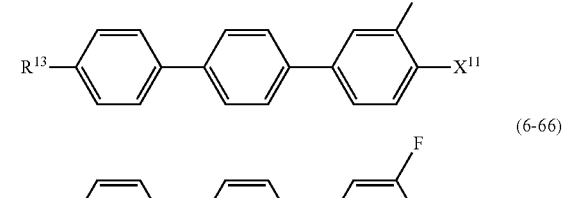
(6-66) 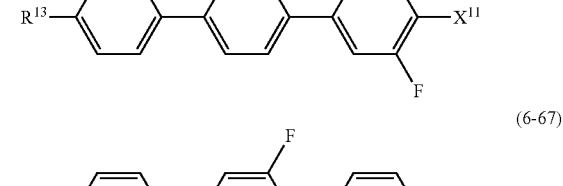
(6-67) 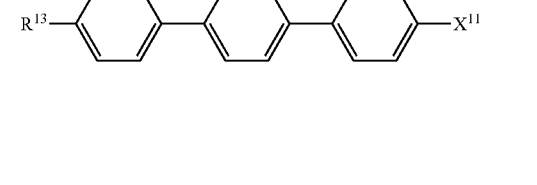

(6-68) 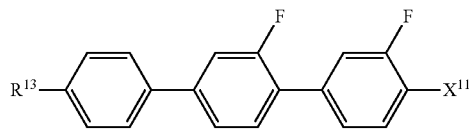
(6-69) 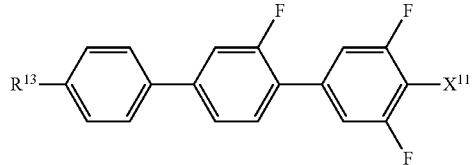
(6-70) 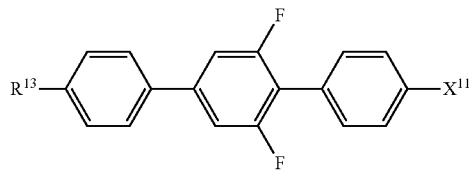
(6-71) 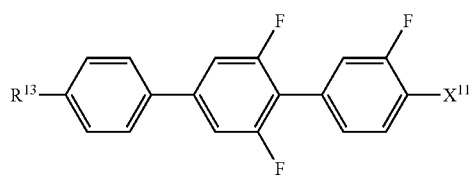
(6-72) 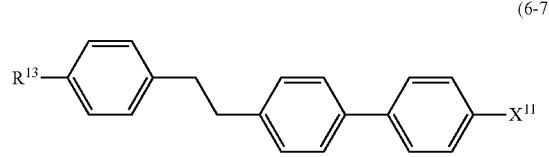
(6-73) 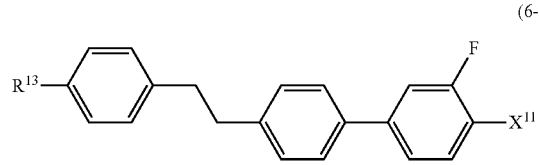
(6-74) 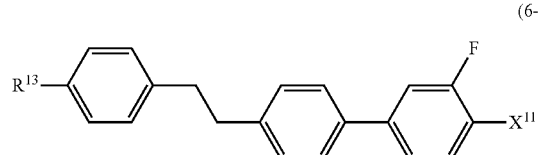
(6-75) 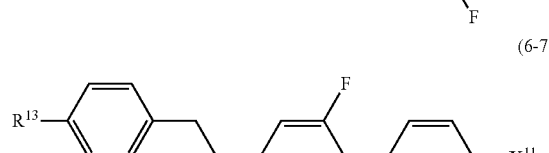
(6-76) 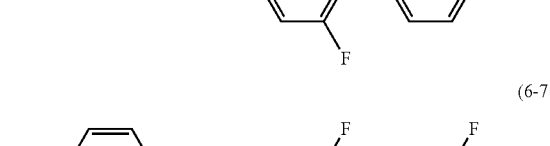
(6-77) 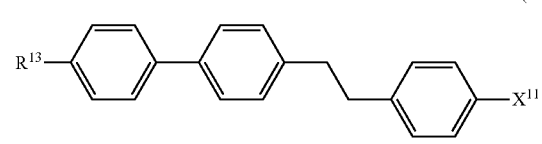
(6-78) 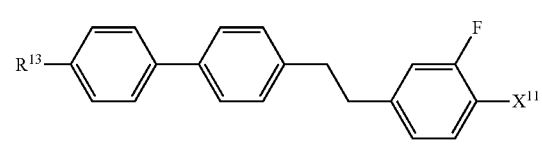
(6-79) 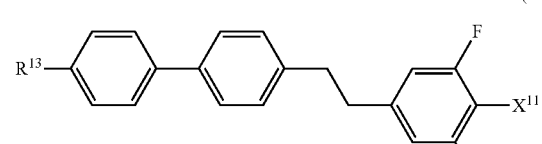
(6-80) 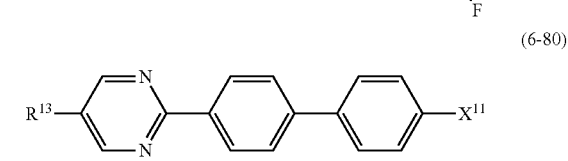
(6-81) 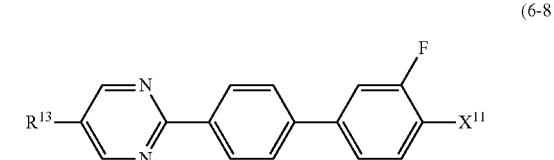
(6-82) 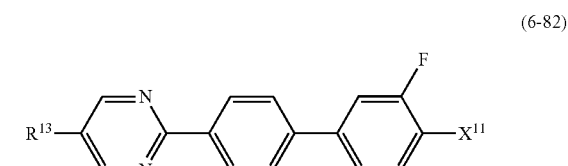
(6-83) 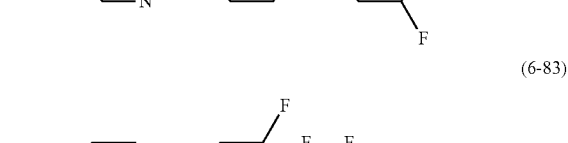
(6-84) 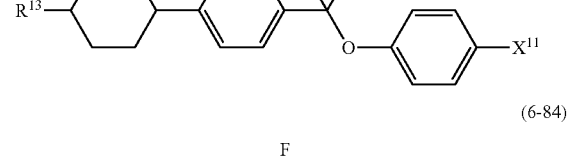
(6-85) 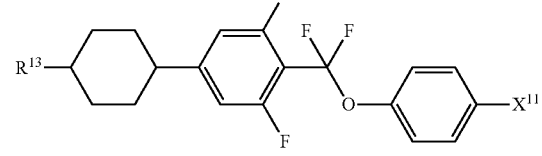

(6-86) 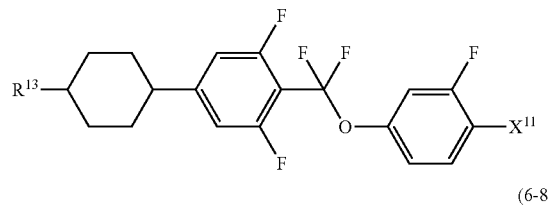
(6-87) 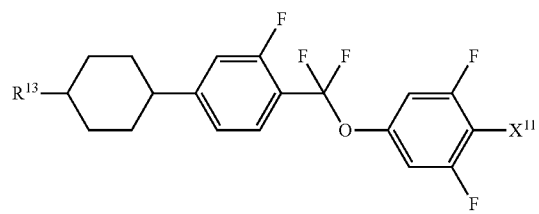
(6-88) 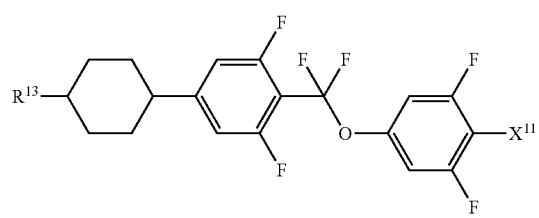
(6-89) 
(6-90) 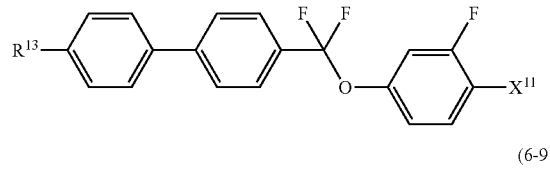
(6-91) 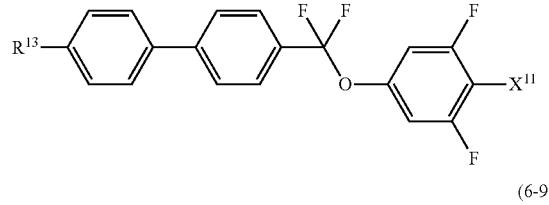
(6-92) 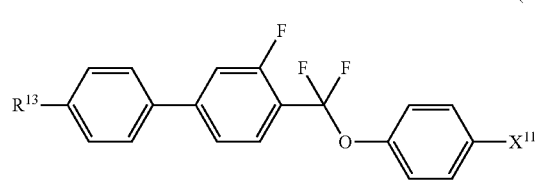
(6-93) 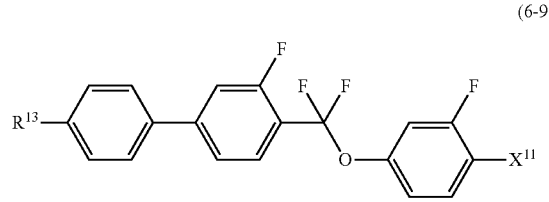
(6-94) 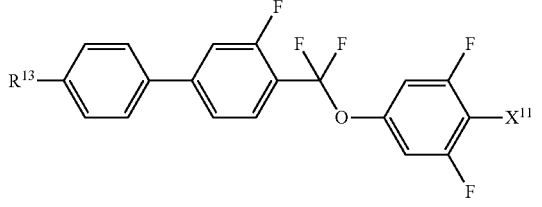
(6-95) 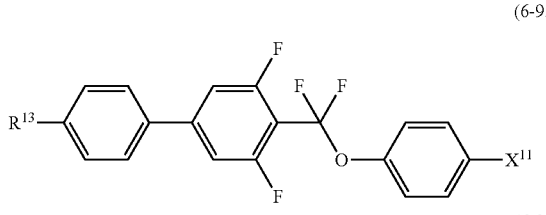
(6-96) 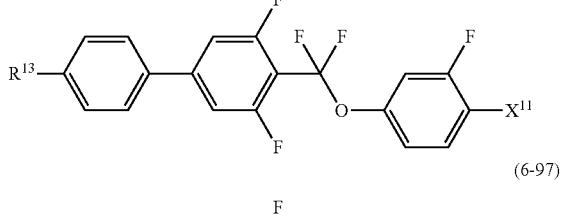
(6-97) 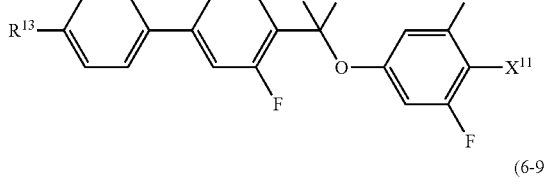
(6-98) 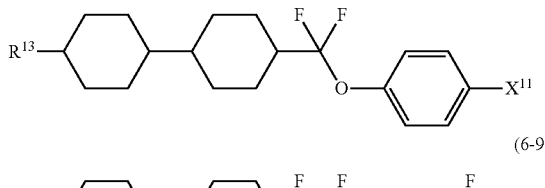
(6-99) 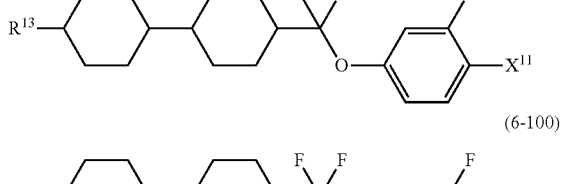
(6-100) 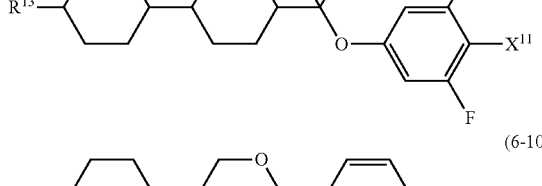
(6-101) 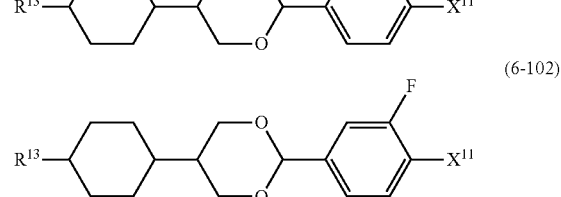
(6-102)

(6-103)
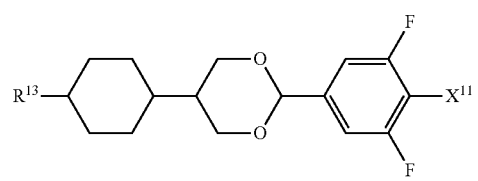
(6-104)
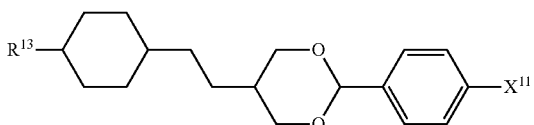
(6-105)
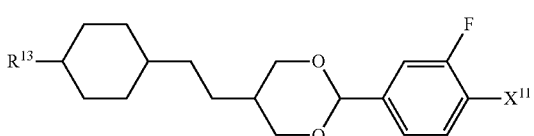
(6-106)
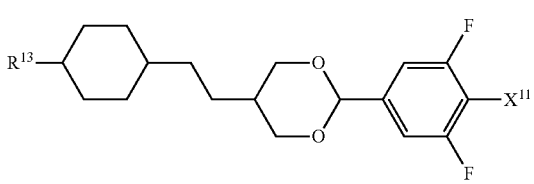
(6-107)
(6-108)
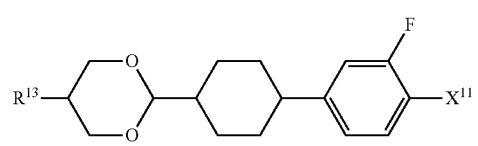
(6-109)
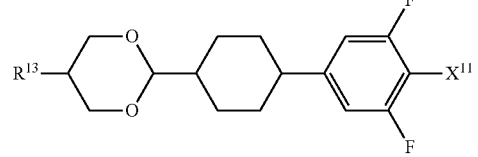
(6-110)
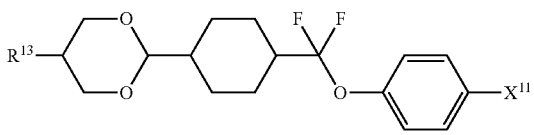
(6-111)
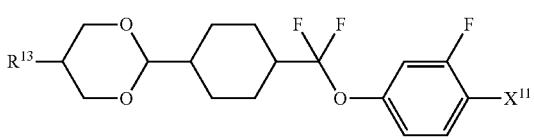
(6-112)
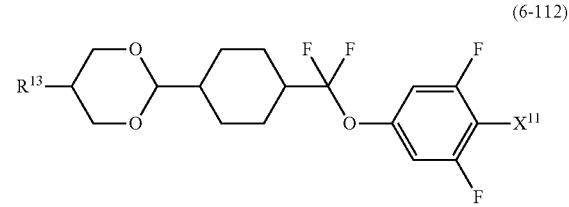
(6-113)
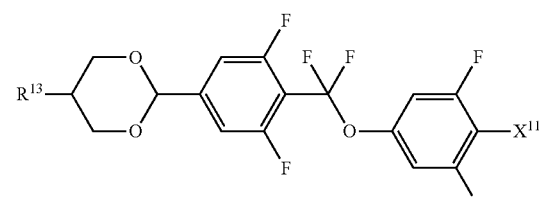
(7-1)
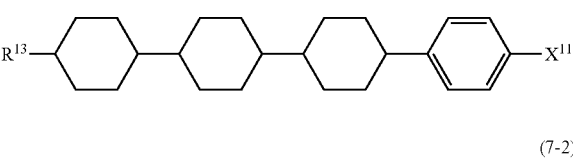
(7-2)
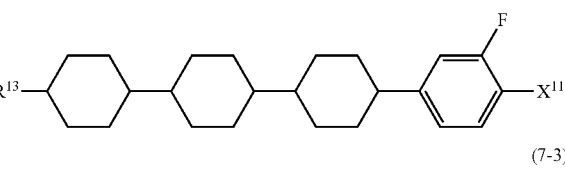
(7-3)
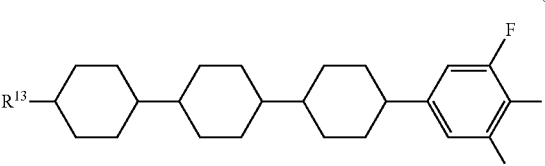
(7-4)
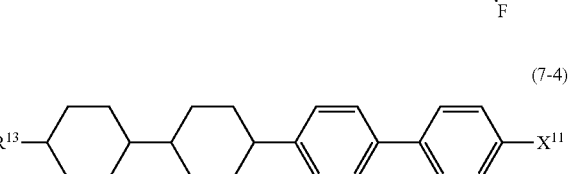
(7-5)
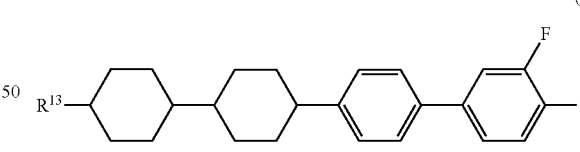
(7-6)
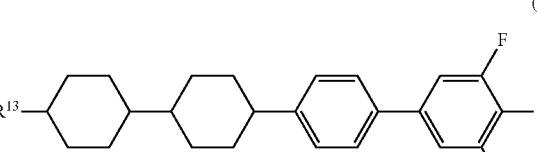
(7-7)
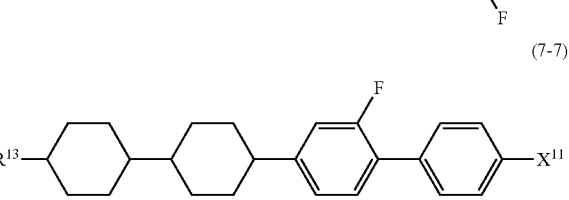

(7-8)
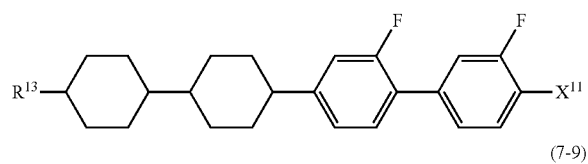
(7-9)
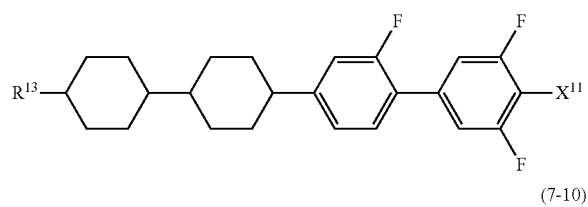
(7-10)
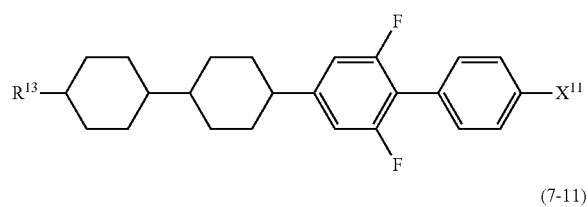
(7-11)
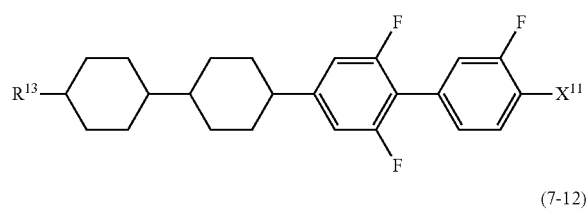
(7-12)
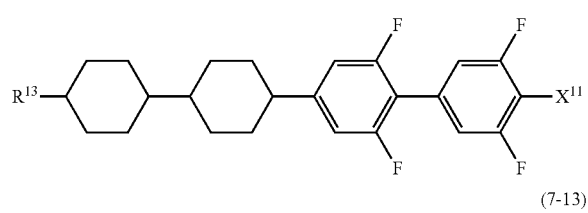
(7-13)
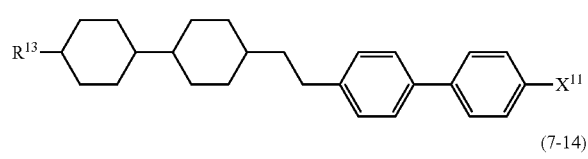
(7-14)
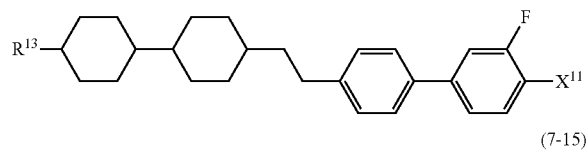
(7-15)
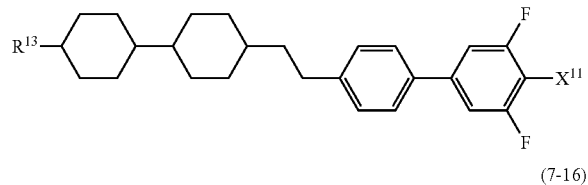
(7-16)
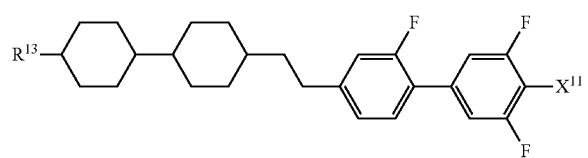
(7-17)
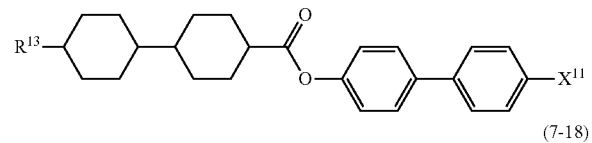
(7-18)
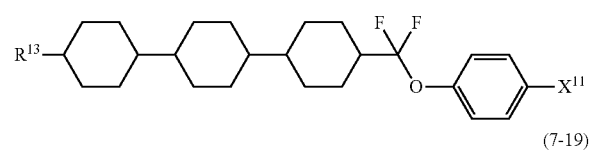
(7-19)
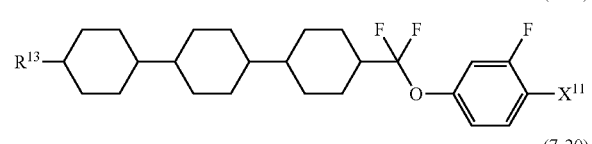
(7-20)
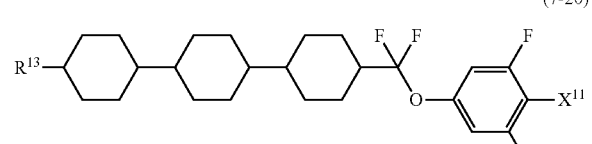
(7-21)
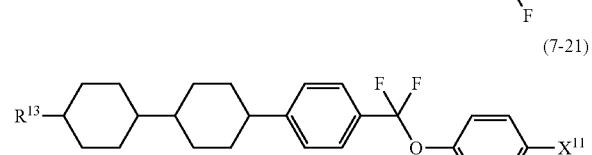
(7-22)
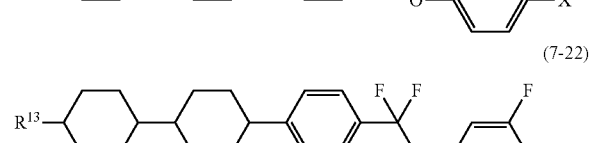
(7-23)
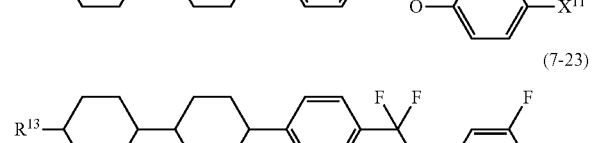
(7-24)
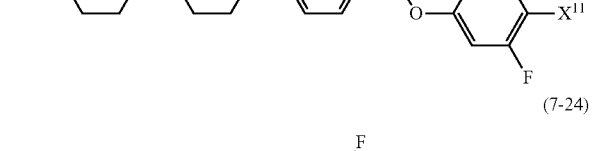
(7-25)
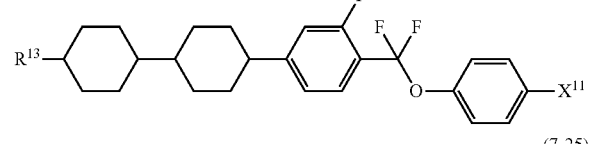
(7-26)
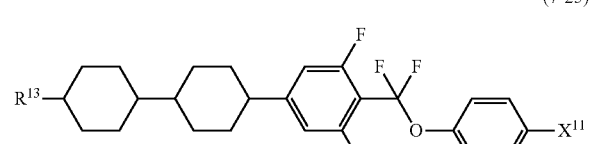
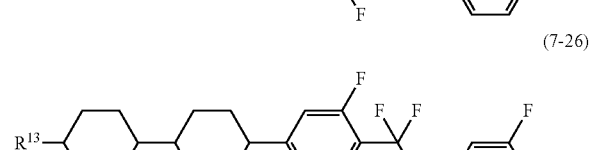

(7-27)
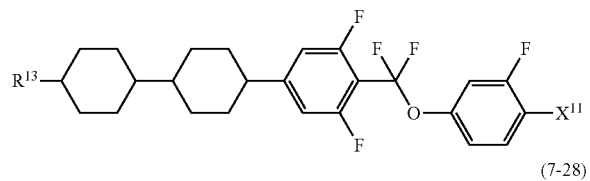
(7-28)
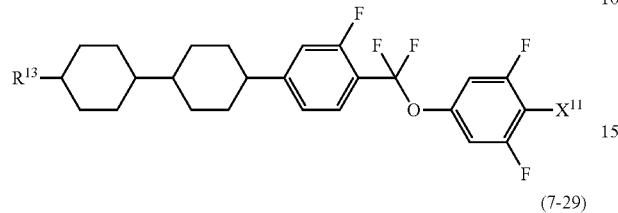
(7-29)
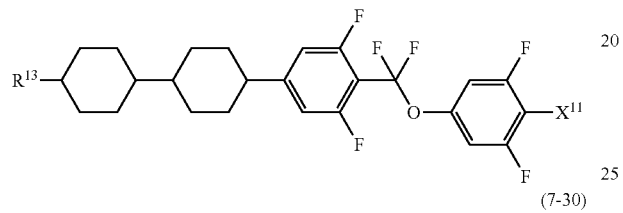
(7-30)
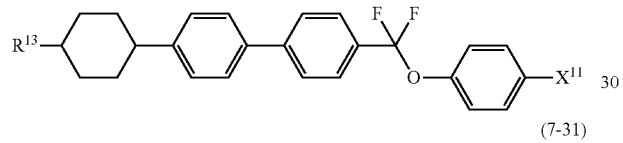
(7-31)
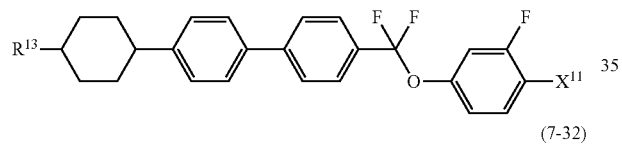
(7-32)
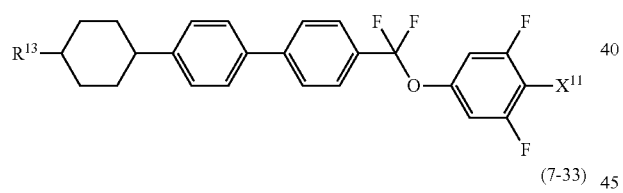
(7-33)
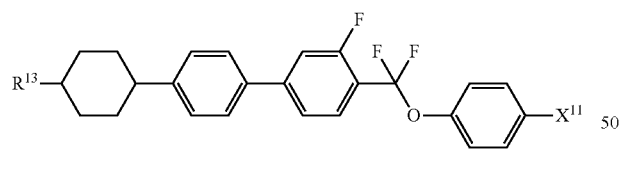
(7-34)
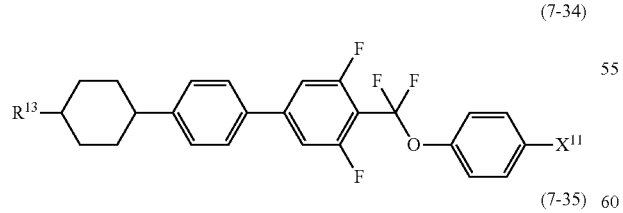
(7-35)
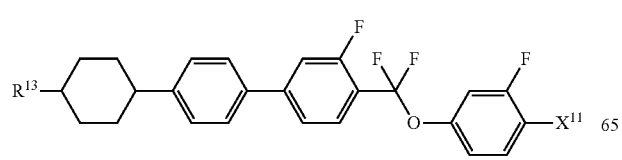
(7-36)
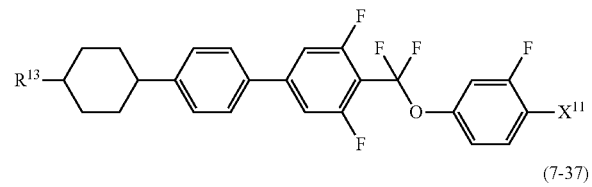
(7-37)
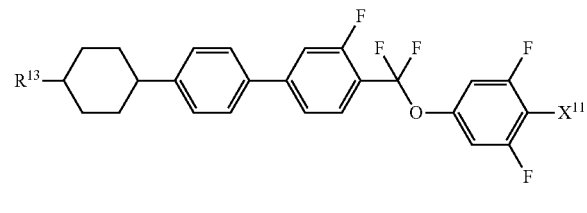
(7-38)
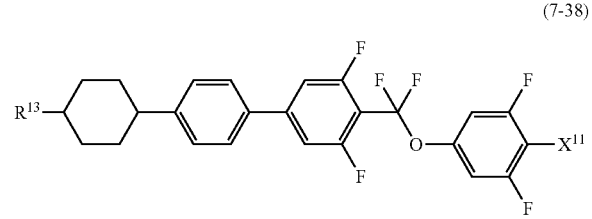
(7-39)
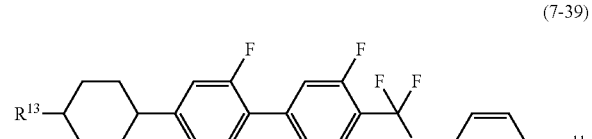
(7-40)
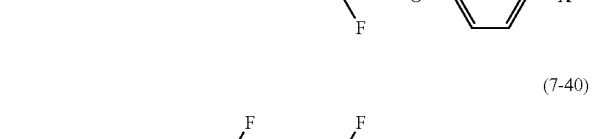
(7-41)
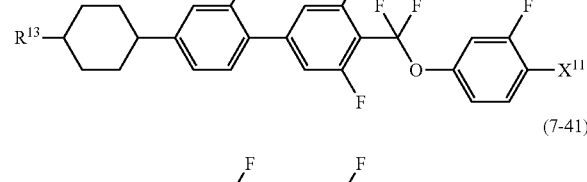
(7-42)
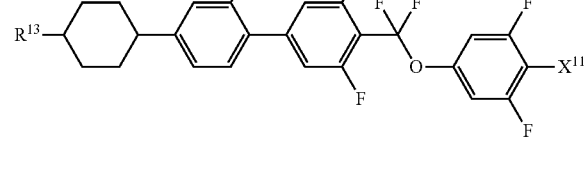
(7-43)
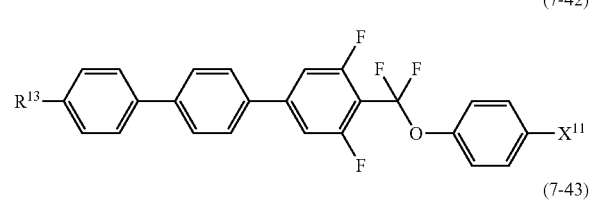
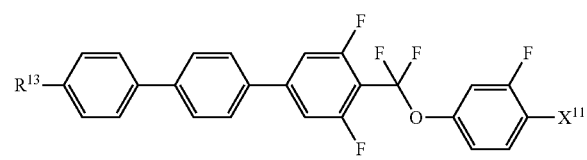

(7-44)
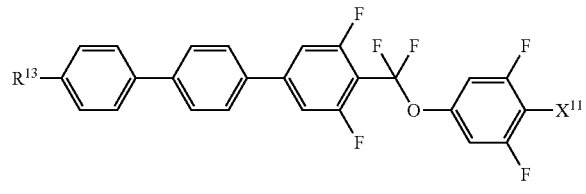

(7-45)
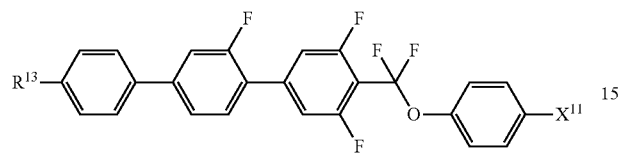

(7-46)
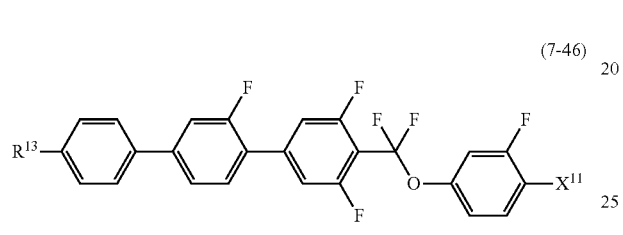

(7-47)
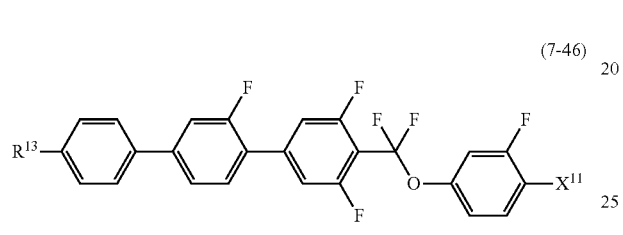

(7-48)
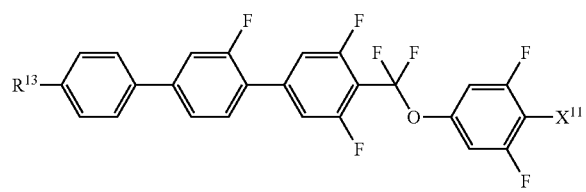

(7-49)
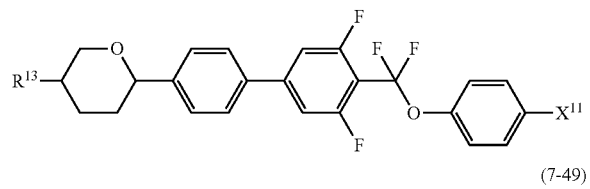

(7-50)
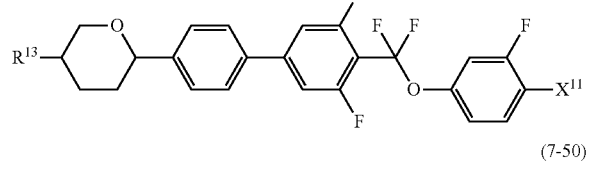

(7-51)
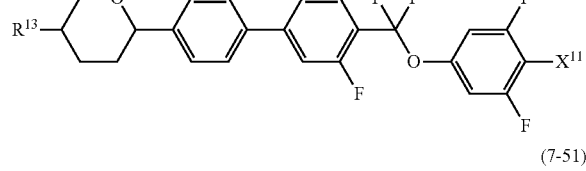

(7-52)
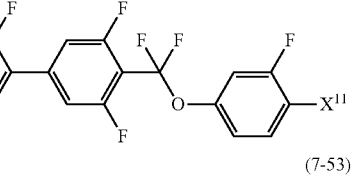

(7-53)
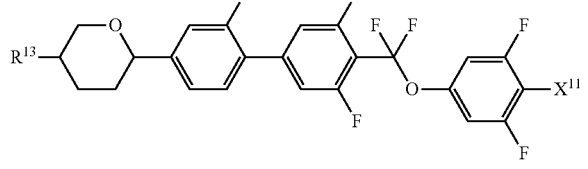

(7-54)
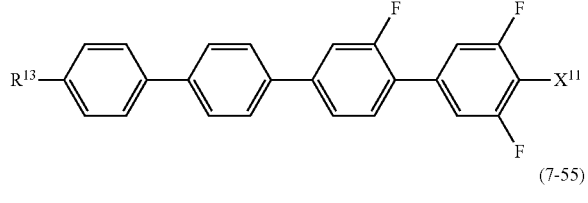

(7-55)
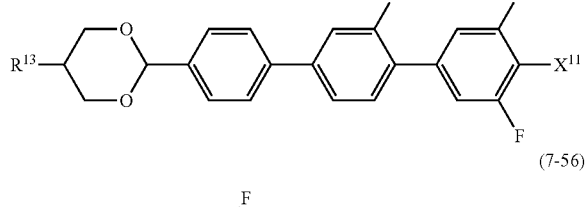

(7-56)
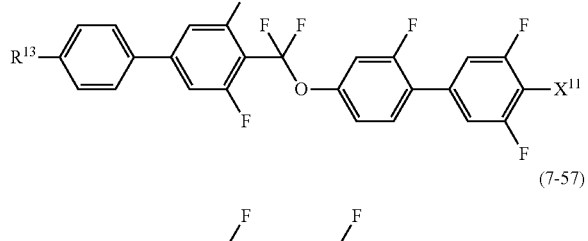

(7-57)
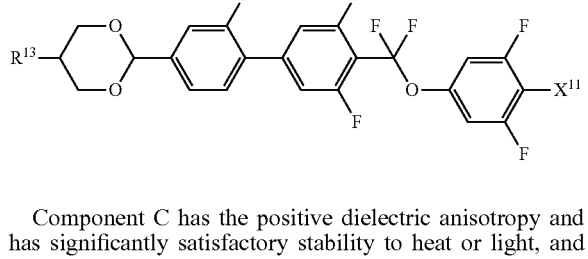

Component C has the positive dielectric anisotropy and has significantly satisfactory stability to heat or light, and therefore is used when a composition for the IPS mode, the FFS mode, and the OCB more and so forth is prepared. A content of component C is suitably in the range of about 1% by weight to about 99% by weight, preferably in the range of about 10% by weight to about 97% by weight, and further preferably in the range of about 40% by weight to about 95% by weight, based on the weight of the liquid crystal composition. When component C is added to the composition having the negative dielectric anisotropy, the content of component C is preferably about 30% by weight or less. Addition of component C allows adjustment of the elastic constant of the composition and adjustment of a voltage-transmittance curve of the device.

Component D is compound (8) in which a right-terminal group is —C≡N or —C≡C—C≡N. Specific examples of preferred component D include compounds (8-1) to (8-64). In the compounds, $R^{14}$ is alkyl having 1 to 10 carbons or alkenyl having 2 to 10 carbons, and in the alkyl and the alkenyl, at least one piece of —$CH_2$— may be replaced by —O—, and in the groups, at least one piece of hydrogen may be replaced by fluorine. $X^{12}$ is —C≡N or —C≡C—C≡N.
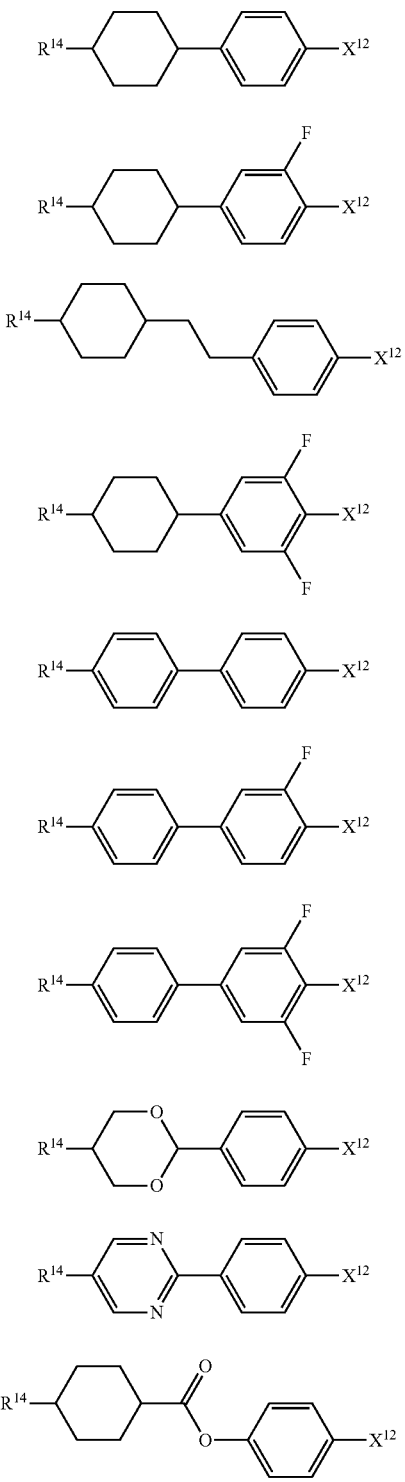
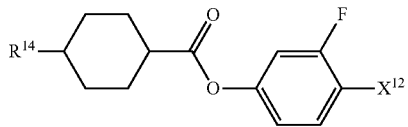
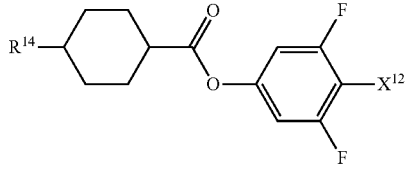
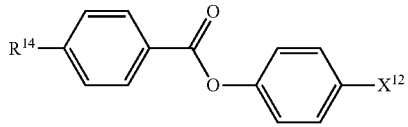
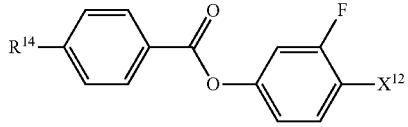
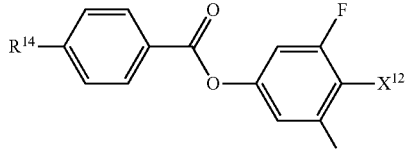
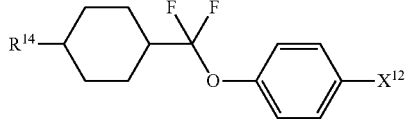
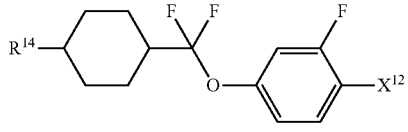
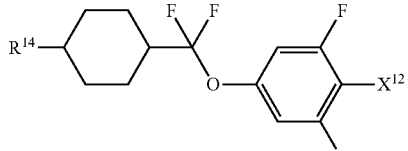
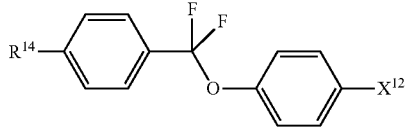
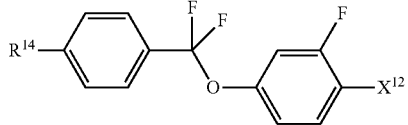

(8-21) 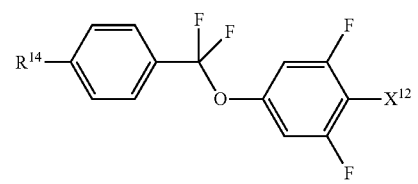
(8-22) 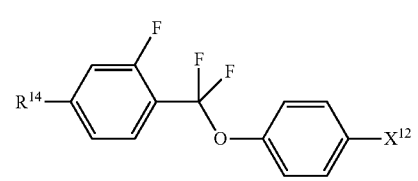
(8-23) 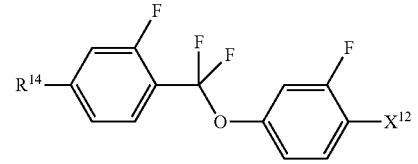
(8-24) 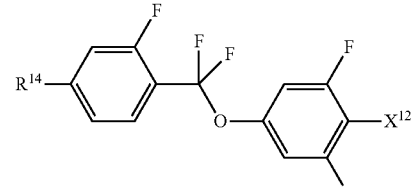
(8-25) 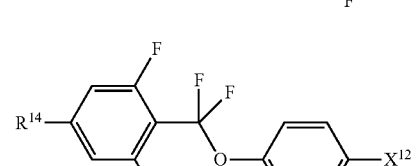
(8-26) 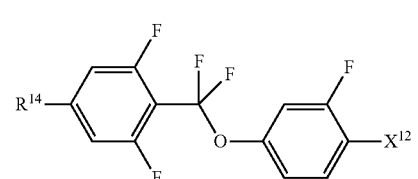
(8-27) 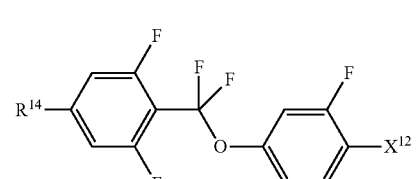
(8-28) 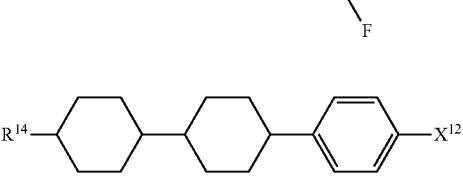
(8-29) 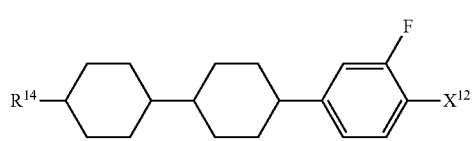
(8-30) 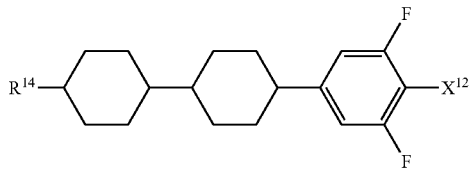
(8-31) 
(8-32) 
(8-33) 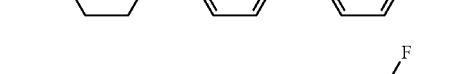
(8-34) 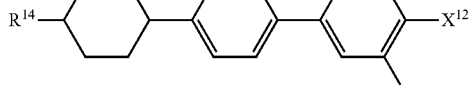
(8-35) 
(8-36) 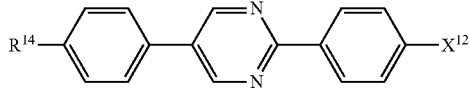
(8-37) 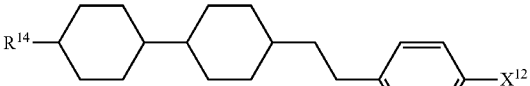
(8-38) 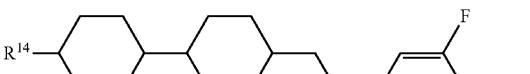
(8-39) 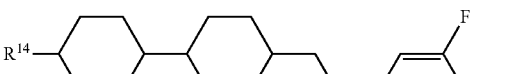
(8-40) 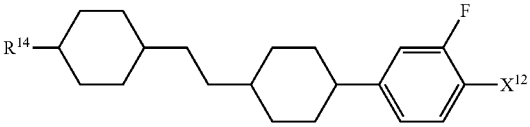

(8-41)
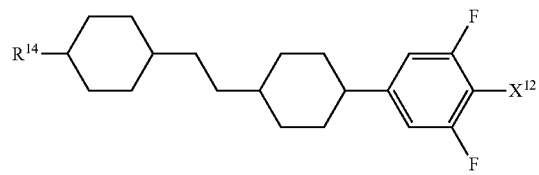
(8-42)
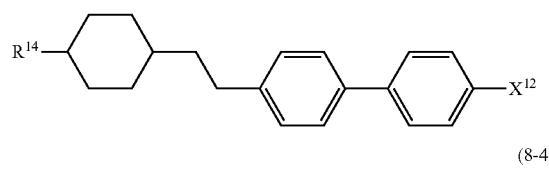
(8-43)
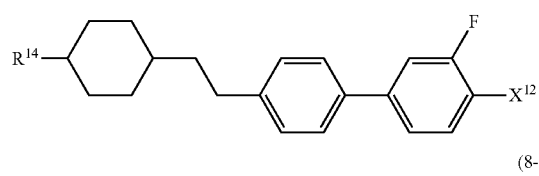
(8-44)
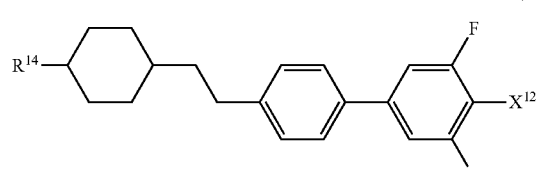
(8-45)
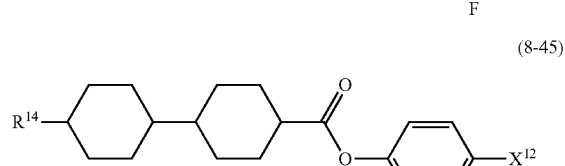
(8-46)
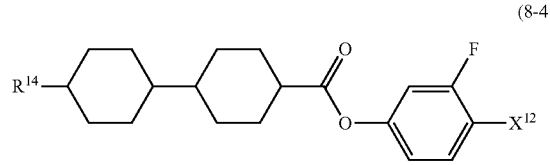
(8-47)
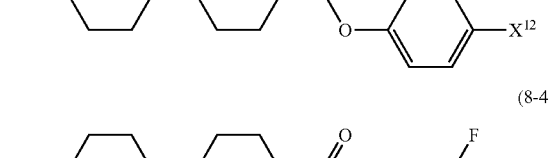
(8-48)
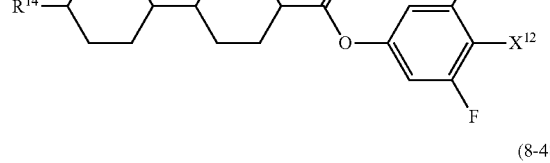
(8-49)
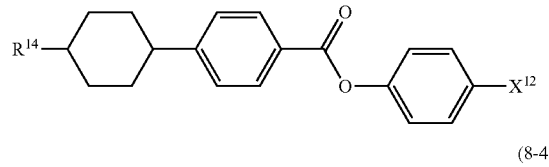
(8-50)
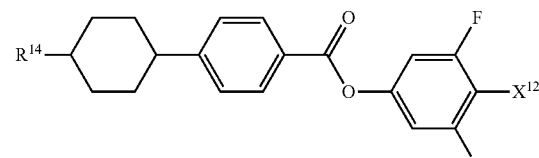
(8-51)
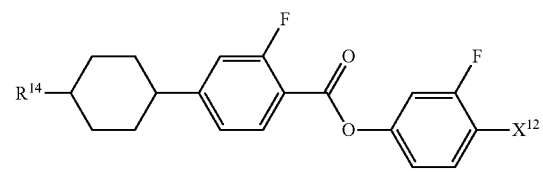
(8-52)
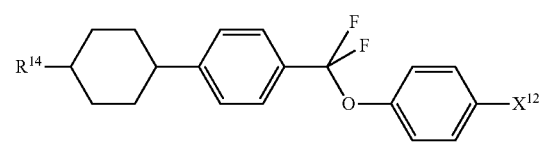
(8-53)
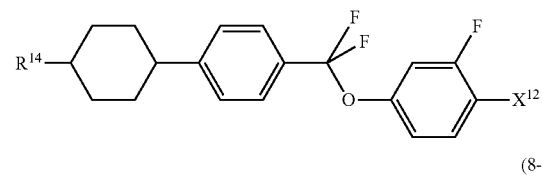
(8-54)
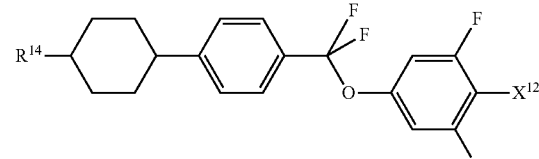
(8-55)
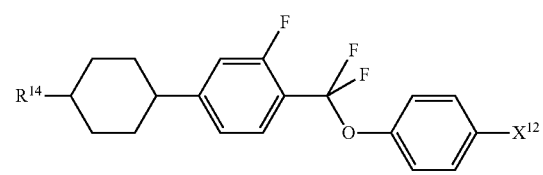
(8-56)
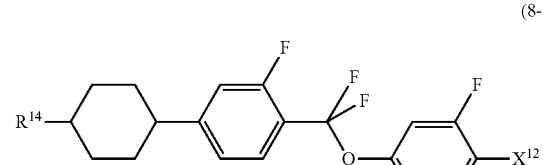
(8-57)
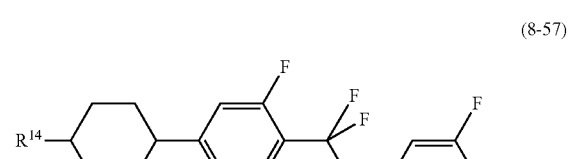

-continued

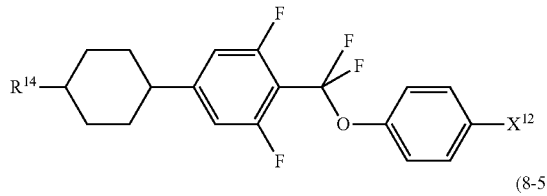
(8-58)

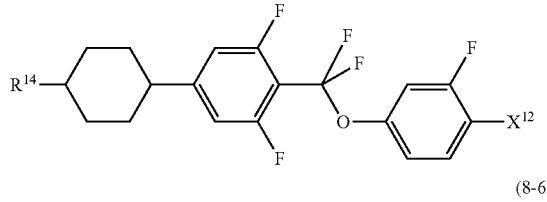
(8-59)

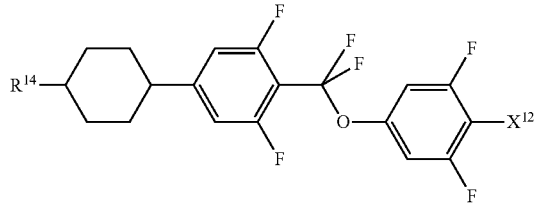
(8-60)

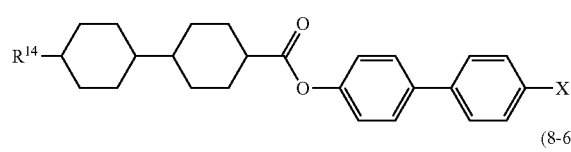
(8-61)

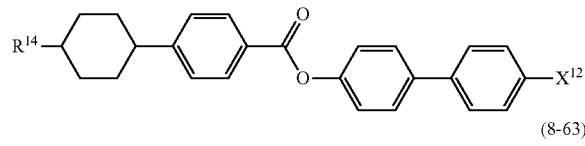
(8-62)

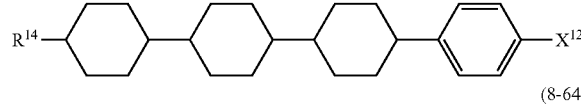
(8-63)

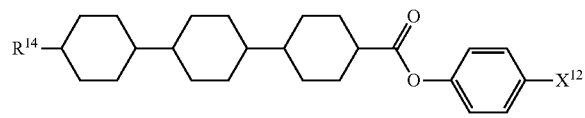
(8-64)

Component D has the positive dielectric anisotropy and a value thereof is large, and therefore is used when a composition for the TN mode or the like is prepared. Addition of component D can increase the dielectric anisotropy of the composition. Component D is effective in extending the temperature range of the liquid crystal phase, adjusting the viscosity or adjusting the optical anisotropy. Component D is also useful for adjustment of the voltage-transmittance curve of the device.

When the composition for the TN mode or the like is prepared, a content of component D is suitably in the range of about 1% by weight to about 99% by weight, preferably in the range of about 10% by weight to about 97% by weight, and further preferably in the range of about 40% by weight to about 95% by weight, based on the weight of the liquid crystal composition. When component D is added to the composition having the negative dielectric anisotropy, a content of component D is preferably about 30% by weight or less. Addition of component D allows adjustment of the elastic constant of the composition and adjustment of the voltage-transmittance curve of the device.

Component E includes compounds (9) to (15). The compounds have phenylene in which hydrogen in lateral positions are replaced by two pieces of halogen, such as 2,3-difluoro-1,4-phenylene. Specific examples of preferred component E include compounds (9-1) to (9-8), compounds (10-1) to (10-17), compound (11-1), compounds (12-1) to (12-3), compounds (13-1) to (13-11), compounds (14-1) to (14-3) and compounds (15-1) to (15-3). In the compounds, $R^{15}$, $R^{16}$ and $R^{17}$ are independently alkyl having 1 to 10 carbons or alkenyl having 2 to 10 carbons, and in the alkyl and the alkenyl, at least one piece of —$CH_2$— may be replaced by —O—, and in the groups, at least one piece of hydrogen may be replaced by fluorine, and $R^{17}$ may be hydrogen or fluorine.

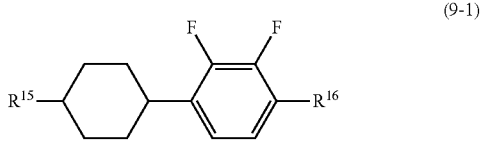
(9-1)

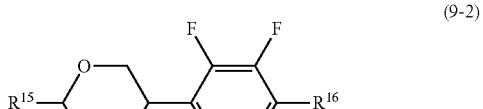
(9-2)

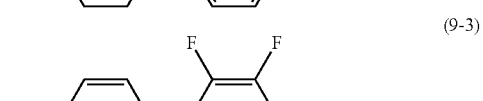
(9-3)

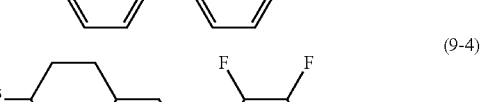
(9-4)

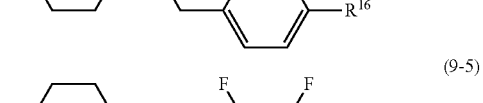
(9-5)

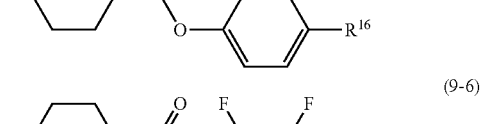
(9-6)

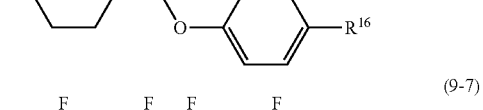
(9-7)

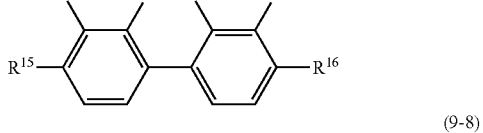
(9-8)

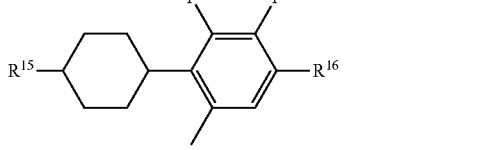

(10-1) 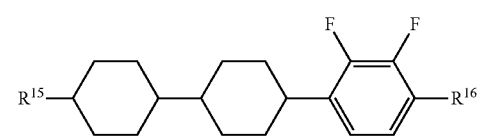
(10-2) 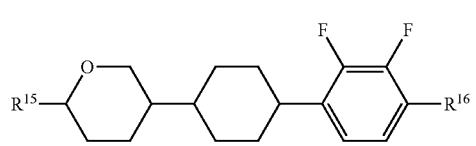
(10-3) 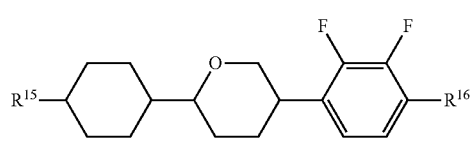
(10-4) 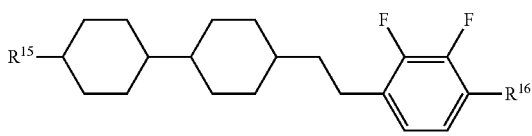
(10-5) 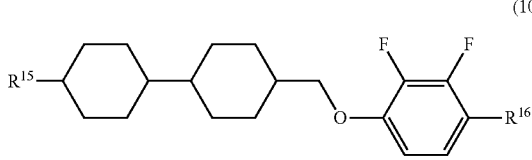
(10-6) 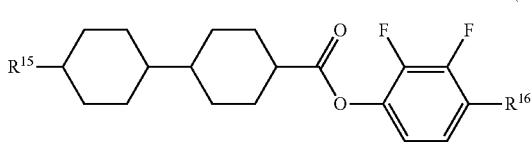
(10-7) 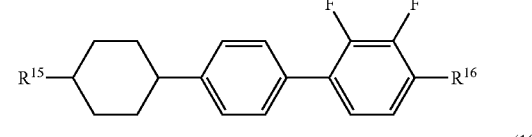
(10-8) 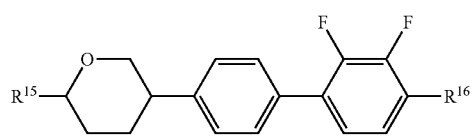
(10-9) 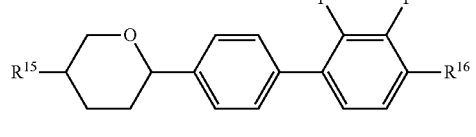
(10-10) 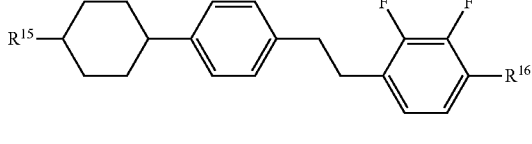
(10-11) 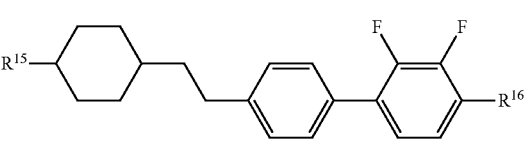
(10-12) 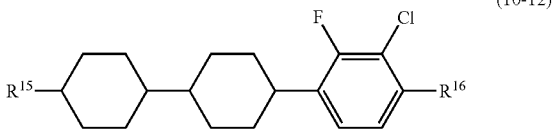
(10-13) 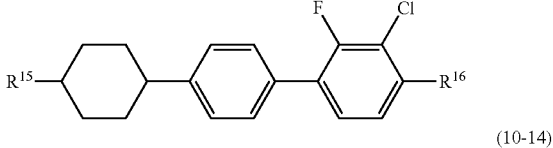
(10-14) 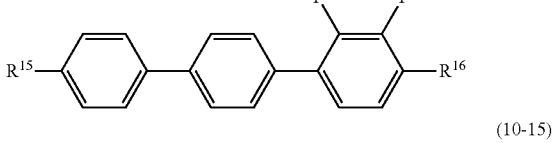
(10-15) 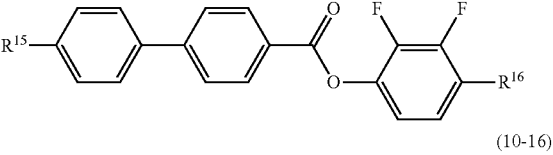
(10-16) 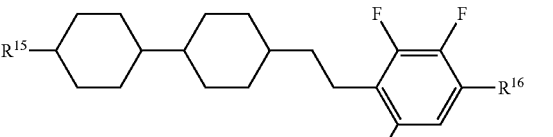
(10-17) 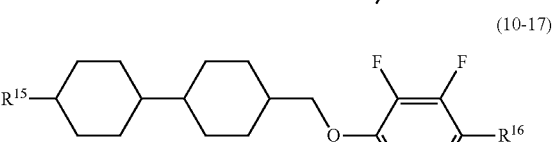
(11-1) 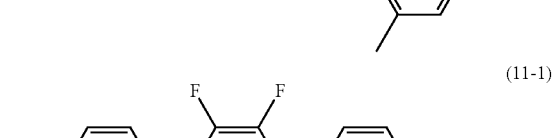
(12-1) 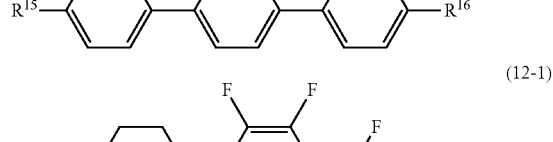
(12-2) 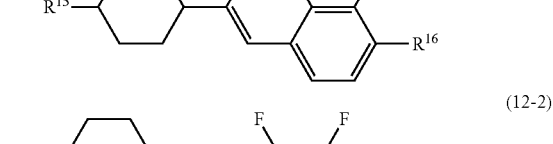

(12-3) 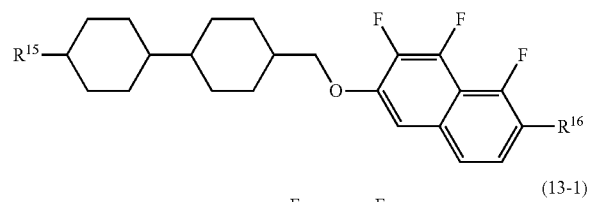
(13-1) 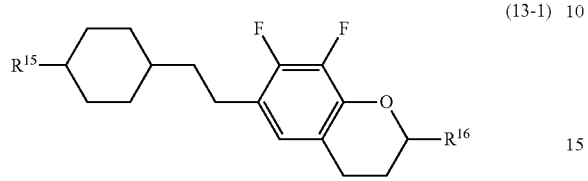
(13-2) 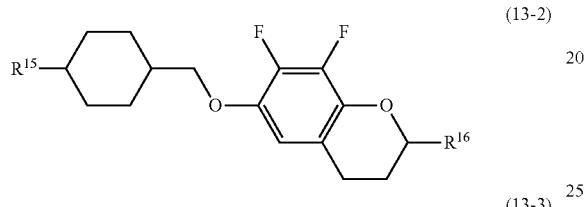
(13-3) 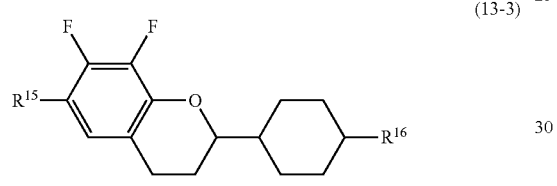
(13-4) 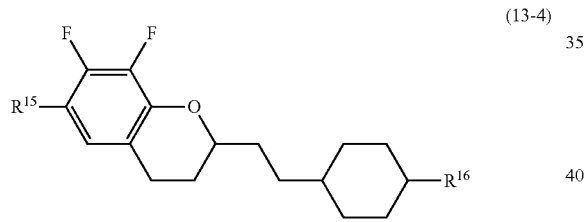
(13-5) 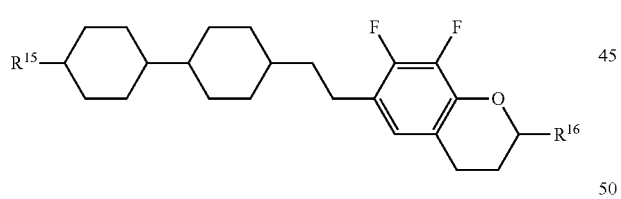
(13-6) 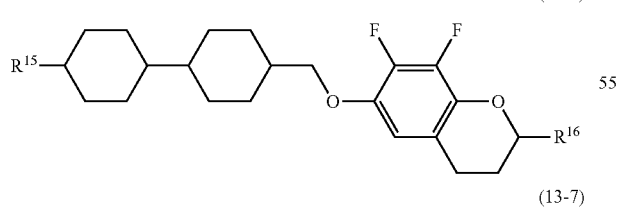
(13-7) 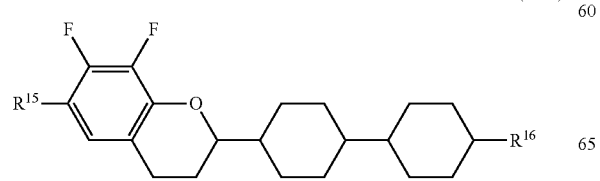
(13-8) 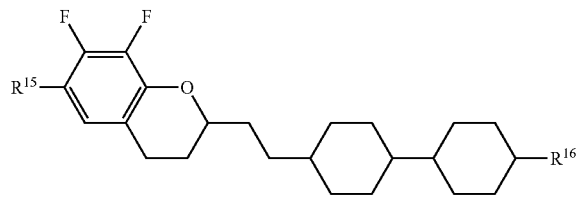
(13-9) 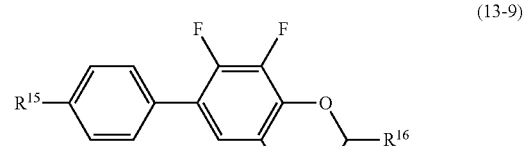
(13-10) 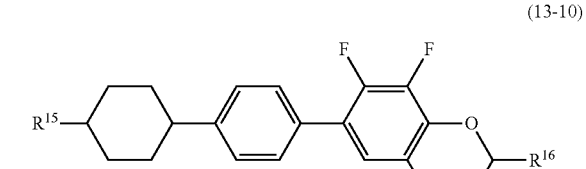
(13-11) 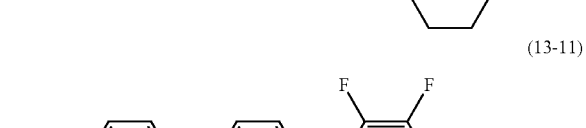
(14-1) 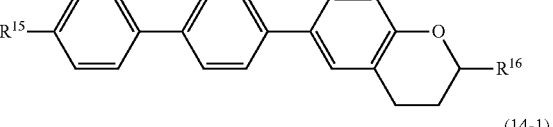
(14-2) 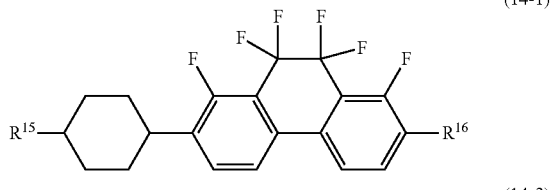
(14-3) 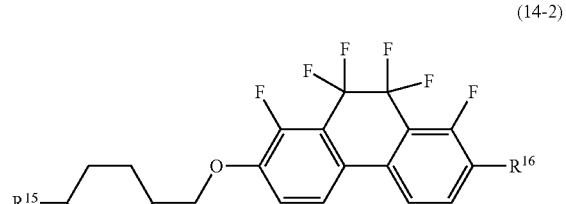
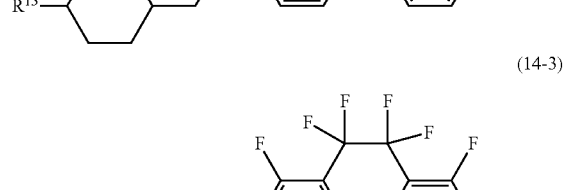
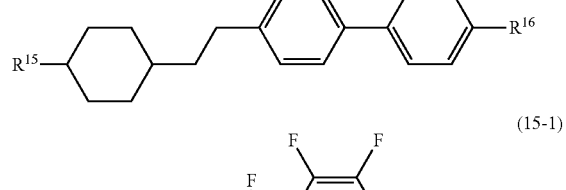
(15-1) 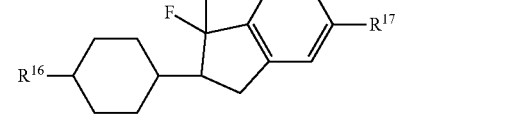

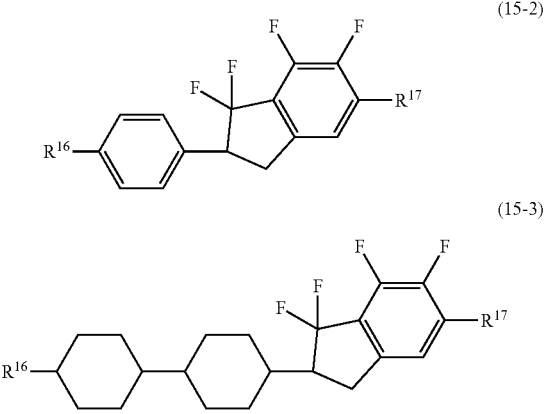

(15-2)

(15-3)

Component E has the negatively large dielectric anisotropy. Component E is used when the composition for the IPS mode, the VA mode, the PSA mode or the like is prepared. As a content of component E is increased, the dielectric anisotropy of the composition is negatively increased, and the viscosity is increased. Thus, as long as a desired value of threshold voltage of the device is met, the content is preferably as small as possible. When the dielectric anisotropy at a degree of −5 is taken into account, the content is preferably about 40% by weight or more in order to allow a sufficient voltage driving.

Among types of component E, compound (9) is a bicyclic compound, and therefore is effective in decreasing the viscosity, adjusting the optical anisotropy, or increasing the dielectric anisotropy. Compounds (10) and (11) are a tricyclic compound, and therefore are effective in increasing the maximum temperature, the optical anisotropy or the dielectric anisotropy. Compounds (12) to (15) are effective in increasing the dielectric anisotropy.

When the composition for the IPS mode, the VA mode or the PSA mode and so forth is prepared, the content of component E is preferably about 40% by weight or more, and further preferably in the range of about 50% by weight to about 95% by weight, based on the weight of the liquid crystal composition. When component E is added to the composition having the positive dielectric anisotropy, the content of component E is preferably about 30% by weight or less. Addition of component E allows adjustment of the elastic constant of the composition and adjustment of the voltage-transmittance curve of the device.

The liquid crystal composition satisfying at least one of physical properties such as the high stability to heat and light, the high maximum temperature, the low minimum temperature, the small viscosity, the suitable optical anisotropy (namely, the large optical anisotropy or the small optical anisotropy), the large positive or negative dielectric anisotropy, the large specific resistance, and the suitable elastic constant (namely, the large elastic constant or the small elastic constant) can be prepared by suitably combining compound (1) with components B, C, D and E. The device including such a composition has a wide temperature range in which the device can be used, a short response time, the large voltage holding ratio, a low threshold voltage, a large contrast ratio, a small flicker rate and a long service life.

When the device is used for a long period of time, a flicker may be occasionally generated on a display screen. A flicker rate (%) can be represented by (|brightness when positive voltage is applied−brightness when negative voltage is applied|)/average brightness)×100. In the device having the flicker rate in the range of about 0% to about 1%, the flicker is hard to generate on the display screen even if the device is used for a long period of time. The flicker is assumed to be related to image persistence, and caused by a difference in potential between a positive frame and a negative frame upon driving the device by alternating current. The composition containing compound (1) is useful also for decreasing generation of the flicker.

3-2. Additive

A liquid crystal composition is prepared according to a known method. For example, the component compounds are mixed and dissolved in each other by heating. According to an application, an additive may be added to the composition. Specific examples of the additive include a polymerizable compound, a polymerization initiator, a polymerization inhibitor, an optically active compound, an antioxidant, an ultraviolet light absorber, a light stabilizer excluding the compound represented by formula (1), a heat stabilizer, a dye and an antifoaming agent. Such additives are well known to those skilled in the art, and described in literature.

In the liquid crystal display device having the PSA (polymer sustained alignment) mode, the composition contains a polymer. The polymerizable compound is added for the purpose of forming the polymer in the composition. The polymerizable compound is polymerized by irradiation with ultraviolet light while voltage is applied between electrodes, and thus the polymer is formed in the composition. A suitable pretilt is achieved by the method, and therefore the device in which the response time is shortened and the image persistence is improved is prepared.

Specific examples of a preferred polymerizable compound include acrylate, methacrylate, a vinyl compound, a vinyloxy compound, propenyl ether, an epoxy compound (oxirane, oxetane) and vinyl ketone. Further preferred examples include a compound having at least one acryloyloxy, and a compound having at least one piece of methacryloyloxy. Still further preferred examples also include a compound having both acryloyloxy and methacryloyloxy.

Still further preferred examples include compounds (M-1) to (M-18). In the compounds, $R^{25}$ to $R^{31}$ is independently hydrogen or methyl; $R^{32}$, $R^{33}$ and $R^{34}$ are independently hydrogen or alkyl having 1 to 5 carbons, and at least one piece of $R^{32}$, $R^{33}$ and $R^{34}$ is alkyl having 1 to 5 carbons; v, w and x are independently 0 or 1; and u and y are independently an integer from 1 to 10. $L^{21}$ to $L^{26}$ are independently hydrogen or fluorine; and $L^{27}$ and $L^{28}$ are independently hydrogen, fluorine or methyl.

(M-1)

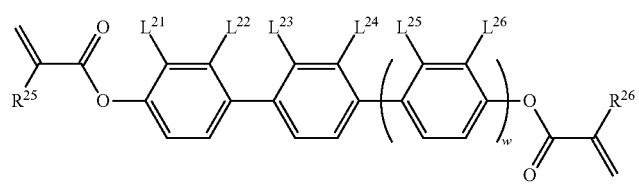

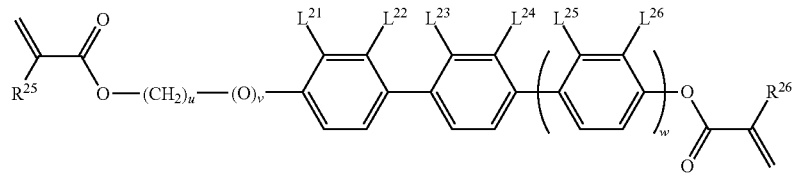
(M-2)
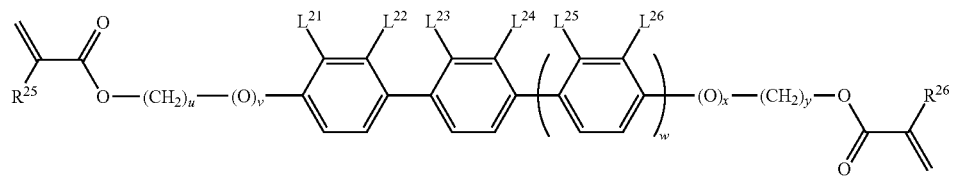
(M-3)
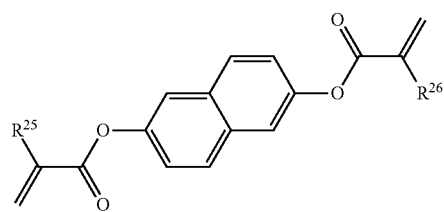
(M-4)
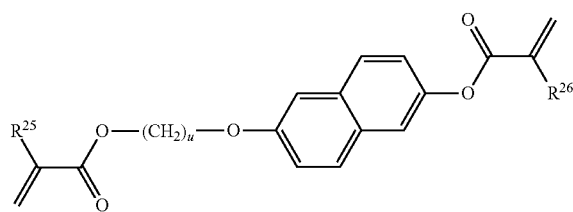
(M-5)
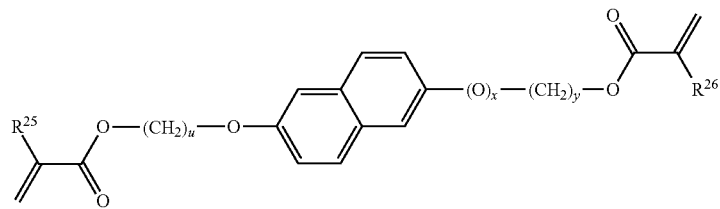
(M-6)
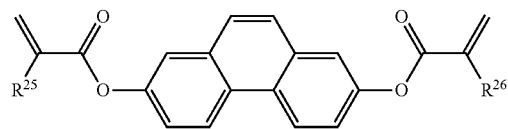
(M-7)
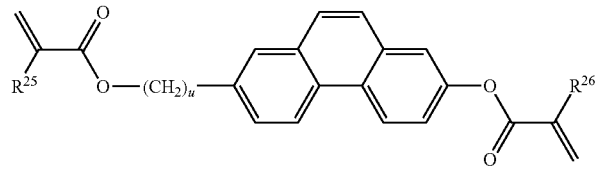
(M-8)
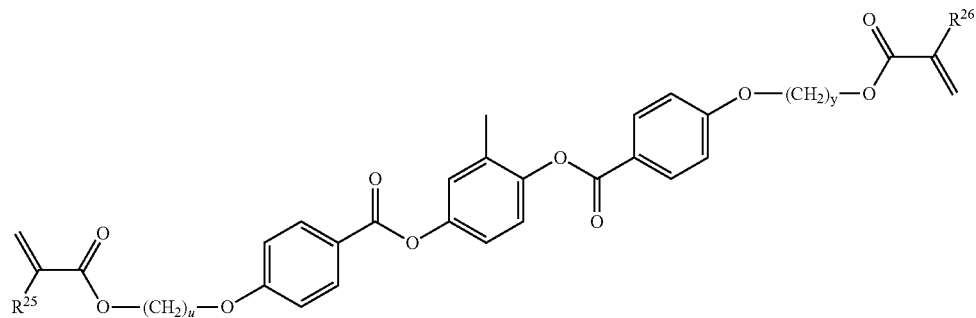
(M-9)

-continued
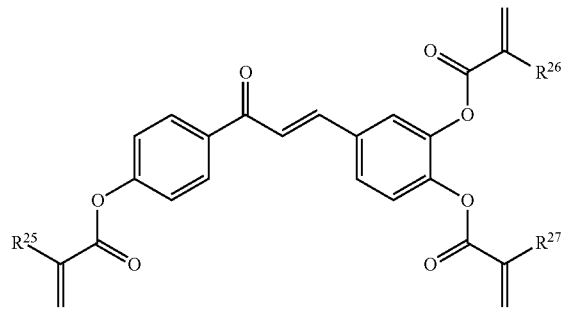 (M-10)
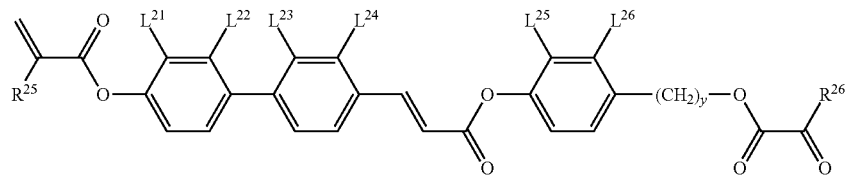 (M-11)
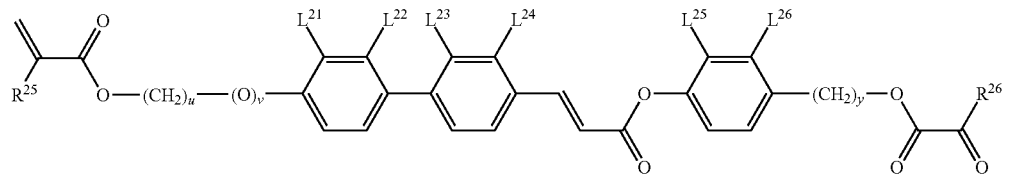 (M-12)
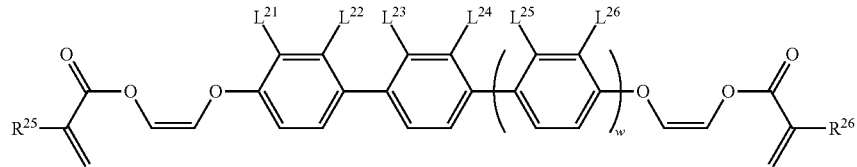 (M-13)
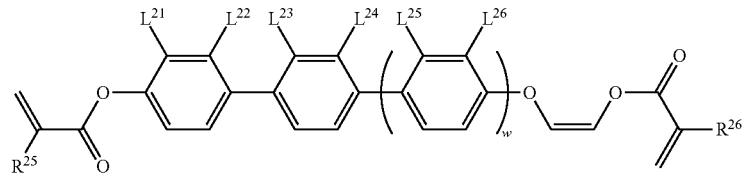 (M-14)
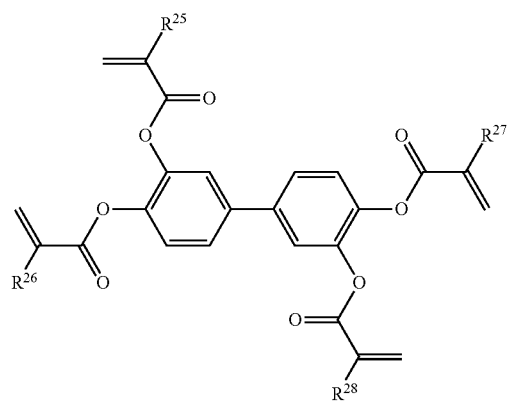 (M-15)

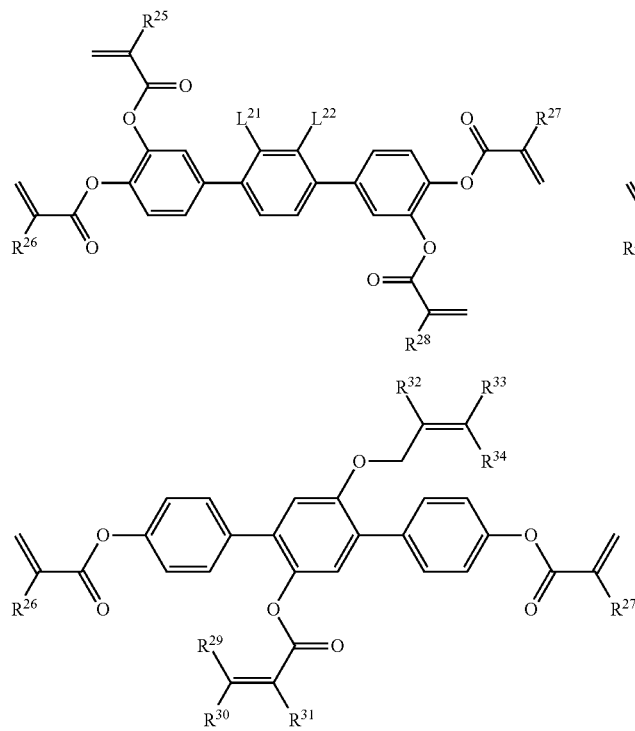

(M-16)

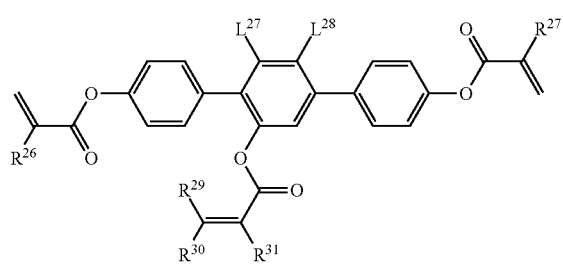

(M-17)

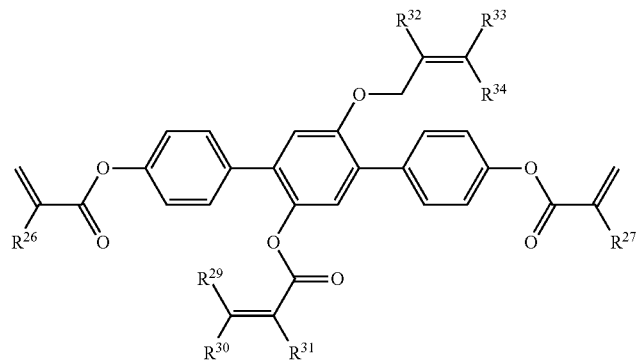

(M-18)

The polymerizable compound can be rapidly polymerized by adding the polymerization initiator. An amount of the residual polymerizable compound can be decreased by optimizing reaction conditions. Specific examples of a photoradical polymerization initiator include TPO, 1173 and 4265 from Darocur series of BASF SE, and 184, 369, 500, 651, 784, 819, 907, 1300, 1700, 1800, 1850 and 2959 from Irgacure series thereof.

Additional examples of the photoradical polymerization initiator include 4-methoxyphenyl-2,4-bis(trichloromethyl) triazine, 2-(4-butoxystyryl)-5-trichloromethyl-1,3,4-oxadiazole, 9-phenylacridine, 9,10-benzphenazine, a benzophenone-Michler's ketone mixture, a hexaarylbiimidazole-mercaptobenzimidazole mixture, 1-(4-isopropylphenyl)-2-hydroxy-2-methylpropane-1-one, benzyl dimethyl ketal, 2-methyl-1-[4-(methylthio)phenyl]-2-morpholinopropane-1-one, a mixture of 2,4-diethylxanthone and methyl p-dimethylaminobenzoate, and a mixture of benzophenone and methyltriethanolamine.

After the photoradical polymerization initiator is added to the liquid crystal composition, polymerization can be performed by irradiation with ultraviolet light while an electric field is applied. However, an unreacted polymerization initiator or a decomposition product of the polymerization initiator may cause a poor display such as the image persistence in the device. In order to prevent such an event, photopolymerization may be performed without addition of the polymerization initiator. A preferred wavelength of irradiation light is in the range of about 150 nanometers to about 500 nanometers. A further preferred wavelength is in the range of about 250 nanometers to about 450 nanometers, and a most preferred wavelength is in the range of about 300 nanometers to about 400 nanometers.

Upon storing the polymerizable compound, the polymerization inhibitor may be added thereto for preventing polymerization. The polymerizable compound is ordinarily added to the composition without removing the polymerization inhibitor. Specific examples of the polymerization inhibitor include hydroquinone, a hydroquinone derivative such as methylhydroquinone, 4-t-butyl-catechol, 4-methoxyphenol and phenothiazine.

The optically active compound is effective in inducing a helical structure in liquid crystal molecules to give a required twist angle, thereby preventing a reverse twist. A helical pitch can be adjusted by adding the optically active compound thereto. Two or more optically active compounds may be added for the purpose of adjusting temperature dependence of the helical pitch. Specific examples of a preferred optically active compound include compounds (Op-1) to (Op-18) described below. In compound (Op-18), ring J is 1,4-cyclohexylene or 1,4-phenylene, and $R^{28}$ is alkyl having 1 to 10 carbons. "*" mark represents an asymmetrical carbon.

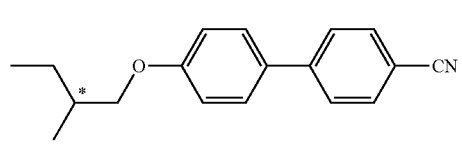

(Op-1)

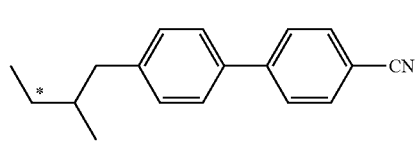

(Op-2)

(Op-3)
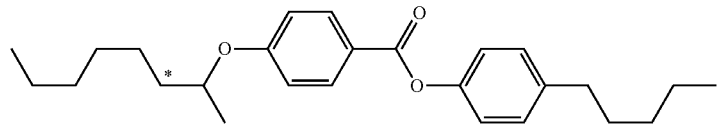
(Op-4)
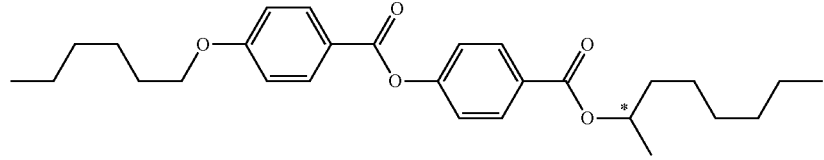
(Op-5)
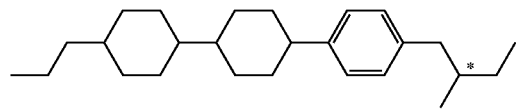
(Op-6)
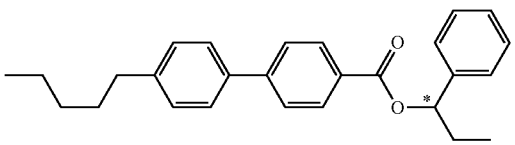
(Op-7)
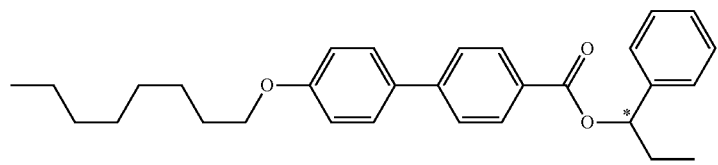
(Op-8)
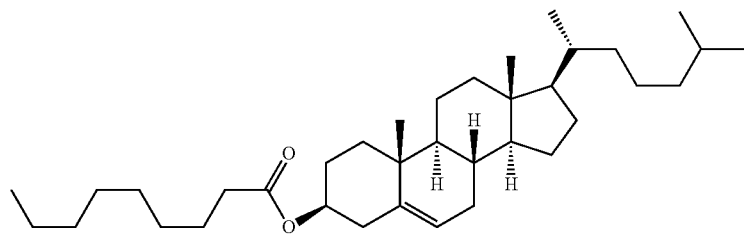
(Op-9)
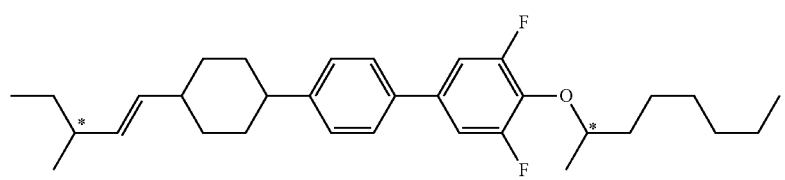
(Op-10)
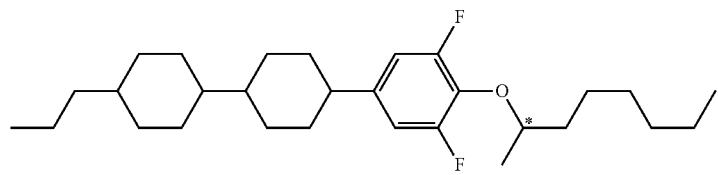
(Op-11)
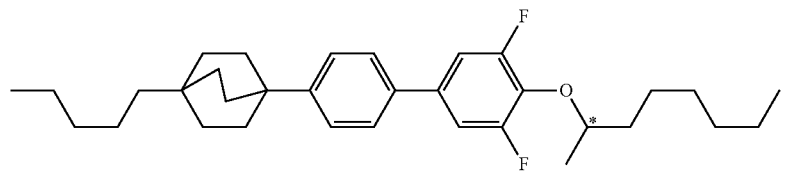
(Op-12)
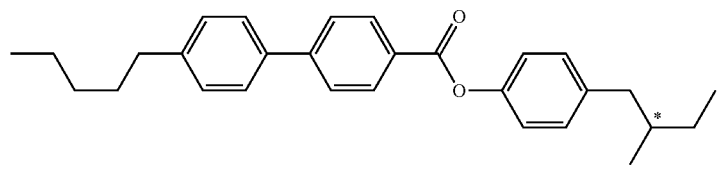

(Op-13)

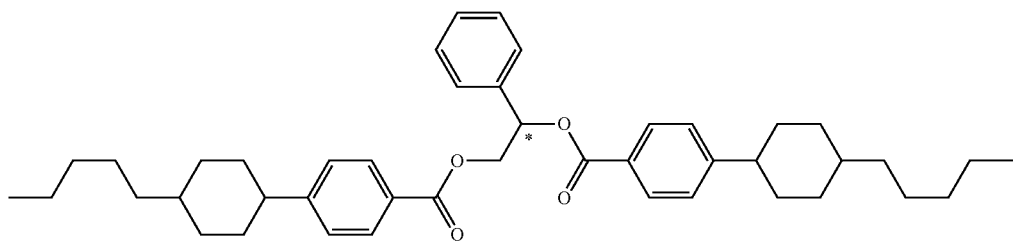

(Op-14)

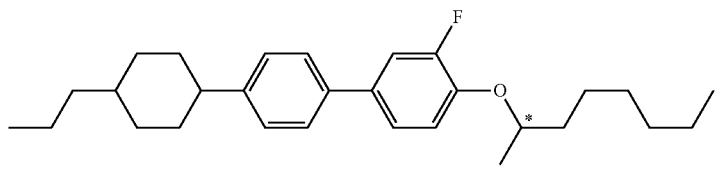

(Op-15)

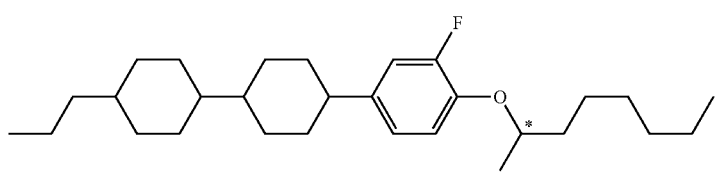

(OP-16)

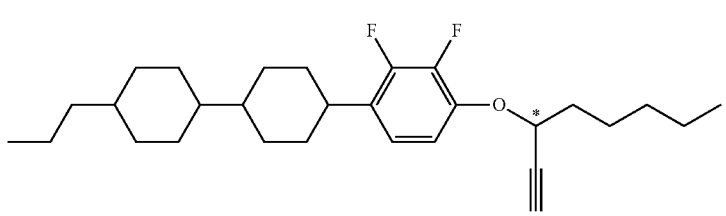

(Op-17)

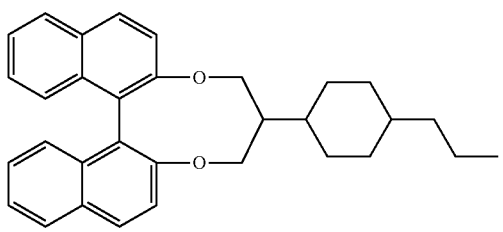

(Op-18)

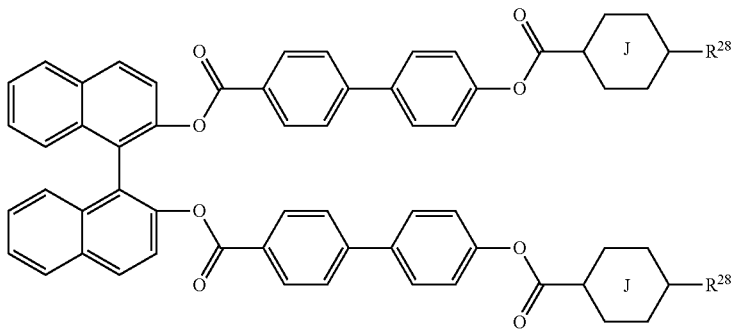

The antioxidant is effective for maintaining the large voltage holding ratio. Specific examples of a preferred antioxidant include compounds (AO-1) and (AO-2) described below; Irganox 415, Irganox 565, Irganox 1010, Irganox 1035, Irganox 3114 and Irganox 1098 (tradenames; BASF SE). The ultraviolet light absorber is effective for preventing a decrease in the maximum temperature. Specific examples of a preferred ultraviolet light absorbent include a benzophenone derivative, a benzoate derivative, and a triazole derivative, and specific examples thereof include compounds (AO-3) and (AO-4) described below; Tinuvin 329, Tinuvin P, Tinuvin 326, Tinuvin 234, Tinuvin 213, Tinuvin 400, Tinuvin 328 and Tinuvin 99-2 (tradenames; BASF SE); and 1,4-diazabicyclo[2.2.2]octane (DABCO).

The light stabilizer such as an amine having steric hindrance is preferred for maintaining the large voltage holding ratio. Specific examples of a preferred light stabilizer include compounds (AO-5), (AO-6) and (AO-7) described below; Tinuvin 144, Tinuvin 765, Tinuvin 770DF (tradenames; BASF SE); and LA-77Y and LA-77G (tradenames; ADEKA). The heat stabilizer is also effective for maintaining the large voltage holding ratio, and preferred examples thereof include Irgafos 168 (tradename; BASF SE). A dichroic dye such as an azo dye or an anthraquinone dye is added to the composition for adaption to a device having a guest host (GH) mode. The antifoaming agent is effective for preventing foam formation. Specific examples of a preferred antifoaming agent include dimethyl silicone oil and methylphenyl silicone oil.

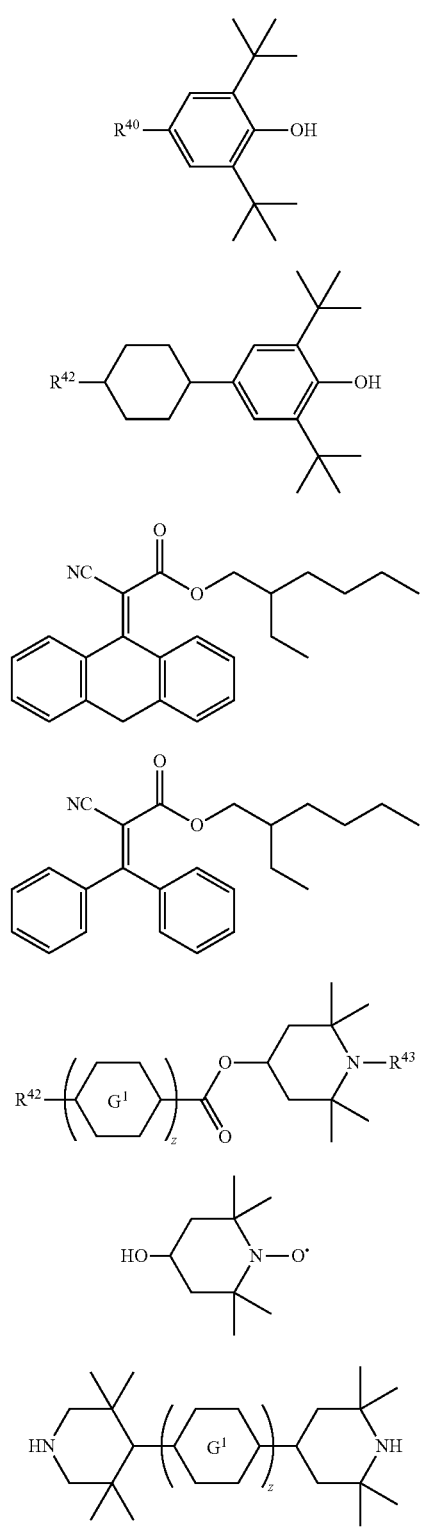

In compound (AO-1), $R^{40}$ is alkyl having 1 to 20 carbons, alkoxy having 1 to 20 carbons, —COOR$^{41}$ or —CH$_2$CH$_2$COOR$^{41}$, where, $R^{41}$ is alkyl having 1 to 20 carbons. In compounds (AO-2) and (AO-5), $R^{42}$ is alkyl having 1 to 20 carbons. In compound (AO-5), $R^{43}$ is hydrogen, methyl or O. (oxygen radical); ring $G^1$ is 1,4-cyclohexylene or 1,4-phenylene; in compound (AO-7), ring $G^2$ is 1,4-cyclohexylene, 1,4-phenylene, or 1,4-phenylene in which at least one piece of hydrogen is replaced by fluorine; and in compounds (AO-5) and (AO-7), z is 1, 2 or 3.

4. Liquid Crystal Display Device

The liquid crystal composition can be used for the liquid crystal device having the operating modes such as the PC mode, the TN mode, the STN mode, the OCB mode and the PSA mode, and driven by an active matrix mode. The composition can also be used for the liquid crystal display device having the operating mode such as the PC mode, the TN mode, the STN mode, the OCB mode, the VA mode and the IPS mode, and driven by a passive matrix mode. The devices can be applied to any of a reflective type, a transmissive type and a transflective type.

The composition is also suitable for a nematic curvilinear aligned phase (NCAP) device, and the composition is microencapsulated in the device. The composition can also be used for a polymer dispersed liquid crystal display device (PDLCD) and a polymer network liquid crystal display device (PNLCD). In the compositions, a large amount of the polymerizable compound is added. Meanwhile, when a proportion of the polymerizable compound is 10% by weight or less based on the weight of the liquid crystal composition, the liquid crystal display device having the PSA mode is made. A preferred proportion is in the range of about 0.1% by weight to about 2% by weight. A further preferred proportion is in the range of about 0.2% by weight to about 1.0% by weight. The device having the PSA mode can be driven by the driving mode such as the active matrix mode or the passive-matrix mode. Such devices can be applied to any of the reflective type, the transmissive type and the transflective type.

EXAMPLES

1. Example of Compound (1)

The invention will be described in greater detail by way of Examples. Example is described as a typical example, and therefore the invention is not limited thereby. Compound (1) was prepared according to procedures described below. The thus prepared compound was identified by methods such as an NMR analysis. Physical properties of the compound and the composition and characteristics of a device were measured by methods described below.

NMR analysis: For measurement, DRX-500 made by Bruker BioSpin Corporation was used. In $^1$H-NMR measurement, a sample was dissolved in a deuterated solvent such as CDCl$_3$, and measurement was carried out under conditions of room temperature, 500 MHz and 16 times of accumulation. Tetramethylsilane was used as an internal standard. In $^{19}$F-NMR measurement, CFCl$_3$ was used as an internal standard, and measurement was carried out under conditions of 24 times of accumulation. In explaining nuclear magnetic resonance spectra obtained, s, d, t, q, quin, sex and m stand for a singlet, a doublet, a triplet, a quartet, a quintet, a sextet and a multiplet, and br being broad, respectively.

Gas chromatographic analysis: For measurement, GC-2010 Gas Chromatograph made by Shimadzu Corporation was used. As a column, a capillary column DB-1 (length 60 m, bore 0.25 mm, film thickness 0.25 μm) made by Agilent Technologies, Inc. was used. As a carrier gas, helium (1 mL/minute) was used. A temperature of a sample vaporizing chamber was set to 300° C., and a temperature of a detector (FID) was set to 300° C. A sample was dissolved in acetone and prepared to be a 1 wt % solution, and then 1 microliter of the solution obtained was injected into the sample vaporizing chamber. As a recorder, GC Solution System made by Shimadzu Corporation or the like was used.

HPLC Analysis: For measurement, Prominence (LC-20AD; SPD-20A) made by Shimadzu Corporation was used. As a column, YMC-Pack ODS-A (length 150 mm, bore 4.6 mm, particle diameter 5 μm) made by YMC Co., Ltd. was used. As an eluate, acetonitrile and water were appropriately mixed and used. As a detector, a UV detector, an RI detector, a CORONA detector or the like was appropriately used. When the UV detector was used, a detection wavelength was set at 254 nanometers. A sample was dissolved in acetonitrile and prepared to be a 0.1 weight solution, and then 1 microliter of the solution was introduced into a sample chamber. As a recorder, C-R7Aplus made by Shimadzu Corporation was used.

Ultraviolet-Visible Spectrophotometry: For measurement, PharmaSpec UV-1700 made by Shimadzu Corporation was used. A detection wavelength was adjusted in the range of about 190 nanometers to about 700 nanometers. A sample was dissolved in acetonitrile, and prepared to be a solution of 0.01 mmol per liter, and measurement was carried out by putting the solution in a quartz cell (optical path length 1 cm).

Sample for measurement: Upon measuring a phase structure and a transition temperature (a clearing point, a melting point, a polymerization starting temperature or the like), a compound itself was used as a sample. Upon measuring physical properties such as a maximum temperature of a nematic phase, viscosity, optical anisotropy and dielectric anisotropy, a mixture of a compound and a base liquid crystal was used as a sample.

An extrapolation method: when a sample obtained by mixing the compound with a base liquid crystal was used, measurement was carried out as follows. The sample was prepared by mixing 15% by weight of the compound and 85% by weight of the base liquid crystal. From a measured value of the sample, an extrapolated value was calculated according to the following equation, and the value was described: (Extrapolated value)={100×(measured value of a sample)−(% by weight of a base liquid crystal)×(measured value of a base liquid crystal)}/(% by weight of the compound).

When a crystal (or smectic phase) precipitated at the proportion at 25° C., a proportion of the compound to the base liquid crystal was changed in order of (10% by weight: 90% by weight), (5% by weight:95% by weight), and (1% by weight:99% by weight), and physical properties of the sample were measured at a proportion in which no crystal (or no smectic phase) precipitated at 25° C. In addition, unless otherwise noted, the proportion of the compound to the base liquid crystal was (15% by weight:85% by weight).

When the dielectric anisotropy of the compound was zero or positive, the following base liquid crystal (A) was used. A proportion of each component was expressed in terms of % by weight.

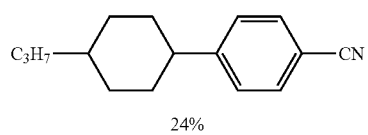

24%

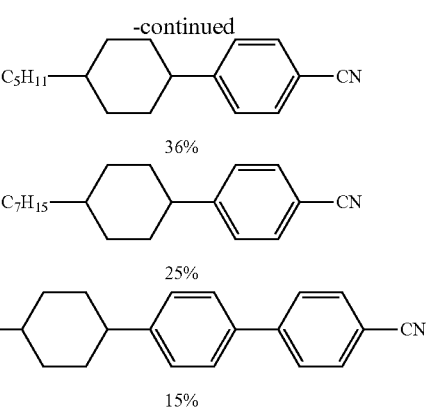

36%

25%

15%

When the dielectric anisotropy of the compound was zero or negative, base liquid crystal (B) described below was used. A proportion of each component was expressed by % by weight.

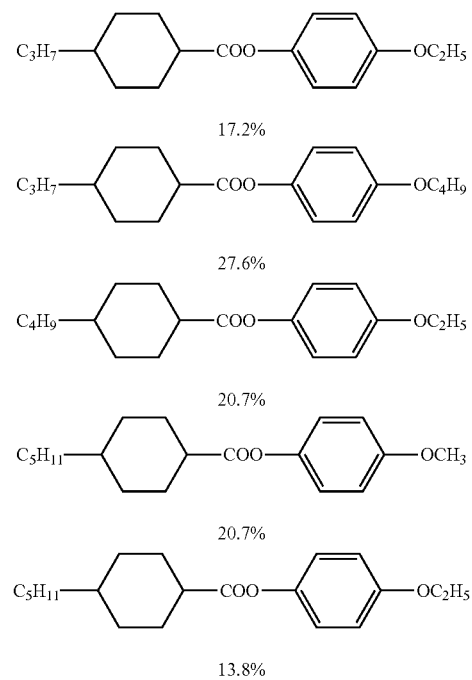

17.2%

27.6%

20.7%

20.7%

13.8%

Measuring method: Physical properties were measured according to the methods described below. Most of the methods are described in the Standard of Japan Electronics and Information Technology Industries Association (hereinafter, abbreviated as JEITA) discussed and established in JEITA (JEITA ED-2521B). A modification of the methods was also used. No thin film transistor (TFT) was attached to a TN device used for measurement.

(1) Phase structure: A sample was placed on a hot plate of a melting point apparatus (FP-52 Hot Stage made by Mettler-Toledo International Inc.) equipped with a polarizing microscope. A state of phase and a change thereof were observed with the polarizing microscope while the sample was heated at a rate of 3° C. per minute, and a kind of the phase was specified.

(2) Transition temperature (° C.): For measurement, a differential scanning calorimeter, Diamond DSC System, made by PerkinElmer, Inc., or a high sensitivity differential scanning calorimeter, X-DSC7000, made by SII NanoTechnology Inc. was used. A sample was heated and then cooled at a rate of 3° C. per minute, and a starting point of an endothermic peak or an exothermic peak caused by a phase change of the sample was determined by extrapolation, and thus a transition temperature was determined. A polymerization starting temperature and a melting point of a compound were also measured using the apparatus. Temperature at which a compound undergoes transition from a solid to a liquid crystal phase such as the smectic phase and the nematic phase may be occasionally abbreviated as "minimum temperature of the liquid crystal phase." Temperature at which the compound undergoes transition from the liquid crystal phase to liquid may be occasionally abbreviated as "clearing point."

A crystal was expressed as C. When the crystal can be distinguished to two kinds, each crystal was represented as $C_1$ or $C_2$. The smectic phase or the nematic phase was expressed as S or N. When the phase can be distinguished as a smectic A phase, a smectic B phase, a smectic C phase, and a smectic F phase, the phases were expressed as $S_A$, $S_B$, $S_C$ and $S_F$, respectively. A liquid (isotropic) was expressed as I. A transition temperature was expressed as "C 50.0 N 100.0 I," for example. The expression indicates that a transition temperature from the crystals to the nematic phase is 50.0° C., and a transition temperature from the nematic phase to the liquid is 100.0° C.

(3) Compatibility of the compound: samples formed by mixing the compound with the base liquid crystal were prepared so that a proportion of the compound was 20% by weight, 15% by weight, 10% by weight, 5% by weight, 3% by weight or 1% by weight. The sample was put into a glass vial, and stored for a fixed period of time in a freezing chamber at −10° C. or −20° C. Whether the nematic phase of the sample was maintained or the crystal (or smectic phase) precipitated was observed. A condition on which the nematic phase was maintained was used as a scale of the compatibility. A proportion of the compound and a temperature of the freezing chamber may be occasionally changed when necessary.

(4) Maximum temperature of the nematic phase ($T_{NI}$ or NI; ° C.): A sample was placed on a hot plate of a melting point apparatus equipped with a polarizing microscope, and was heated at a rate of 1° C. per minute. Temperature when a part of the sample began to change from a nematic phase to an isotropic liquid was measured. When the sample was a mixture of compound (1) and the base liquid crystal, the maximum temperature was expressed as a symbol $T_{NI}$. The value was calculated using the extrapolation method described above. When the sample was a mixture of compound (1) and a compound selected from compounds (2) to (15), the measured value was expressed by a symbol NI. A maximum temperature of the nematic phase may be occasionally abbreviated as "maximum temperature."

(5) Minimum temperature of the nematic phase ($T_C$; ° C.): Samples each having the nematic phase were put in glass vials and kept in freezers at temperatures of 0° C., −10° C., −20° C., −30° C. and −40° C. for 10 days, and then liquid crystal phases were observed. For example, when the sample maintained the nematic phase at −20° C. and changed to crystals or a smectic phase at −30° C., Tc of the sample was expressed as Tc←−20° C. A minimum temperature of the nematic phase may be occasionally abbreviated as "minimum temperature."

(6) Viscosity (bulk viscosity; μ; measured at 20° C.; mPa·s): For measurement, an E type rotational viscometer by Tokyo Keiki Co., Ltd. was used.

(7) Optical anisotropy (refractive index anisotropy; measured at 25° C.; Δn): Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of the optical anisotropy (Δn) was calculated from an equation: Δn=n∥−n⊥.

(8) Specific resistance (ρ; measured at 25° C.; Ωcm): Into a vessel equipped with electrodes, 1.0 milliliter of a sample was injected. A direct current voltage (10 V) was applied to the vessel, and a direct current after 10 seconds was measured. Specific resistance was calculated from the following equation: (specific resistance)={(voltage)×(electric capacity of a vessel)}/{(direct current)×(dielectric constant of vacuum)}.

(9) Voltage holding ratio (VHR-1; measured at 25° C.; %): A TN device used for measurement had a polyimide alignment film, and a distance (cell gap) between two glass substrates was 5 micrometers. A sample was put in the device, and the device was sealed with an ultraviolet-curable adhesive. A pulse voltage (at 5 V for 60 microseconds) was applied to charge the device. A decaying voltage was measured for 16.7 milliseconds with a high-speed voltmeter, and area A between a voltage curve and a horizontal axis in a unit cycle was determined. Area B is an area without decay. A voltage holding ratio is expressed in terms of a percentage of area A to area B.

(10) Voltage holding ratio (VHR-2; measured at 80° C.; %): A voltage holding ratio was measured according to the method described above except that a sample was measured at 80° C. in place of 25° C. The thus obtained value was expressed in terms of VHR-2.

(11) Flicker rate (measured at 25° C.; %): For measurement, Multimedia display circuit tester 3298F made by Yokogawa Electric Cooperation was used. A light source was LED. A sample was put into a normally black mode FFS device in which a distance (cell gap) between two glass substrates was 3.5 micrometers, and a rubbing direction was antiparallel. The device was sealed with an ultraviolet-curable adhesive. Voltage was applied to the device, and voltage corresponding to a maximum amount of light transmitted through the device was measured. A sensor part was brought close to the device while the voltage was applied, and a flicker rate displayed thereon was read.

A method for measuring physical properties may be occasionally different between a sample having the positive dielectric anisotropy and a sample having the negative dielectric anisotropy. Measuring methods when the dielectric anisotropy was positive were described in a section (12a) to a section (16a). Measuring methods when the dielectric anisotropy was negative were described in a section (12b) to a section (16b).

(12a) Viscosity (rotational viscosity; γ1; measured at 25° C.; mPa·s; a sample having the positive dielectric anisotropy): Measurement was carried out according to the method described in M. Imai et al., Molecular Crystals and Liquid Crystals, Vol. 259, p. 37 (1995). A sample was put into a TN device in which a twist angle was 0 degree, and a distance (cell gap) between two glass substrates was 5 micrometers. Voltage was applied stepwise to the device at an increment of 0.5 V from 16 V to 19.5 V. After a period of 0.2 second with no voltage application, voltage was repeatedly applied under conditions of only one rectangular wave (rectangular pulse; 0.2 second) and no voltage application (2 seconds). A peak current and a peak time of transient current generated by the applied voltage were measured. A value of the rotational viscosity was obtained from the measured values, the article of M. Imai et al., and equation (8) on page 40. A value of dielectric anisotropy required for the calculation was determined using the device by which the rotational viscosity was measured and by the method described below.

(12b) Viscosity (rotational viscosity; γ1; measured at 25° C.; mPa·s; a sample having the negative dielectric anisotropy): Measurement was carried out according to the method described in M. Imai et al., Molecular Crystals and Liquid Crystals, Vol. 259, p. 37 (1995). A sample was put into a VA device in which a distance (cell gap) between two glass substrates was 20 micrometers. Voltage was applied stepwise to the device at an increment of 1 V from 39 V to 50 V. After a period of 0.2 second with no voltage application, voltage was repeatedly applied under conditions of only one rectangular wave (rectangular pulse; 0.2 second) and no voltage application (2 seconds). A peak current and a peak time of transient current generated by the applied voltage were measured. A value of the rotational viscosity was obtained from the measured values, the article of M. Imai et al., and equation (8) on page 40. A dielectric anisotropy required for the calculation was measured in the following section for dielectric anisotropy.

(13a) Dielectric anisotropy (Δ∈; measured at 25° C.; a sample having the positive dielectric anisotropy): A sample was put into a TN device in which a distance (cell gap) between two glass substrates was 9 micrometers and a twist angle was 80 degrees. Sine waves (10 V, 1 kHz) were applied to the device, and after 2 seconds, a dielectric constant (∈∥) in a major axis direction of the liquid crystal molecules was measured. Sine waves (0.5 V, 1 kHz) were applied to the device, and after 2 seconds, a dielectric constant (∈⊥) in a minor axis direction of the liquid crystal molecules was measured. A value of the dielectric anisotropy was calculated from an equation: Δ∈=∈∥−∈⊥.

(13b) Dielectric anisotropy (ΔE; measured at 25° C.; a sample having the negative dielectric anisotropy): A value of the dielectric anisotropy was calculated from the equation: Δ∈=∈∥−∈⊥. A dielectric constant (∈∥ and ∈⊥) was measured as described below.

1) Measurement of a dielectric constant (∈∥): An ethanol (20 mL) solution of octadecyltriethoxysilane (0.16 mL) was applied to a well-cleaned glass substrate. After rotating the glass substrate with a spinner, the glass substrate was heated at 150° C. for 1 hour. A sample was put into a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant (∈∥) in a major axis direction of the liquid crystal molecules was measured.

2) Measurement of a dielectric constant (∈⊥): A polyimide solution was applied to a well-cleaned glass substrate. After calcining the glass substrate, rubbing treatment was applied to the alignment film obtained. A sample was put into a TN device in which a distance (cell gap) between two glass substrates was 9 micrometers and a twist angle was 80 degrees. Sine waves (0.5 V, 1 kHz) were applied to the device, and after 2 seconds, a dielectric constant (∈⊥) in a minor axis direction of the liquid crystal molecules was measured.

(14a) Elastic constant (K; measured at 25° C.; pN; a sample having the positive dielectric anisotropy): For measurement, HP4284A LCR Meter made by Yokogawa-Hewlett-Packard Co. was used. A sample was put into a horizontal alignment device in which a distance (cell gap) between two glass substrates was 20 micrometers. Voltage of 0 V to 20 V was applied to the device, and electrostatic capacity (C) and applied voltage (V) were measured. The measured values were fitted to equation (2.98) and equation (2.101) on page 75 of "Liquid Crystal Device Handbook" (Ekisho Debaisu Handobukku, in Japanese; Nikkan Kogyo Shimbun, Ltd.), and values of $K_{11}$ and $K_{33}$ were obtained from equation (2.99). Next, $K_{22}$ was calculated from equation (3.18) on page 171 by using the values of $K_{11}$ and $K_{33}$ obtained previously. Elastic constant K is expressed using a mean value of the thus determined $K_{11}$, $K_{22}$ and $K_{33}$.

(14b) Elastic constant ($K_{11}$ and $K_{33}$; measured at 25° C.; pN; a sample having the negative dielectric anisotropy): For measurement, Elastic Constant Measurement System Model EC-1 made by TOYO Corporation was used. A sample was put into a homeotropic device in which a distance (cell gap) between two glass substrates was 20 micrometers. Voltage of 20V to 0V was applied to the device, and electrostatic capacity (C) and applied voltage (V) were measured. The measured values were fitted to equation (2.98) and equation (2.101) on page 75 of "Liquid Crystal Device Handbook" (Ekisho Debaisu Handobukku, in Japanese; Nikkan Kogyo Shimbun, Ltd.), and a value of elastic constant was obtained from equation (2.100).

(15a) Threshold voltage (Vth; measured at 25° C.; V; a sample having the positive dielectric anisotropy): For measurement, an LCD-5100 luminance meter made by Otsuka Electronics Co., Ltd. was used. A light source was a halogen lamp. A sample was put into a normally white mode TN device in which a distance (cell gap) between two glass substrates was 0.45/Δn (μm) and a twist angle was 80 degrees. Voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage is expressed in terms of a voltage at 90% transmittance.

(15b) Threshold voltage (Vth; measured at 25° C.; V; a sample having the negative dielectric anisotropy): For measurement, an LCD-5100 luminance meter made by Otsuka Electronics Co., Ltd. was used. A light source was a halogen lamp. A sample was put into a normally black mode VA device in which a distance (cell gap) between two glass substrates was 4 micrometers and a rubbing direction was anti-parallel, and the device was sealed with an ultraviolet-curable adhesive. Voltage (60 Hz, rectangular waves) to be applied to the device was stepwise increased from 0 V to 20 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage is expressed in terms of voltage at 10% transmittance.

(16a) Response time (τ; measured at 25° C.; ms; a sample having the positive dielectric anisotropy): For measurement, an LCD-5100 luminance meter made by Otsuka Electronics Co., Ltd. was used. A light source was a halogen lamp. A low-pass filter was set to 5 kHz. A sample was put into a normally white mode TN device in which a distance (cell gap) between two glass substrates was 5.0 micrometers and a twist angle was 80 degrees. Voltage (rectangular waves; 60 Hz, 5 V, 0.5 second) was applied to the device. On the occasion, the device was irradiated with light from a direction perpendicular to the device, and an amount of light transmitted through the device was measured. The maximum amount of light corresponds to 100% transmittance and the minimum amount of light corresponds to 0% transmittance. A rise time (τr; millisecond) was expressed in terms of time required for a change from 90% transmittance to 10% transmittance. A fall time (τf; millisecond) was expressed in terms of time required for a change from 10% transmittance to 90% transmittance. A response time was represented by a sum of the rise time and the fall time thus obtained.

(16b) Response time (τ; measured at 25° C.; ms; a sample having the negative dielectric anisotropy): For measurement, an LCD-5100 luminance meter made by Otsuka Electronics Co., Ltd. was used. A light source was a halogen lamp. A low-pass filter was set to 5 kHz. A sample was put into a normally black mode PVA device in which a distance (cell gap) between two glass substrates was 3.2 micrometers, and a rubbing direction was antiparallel. The device was sealed with an ultraviolet-curable adhesive. Voltage slightly exceeding a threshold voltage was applied to the device for 1 minute, and then the device was irradiated with ultraviolet light of 23.5 mW/cm$^2$ for 8 minutes while voltage of 5.6 V was applied. Voltage (rectangular waves; 60 Hz, 10 V, 0.5 second) was applied to the device. On the occasion, the device was irradiated with light from a direction perpendicular to the device, and an amount of light transmitted through the device was measured. The maximum amount of light corresponds to 100% transmittance and the minimum amount of light corresponds to 0% transmittance. A response time was expressed in terms of time required for a change from 90% transmittance to 10% transmittance (fall time; millisecond).

Synthesis Example 1

Synthesis of Compound (No. 1)

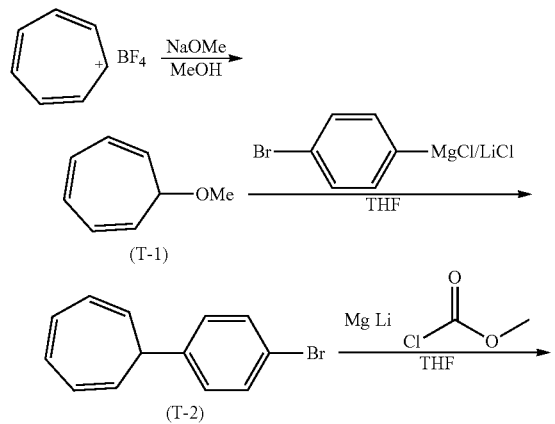

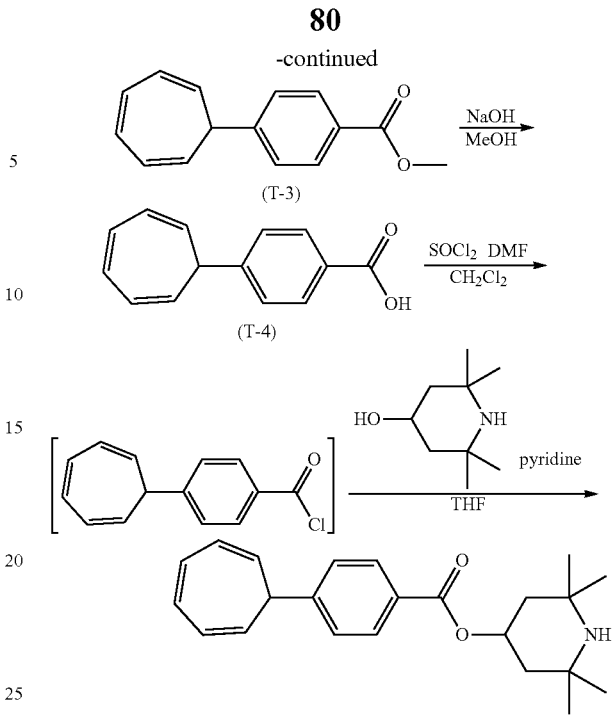

First Step:

Into a reaction vessel under an argon atmosphere, tropylium tetrafluoroborate (13.20 g, 74.2 mmol) and methanol (75 mL) were put, and a NaOMe/methanol solution (25 mL, 125.0 mmol) was added dropwise thereto at room temperature, and the resulting mixture was stirred for 12 hours. Then, a NaOMe/methanol solution (5 mL, 25.0 mmol) was added dropwise thereto, and the resulting mixture was stirred at 60° C. for 4 hours. The resulting reaction mixture was cooled to 25° C., and then poured into water. The resulting mixture was subjected to extraction with hexane, and the extract was washed with a saturated aqueous solution of sodium hydrogencarbonate and water, and dried over anhydrous magnesium sulfate. The solvent was distilled off under normal pressure to obtain a residue. The residue was purified by vacuum distillation to obtain compound (T-1) (5.34 g, yield: 59%).

Second Step:

Into a reaction vessel under an argon atmosphere, i-PrMgCl/LiCl (66 mL, 66.0 mmol) was put, and a THF (40 mL) solution of p-dibromobenzene (15.48 g, 66.0 mmol) was added dropwise thereto at room temperature, and the resulting mixture was stirred at 45° C. for 3 hours. Then, the resulting reaction mixture was cooled to 25° C., and a THF (30 mL) solution of compound (T-1) (5.34 g, 43.7 mmol) was added dropwise thereto, and the resulting mixture was further stirred at 50° C. for 1 hour. The resulting reaction mixture was cooled to 25° C., and then poured into a 10% ammonium chloride aqueous solution. The resulting mixture was subjected to extraction with isopropyl ether, and the extract was washed with saturated brine and water, and dried over anhydrous magnesium sulfate. The solvent was distilled off under normal pressure to obtain a residue. The residue was purified by silica gel column chromatography (hexane/ethyl acetate=95/5, volume ratio) to obtain compound (T-2) (7.69 g, yield: 71%).

Third Step:

Into a reaction vessel under an argon atmosphere, Mg (0.83 g, 34.2 mmol), LiCl (1.45 g, 34.2 mmol), and THF (5 mL) were put. A THF (20 mL) solution of compound (T-2) (7.69 g, 31.1 mmol) was added dropwise thereto at room temperature, and the resulting mixture was stirred at 50° C.

for 2 hours to prepare a Grignard reagent. Methyl chloroformate (6.11 g, 64.7 mmol) and THF (30 mL) were put into another reaction vessel under an argon atmosphere, and the resulting mixture was cooled to −5° C. The Grignard reagent previously prepared was added dropwise thereto, and the resulting mixture was stirred for 1 hour. The reaction mixture was poured into a 10% ammonium chloride aqueous solution. The resulting mixture was subjected to extraction with ether, and the extract was washed with saturated brine, and water, and dried over anhydrous magnesium sulfate. The solvent was distilled off under normal pressure to obtain a residue. The residue was purified by silica gel column chromatography (hexane/ethyl acetate=95/5, volume ratio) to obtain compound (T-3) (4.42 g, yield: 63%).

Fourth Step:

Into a reaction vessel, compound (T-3) (2.02 g, 8.9 mmol) and methanol (20 mL) were put, and a NaOH (2 g, 50 mmol) aqueous solution (10 mL) was added dropwise thereto at room temperature, and the resulting mixture was stirred for 1.5 hours. To the reaction mixture, a 10% HCl aqueous solution (50 mL) was added, and the resulting mixture was subjected to extraction with ethyl acetate, and the extract was washed with saturated brine, and the solvent was distilled off under normal pressure to obtain compound (T-4) (1.89 g, yield: 100%).

Fifth Step:

Into a reaction vessel under an argon atmosphere, compound (T-4) (1.89 g, 8.9 mmol), dichloromethane (20 mL), and DMF (2 mL) were put, and thionyl chloride (2 mL, 27.4 mmol) was added dropwise thereto at room temperature, and the resulting mixture was heated under reflux and stirred for 3 hours. The resulting reaction mixture was cooled to 25° C., and then the solvent was distilled off under normal pressure to obtain a residue. The residue, dichloromethane (20 mL), tetramethyl piperidinol (4.2 g, 26.7 mmol), and pyridine (15 mL) were put into a reaction vessel under an argon atmosphere, and the resulting mixture was stirred overnight, and the resulting reaction mixture was poured into water. The resulting mixture was subjected to extraction with ethyl acetate, and the extract was washed with a 10% HCl aqueous solution, 5% sodium hydrogencarbonate water, and saturated brine, and the solvent was distilled off under normal pressure to obtain a residue. The residue was purified by silica gel column chromatography (chloroform/methanol=95/5, volume ratio), and further purified by recrystallization (hexane) to obtain compound (No. 1) (0.82 g, yield: 260).

$^1$H-NMR (CDCl$_3$; Δ ppm): 8.03 (dd, 2H), 7.44 (dd, 2H), 6.76 (t, 2H), 6.31-6.28 (m, 2H), 5.45 (tt, 1H), 5.40 (dd, 2H), 2.82 (t, 1H), 2.07 (dd, 2H) and 1.42-1.17 (m, 15H).

Synthesis Example 2

Compound (No. 11) was prepared according to the method in Synthesis Example 1.

$^1$H-NMR (CDCl$_3$; δ ppm): 8.03 (d, 2H), 7.43 (d, 2H), 6.75 (quin, 2H), 6.29 (m, 2H), 5.40 (dd, 2H), 5.32 (tt, 1H), 2.82 (t, 1H), 2.31 (br, 3H), 2.01 (d, 2H), 1.26-1.16 (m, 14H).

Synthesis Example 3

Synthesis of Compound (No. 12).

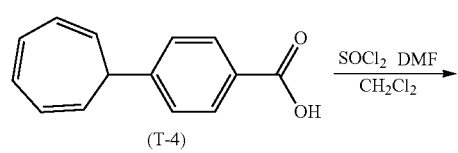
(T-4)

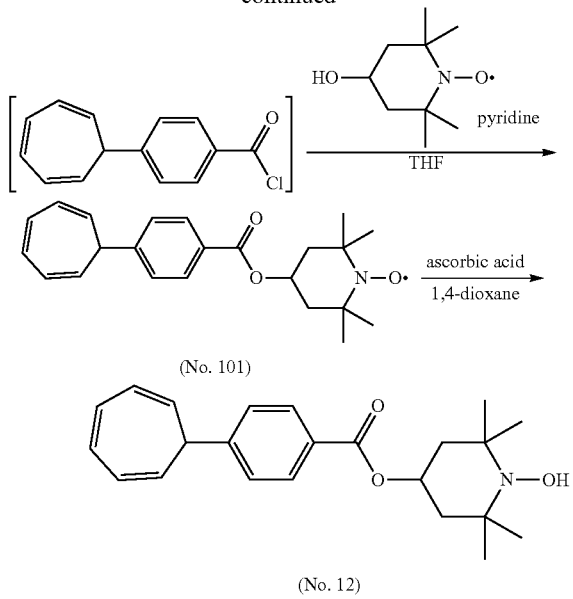
(No. 101)

(No. 12)

First Step:

Compound (No. 101) was prepared according to the method in Synthesis Example 1.

Compound (No. 101) (2.00 g, yield: 39%)

Second Step:

Into a reaction vessel under an argon atmosphere, compound (No. 101) (2.00 g, 5.5 mmol) and 1,4-dioxane (20 mL) were put, and an aqueous solution of ascorbic acid (2.89 g, 16.4 mmol) was added dropwise thereto at room temperature, and the resulting mixture was stirred for 3 hours. The resulting reaction mixture was subjected to extraction with dichloromethane, and the extract was washed with saturated brine, and the solvent was distilled off under normal pressure to obtain a residue. The residue was purified by silica gel column chromatography, and further purified by recrystallization to obtain compound (No. 12) (0.86 g, yield: 43%).

$^1$H-NMR (CDCl$_3$; δ ppm): 8.02 (d, 2H), 7.43 (d, 2H), 6.75 (quin, 2H), 6.28 (m, 2H), 5.40 (dd, 2H), 5.30 (tt, 1H), 4.22 (br, 1H), 2.82 (t, 1H), 2.04 (dd, 2H), 1.71 (dd, 2H), 1.25 (s, 12H).

Synthesis Example 4

Compound (No. 14) was prepared according to the method in Synthesis Example 1.

$^1$H-NMR (CDCl$_3$; δ ppm): 8.02 (d, 2H), 7.42 (d, 2H), 6.75 (quin, 2H), 6.28 (m, 2H), 5.39 (dd, 2H), 5.28 (tt, 1H), 3.63 (s, 3H), 2.81 (t, 1H), 1.97 (dd, 2H), 1.71 (dd, 2H), 1.25 (s, 6H), 1.24 (s, 6H).

Comparison of Solubility at a Low Temperature

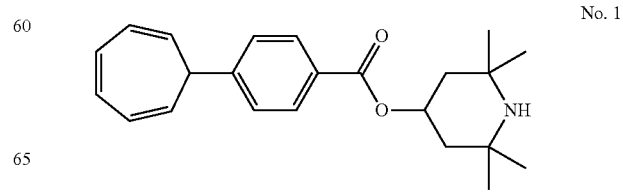
No. 1

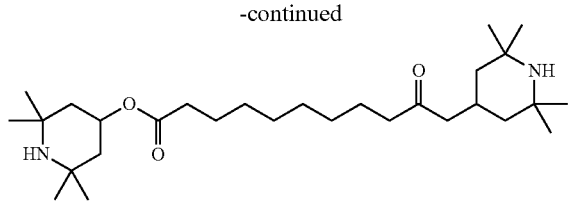

LA77

Comparison was made on solubility at a low temperature for compound (No. 1) according to the invention and comparative compound (LA77). Compound (LA77) is a hindered amine light stabilizer made by ADEKA Corporation. Compound (No. 1) was added to liquid crystal composition (A) described below at a portion of 0.1%, and the resulting mixture was heated for 30 minutes at 50° C. The solution was stored for 20 days at −20° C. Then, whether or not a crystal precipitated was visually observed. Meanwhile, comparative compound (LA77) made by ADEKA Corporation was also observed in a similar manner. The results are shown in Table 3. In symbols in Table 3, "O" shows that no crystal precipitated, and "x" shows that a crystal precipitated. From Table 3, compound (No. 1) according to the invention was found to have good solubility in liquid crystal composition (A). Moreover, components and proportions of liquid crystal composition (A) were as described below.

Liquid Crystal Composition (A)

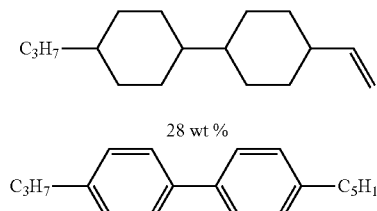

28 wt %

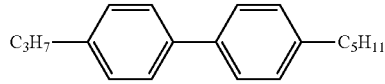

11 wt %

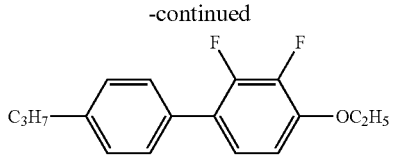

13 wt %

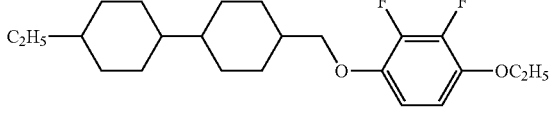

18 wt %

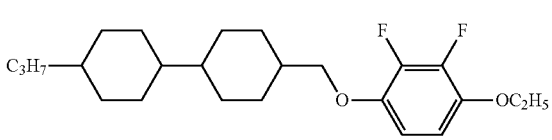

16 wt %

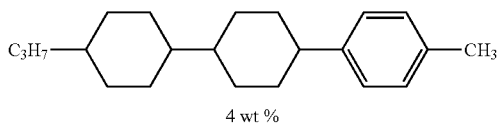

4 wt %

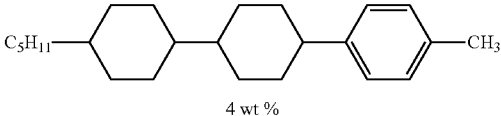

4 wt %

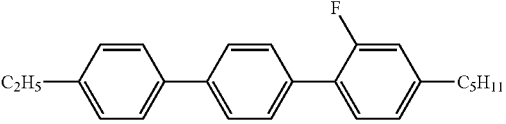

6 wt %

Characteristics of liquid crystal composition (A) were as follows: NI=76.0° C.; Δn=0.107; Δ∈=−3.0.

TABLE 3

Comparison of solubility in liquid crystal composition (A)

| Compound | Formula | Solubility (−20° C., for 20 days) |
|---|---|---|
| Compound (No. 1) | ![structure] | O |
| Comparative Compound (LA77) | ![structure] | x |

According to the synthesis method described in Example 1, components (No. 1) to (No. 100) can be prepared.
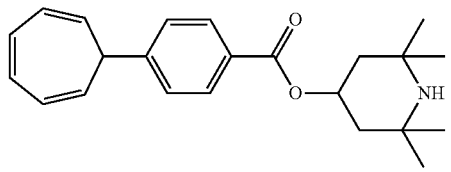
1
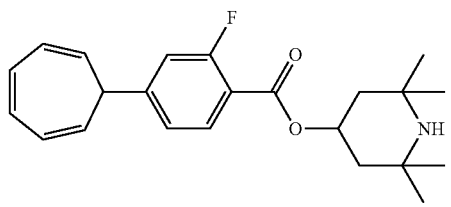
2
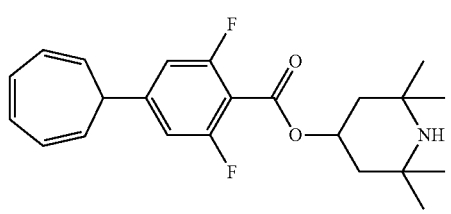
3
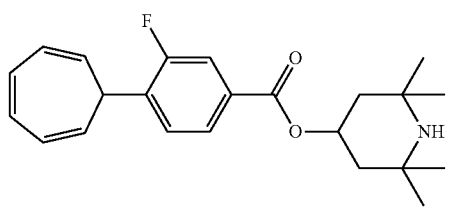
4
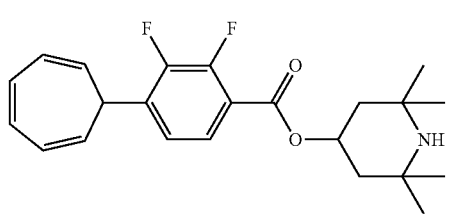
5
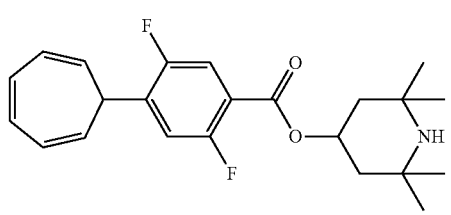
6
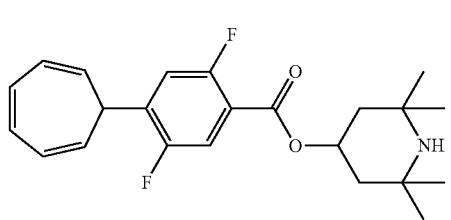
7
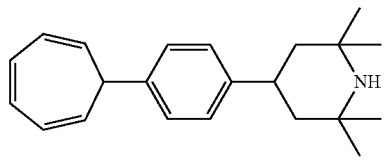
8
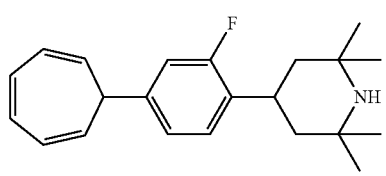
9
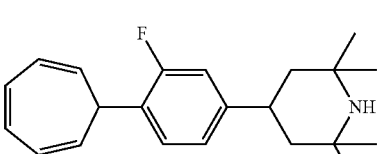
10
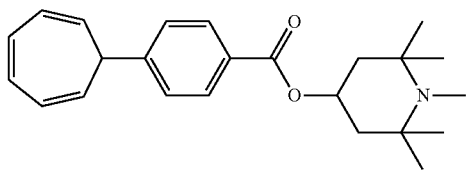
11
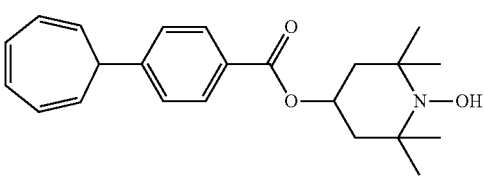
12
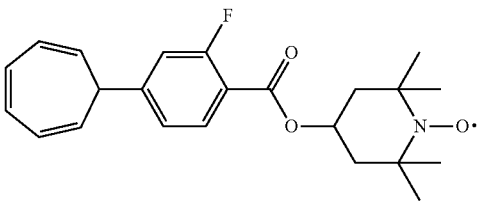
13
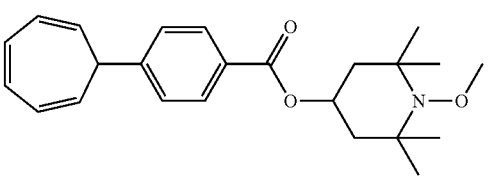
14
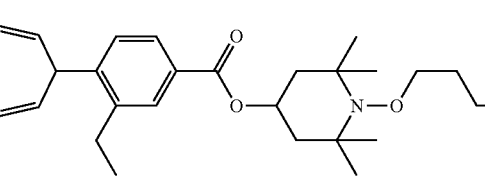
15
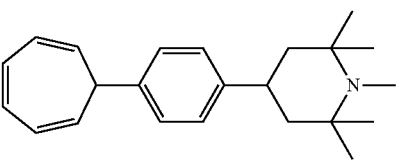
16

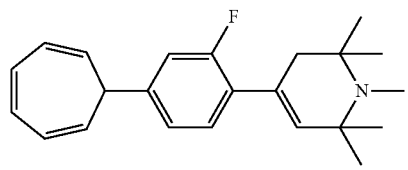
17
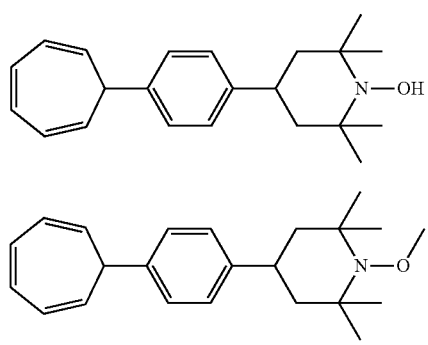
18
19
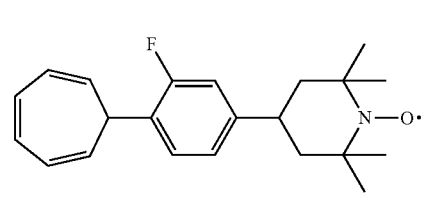
20
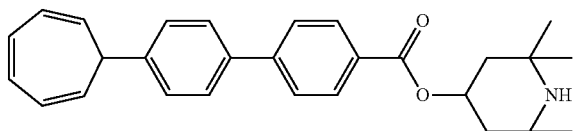
21
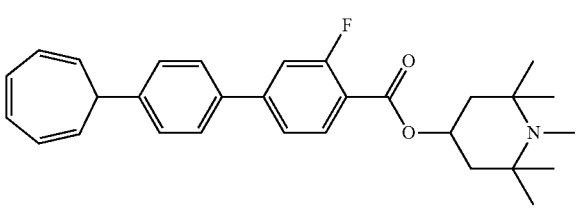
22
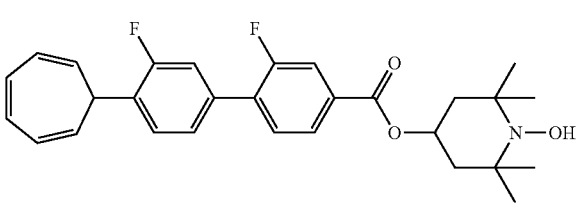
23
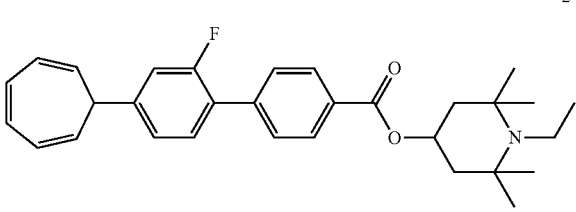
24
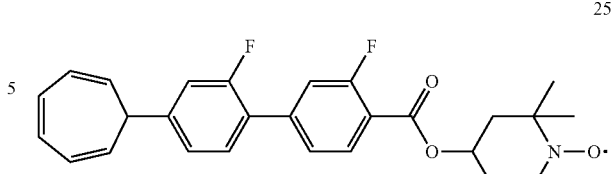
25
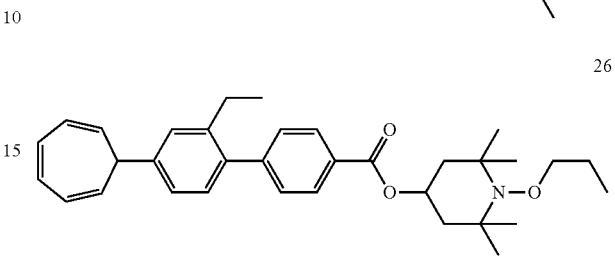
26
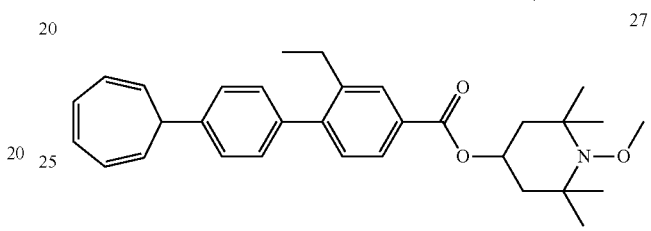
27
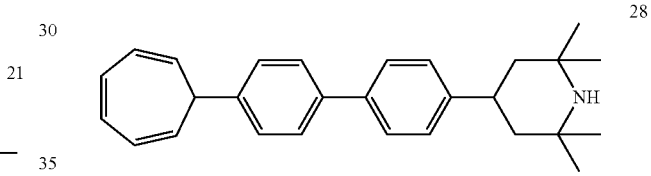
28
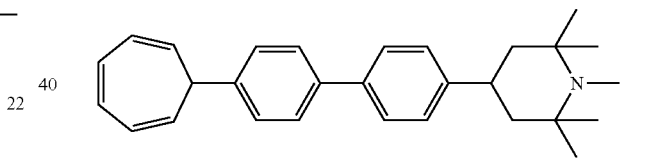
29
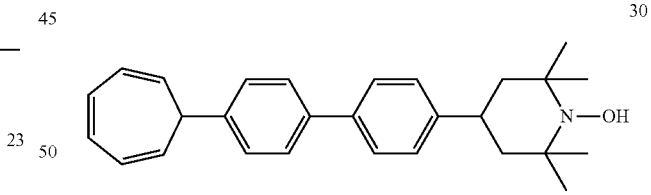
30
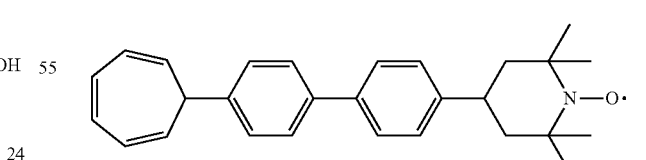
31
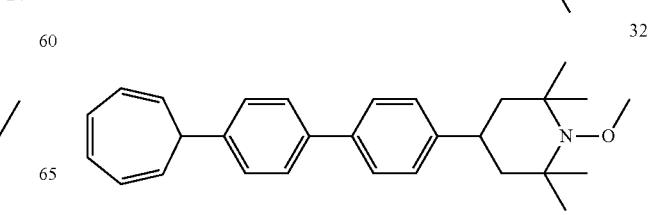
32

33
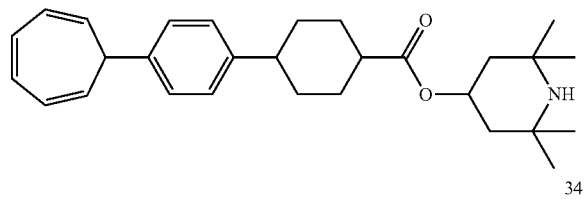
34
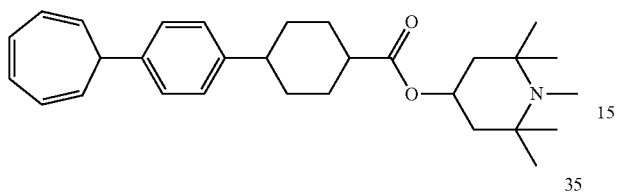
35
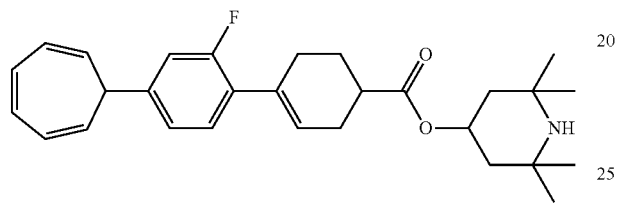
36
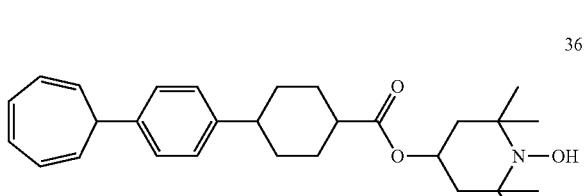
37
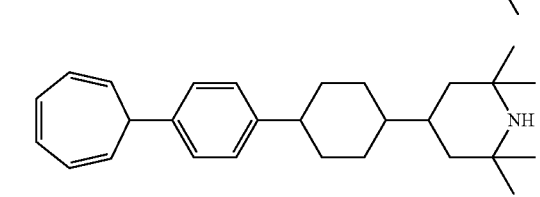
38
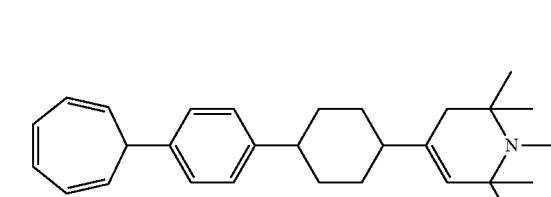
39
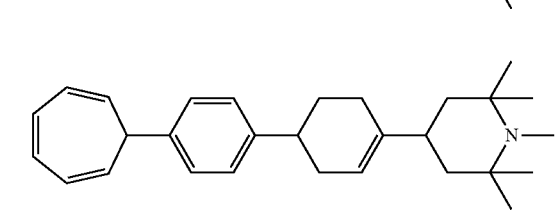
40
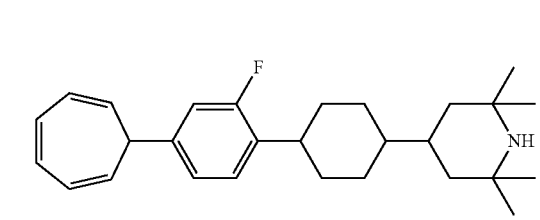
41
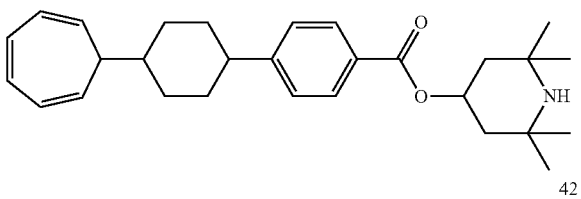
42
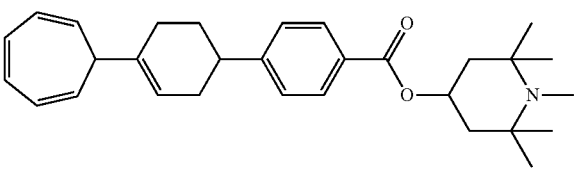
43
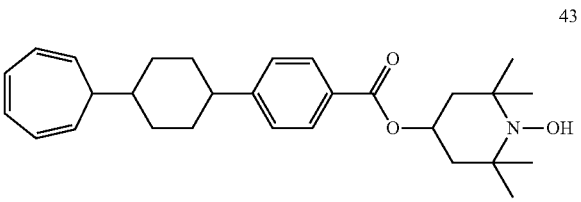
44
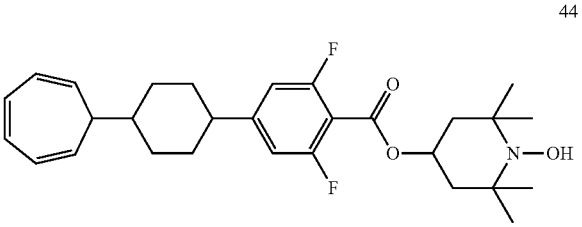
45
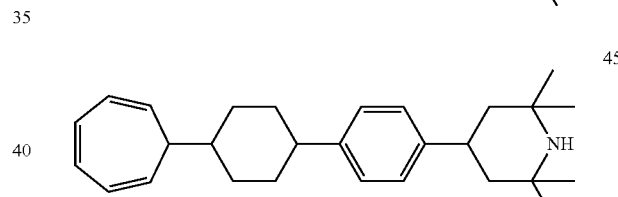
46
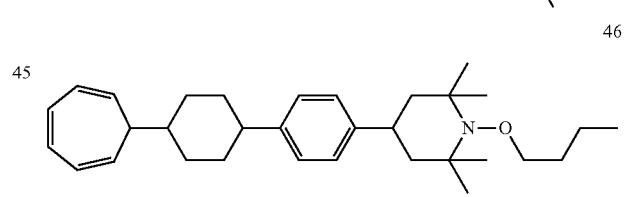
47
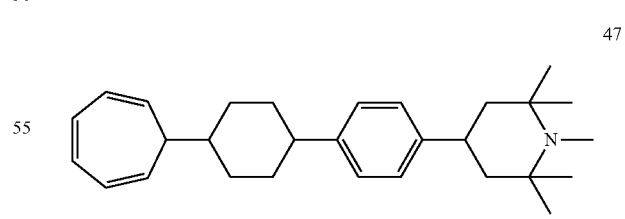
48
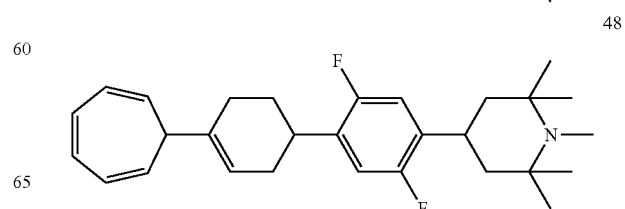

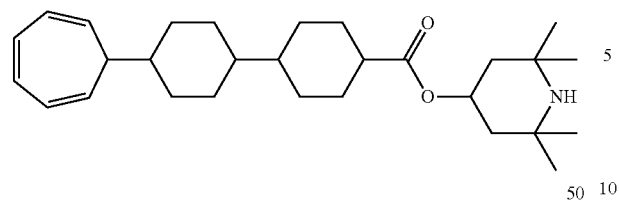
49
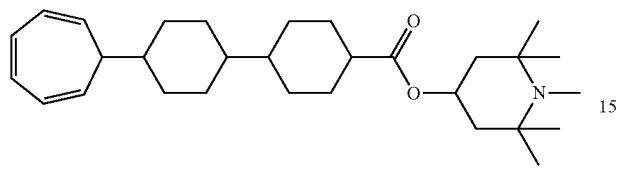
50
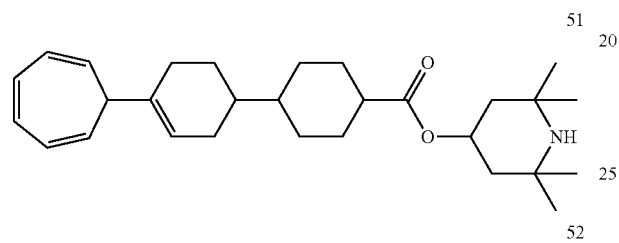
51
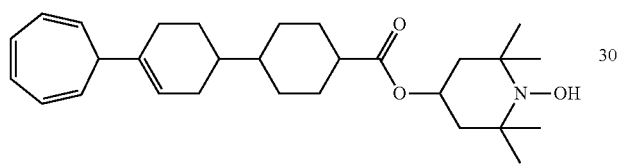
52
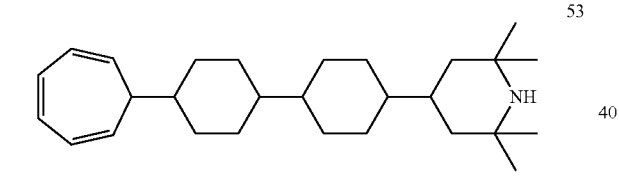
53
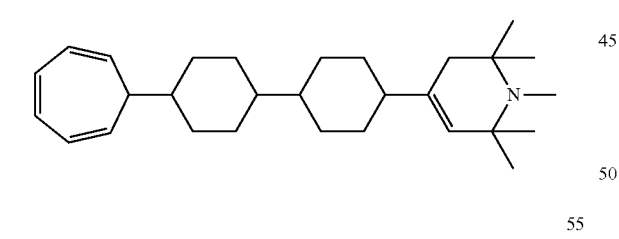
54
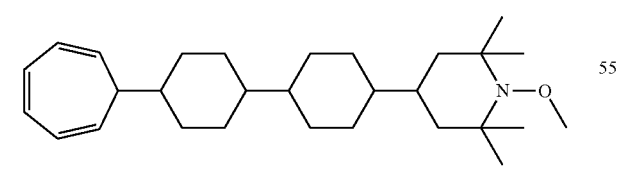
55
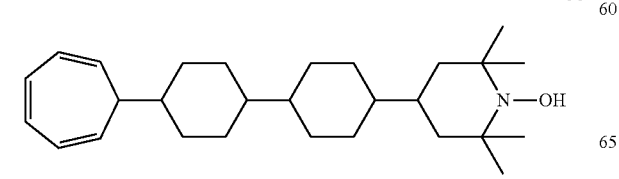
56
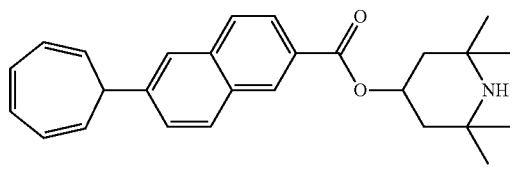
57
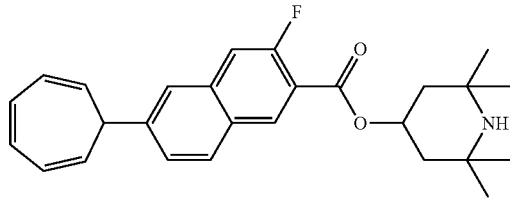
58
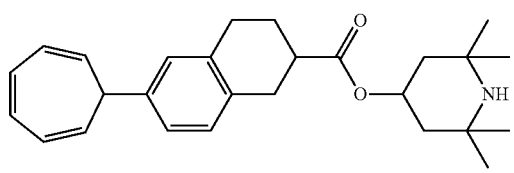
59
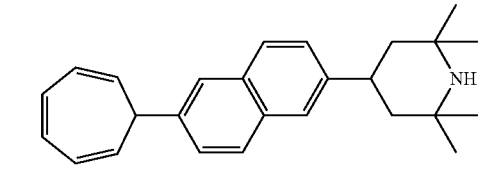
60
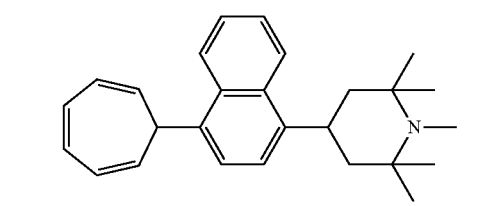
61
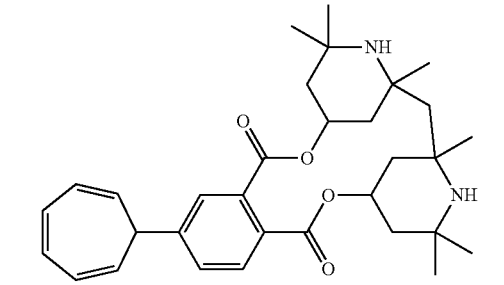
62
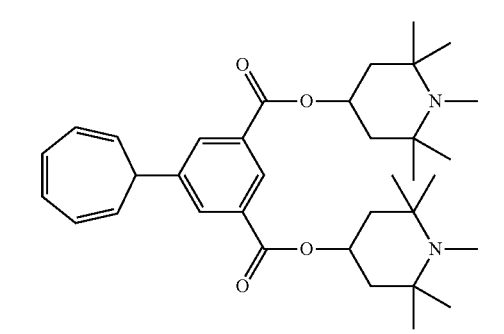
63

64
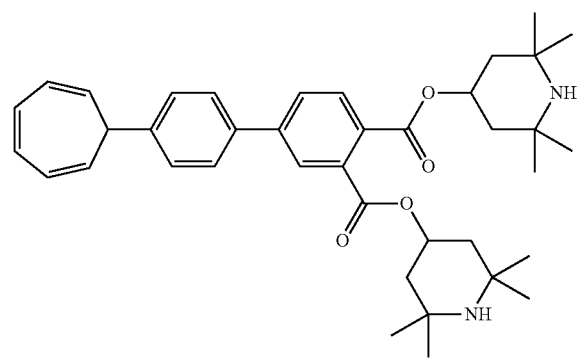
65
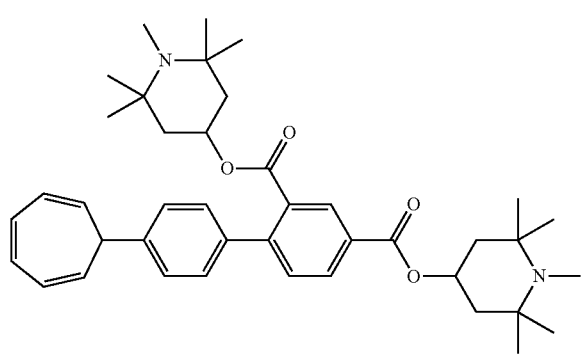
66
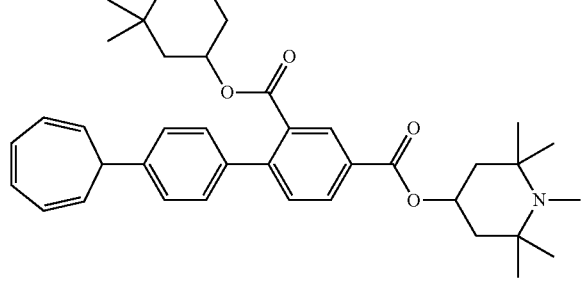
67
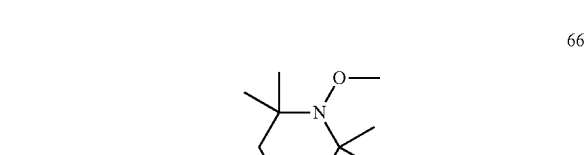
68
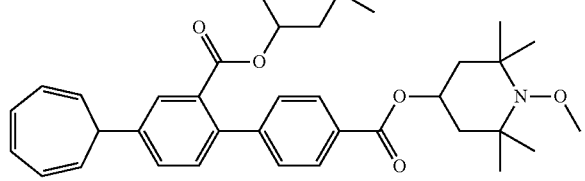
69
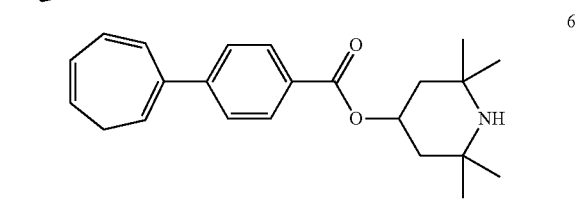
70
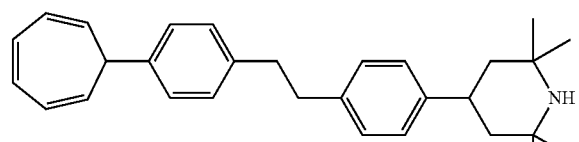
71
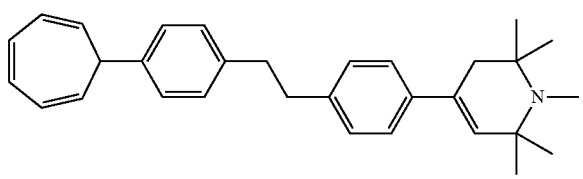
72
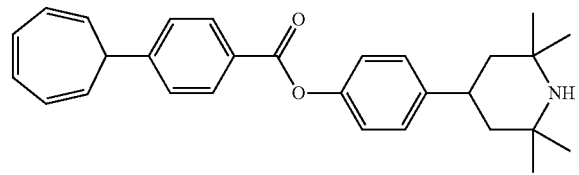
73
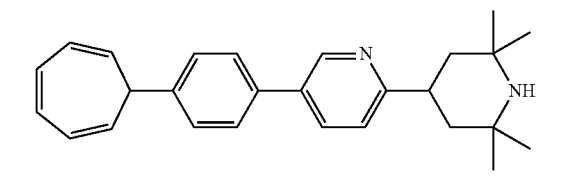
74
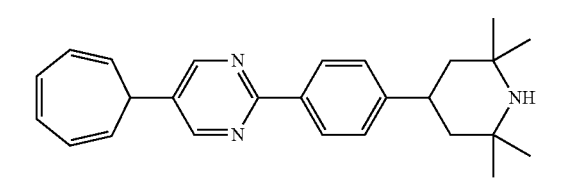
75
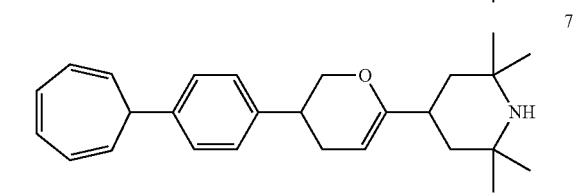
76
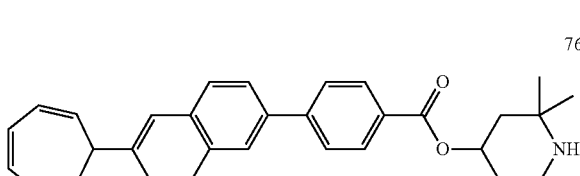
77
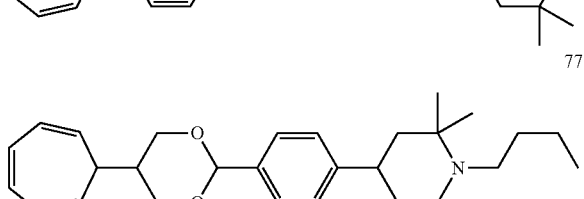

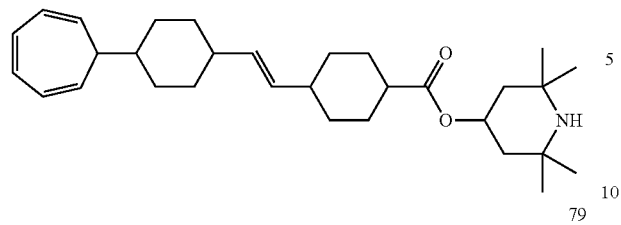
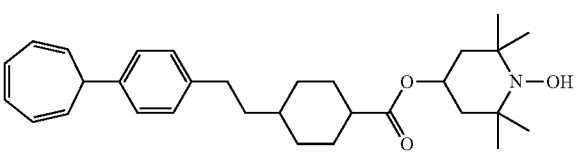
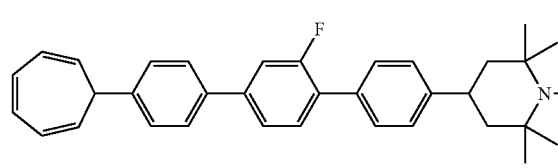
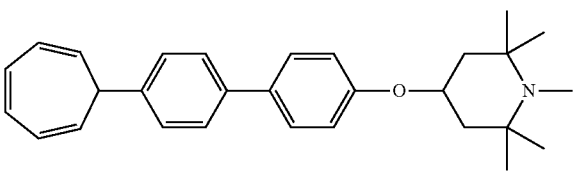
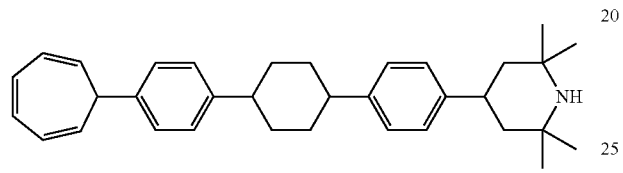
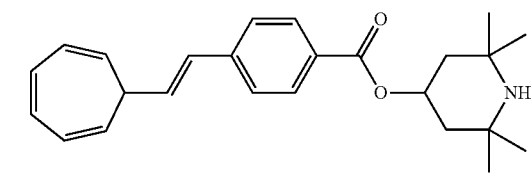
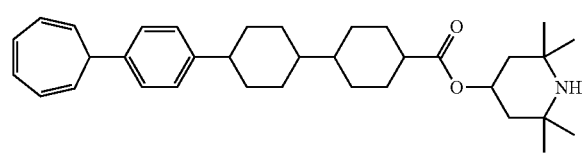
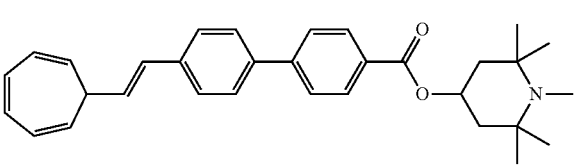
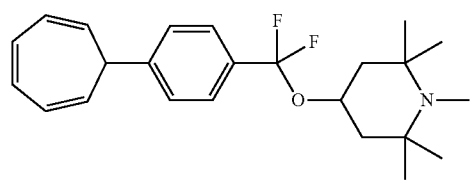
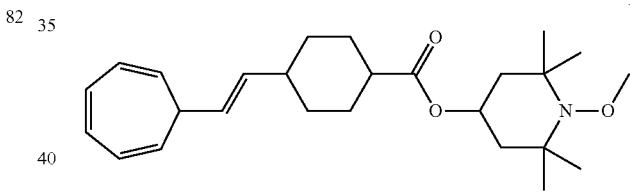
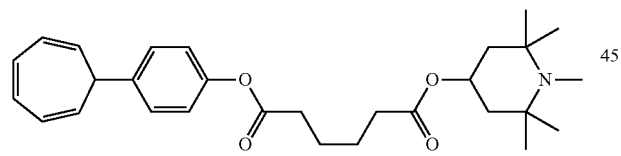
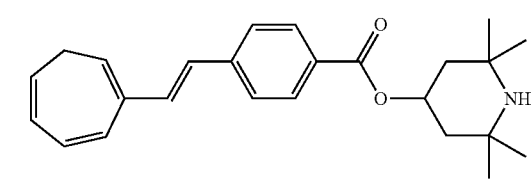
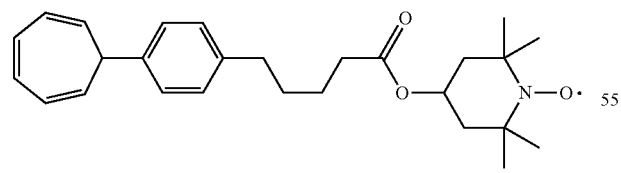
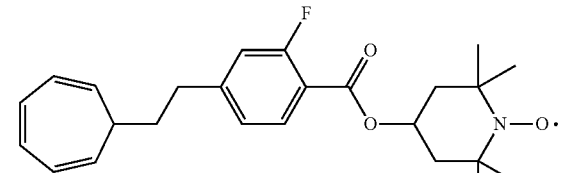
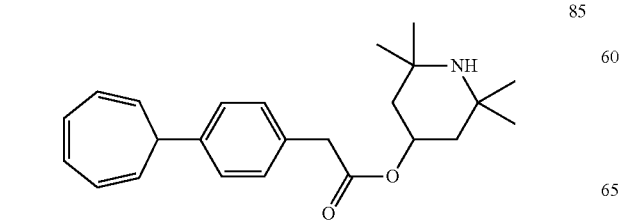
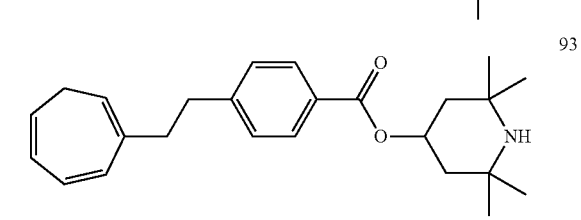

94

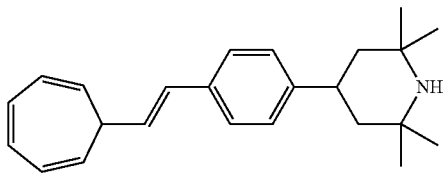

95

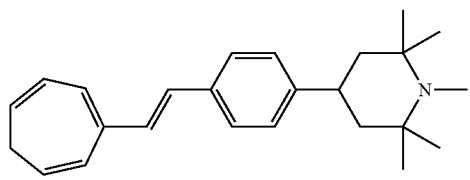

96

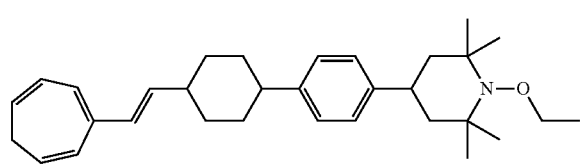

97

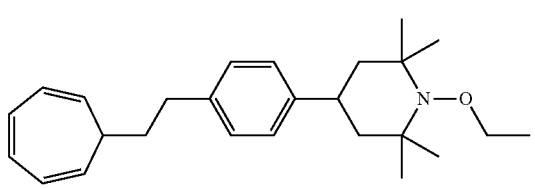

98

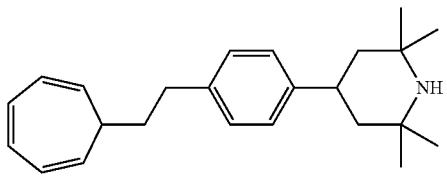

99

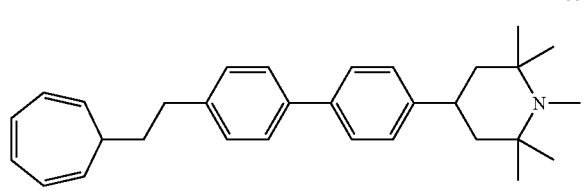

100

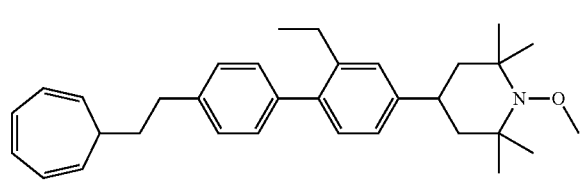

101

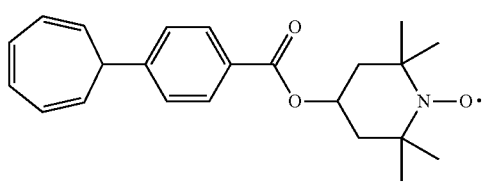

Example 1 and a composition in Use Example 2. The invention also includes a mixture of at least two of the compositions in Use Examples. The compounds in Examples (including Use Examples) were represented by symbols based on the definition of the following Table 4. In Table 4, a configuration of 1,4-cyclohexylene is trans. Parenthesized numbers described after the symbols in Examples represent formulas to which the compounds belong. A symbol (—) means any other liquid crystal compound. A content (percentage) of the liquid crystal compound is a weight percent (% by weight) based on the weight of the liquid crystal composition. Finally, characteristic values of the liquid crystal composition were summarized. Characteristics were measured according to the methods described above, and measured values were described as were (without extrapolation).

TABLE 4

Method for Description of Compounds using Symbols
R—(A$_1$)—Z$_1$— . . . —Z$_n$—(A$_n$)—R'

| 1) Left-terminal Group R— | Symbol |
|---|---|
| FC$_n$H$_{2n}$— | Fn- |
| C$_n$H$_{2n+1}$— | n- |
| C$_n$H$_{2n+1}$O— | nO— |
| C$_m$H$_{2m+1}$OC$_n$H$_{2n}$— | mOn- |
| CH$_2$=CH— | V— |
| C$_n$H$_{2n+1}$—CH=CH— | nV— |
| CH$_2$=CH—C$_n$H$_{2n}$— | Vn- |
| C$_m$H$_{2m+1}$—CH=CH—C$_n$H$_{2n}$— | mVn- |
| CF$_2$=CH— | VFF— |
| CF$_2$=CH—C$_n$H$_{2n}$— | VFFn- |

| 2) Right-terminal Group —R' | Symbol |
|---|---|
| —C$_n$H$_{2n+1}$ | -n |
| —OC$_n$H$_{2n+1}$ | —On |
| —COOCH$_3$ | -EMe |
| —CH=CH$_2$ | —V |
| —CH=CH—C$_n$H$_{2n+1}$ | —Vn |
| —C$_n$H$_{2n}$—CH=CH$_2$ | -nV |
| —C$_m$H$_{2m}$—CH=CH—C$_n$H$_{2n+1}$ | -mVn |
| —CH=CF$_2$ | —VFF |
| —F | —F |
| —Cl | —CL |
| —OCF$_3$ | —OCF3 |
| —OCF$_2$H | —OCF2H |
| —CF$_3$ | —CF3 |
| —C≡N | —C |

| 3) Bonding Group —Z$_n$— | Symbol |
|---|---|
| —C$_n$H$_{2n}$— | n |
| —COO— | E |
| —CH=CH— | V |
| —CH$_2$O— | 1O |
| —OCH$_2$— | O1 |
| —CF$_2$O— | X |
| —C=O— | T |

| 4) Ring Structure —An— | Symbol |
|---|---|
| (cyclohexane ring) | H |
| (benzene ring) | B |

2. Example of a Liquid Crystal Composition

The invention will be described by Use Examples in further detail. The invention is not limited thereby. The invention includes a mixture of a composition in Use TABLE 4-continued Method for Description of Compounds using Symbols
R—(A₁)—Z₁— ... —Zₙ—(Aₙ)—R'

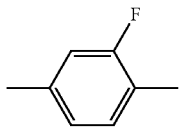 B(F)

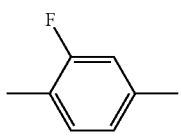 B(2F)

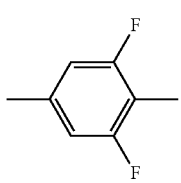 B(F,F)

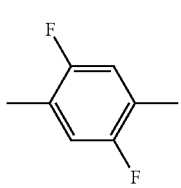 B(2F,5F)

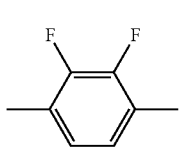 B(2F,3F)

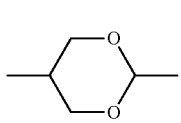 G

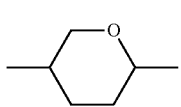 dh

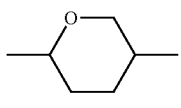 Dh

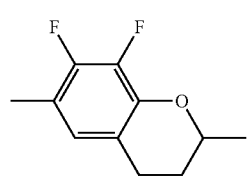 Cro(7F,8F)

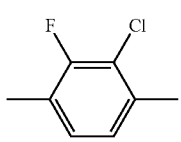 B(2F,3CL)

TABLE 4-continued

Method for Description of Compounds using Symbols
R—(A₁)—Z₁— ... —Zₙ—(Aₙ)—R'

5) Examples of Description

Example 1  3—HB—O2

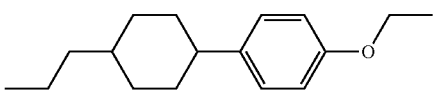

Example 2  3—HBB(F,F)—F

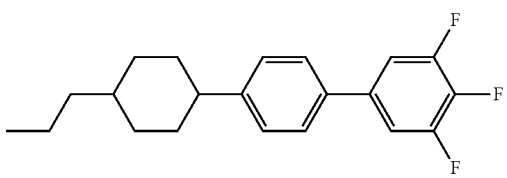 [SMILES: CCCC1CCC(c2ccc(-c3cc(F)c(F)c(F)c3)cc2)CC1]

Use Example 1

| | | |
|---|---|---|
| 2-HB-C | (8-1) | 5% |
| 3-HB-C | (8-1) | 12% |
| 7-HB-1 | (2-5) | 5% |
| 3-HB-O2 | (2-5) | 10% |
| 2-BTB-1 | (2-10) | 3% |
| 3-HHB-F | (6-1) | 4% |
| 3-HHB-1 | (3-1) | 8% |
| 3-HHB-O1 | (3-1) | 5% |
| 3-HHB-3 | (3-1) | 14% |
| 3-HHEB-F | (6-10) | 4% |
| 5-HHEB-F | (6-10) | 4% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 5% |

To the composition described above, compound (No. 1) described below was added at a proportion of 0.05% by weight.

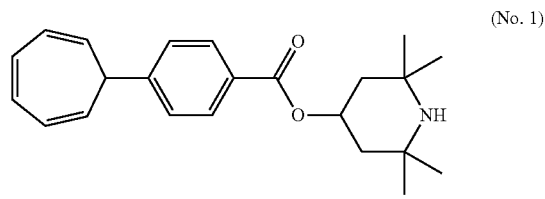 [SMILES: CC1(C)CC(OC(=O)c2ccc(C3C=CC=CC=C3)cc2)CC(C)(C)N1]

(No. 1)

NI=99.3° C.; η=17.8 mPa·s; Δn=0.098; Δ∈=4.5.

Use Example 2

| | | |
|---|---|---|
| 3-HB-CL | (5-2) | 13% |
| 3-HH-4 | (2-1) | 12% |
| 3-HB-O2 | (2-5) | 8% |
| 3-HHB(F,F)-F | (6-3) | 3% |
| 5-HHB(F,F)-F | (6-3) | 5% |
| 3-HBB(F,F)-F | (6-24) | 25% |
| 5-HBB(F,F)-F | (6-24) | 24% |
| 5-HBB(F)-2 | (4-5) | 5% |
| 5-HBB(F)-3 | (4-5) | 5% |

To the composition described above, compound (No. 11) described below was added at a proportion of 0.07% by weight.

(No. 11)

NI=71.8° C.; η=18.9 mPa·s; Δn=0.114; Δ∈=5.3.

Use Example 3

| 3-HB-O2 | (2-5) | 7% |
|---|---|---|
| 7-HB(F,F)-F | (5-4) | 3% |
| 3-HBB-F | (6-22) | 3% |
| 2-HHB(F)-F | (6-2) | 10% |
| 3-HHB(F)-F | (6-2) | 10% |
| 5-HHB(F)-F | (6-2) | 10% |
| 2-HBB(F)-F | (6-23) | 9% |
| 3-HBB(F)-F | (6-23) | 9% |
| 5-HBB(F)-F | (6-23) | 13% |
| 2-HBB-F | (6-22) | 4% |
| 3-HBB-F | (6-22) | 4% |
| 5-HBB-F | (6-22) | 3% |
| 3-HBB(F,F)-F | (6-24) | 5% |
| 5-HBB(F,F)-F | (6-24) | 10% |

To the composition described above, compound (No. 12) descried below was added at a proportion of 0.08% by weight.

(No. 12)

NI=86.2° C.; η=24.6 mPa·s; Δn=0.116; Δ∈=5.7.

Use Example 4

| 3-HB-CL | (5-2) | 5% |
|---|---|---|
| 5-HB-CL | (5-2) | 11% |
| 3-HH-4 | (2-1) | 12% |
| 3-HH-5 | (2-1) | 4% |
| 3-HHB-F | (6-1) | 4% |
| 3-HHB-CL | (6-1) | 3% |
| 4-HHB-CL | (6-1) | 4% |
| 3-HHB(F)-F | (6-2) | 10% |
| 4-HHB(F)-F | (6-2) | 9% |
| 5-HHB(F)-F | (6-2) | 9% |
| 7-HHB(F)-F | (6-2) | 8% |
| 5-HBB(F)-F | (6-23) | 4% |
| 1O1-HBBH(F,F)-5 | (4-1) | 3% |
| 3-HHBB(F,F)-F | (7-6) | 2% |
| 4-HHBB(F,F)-F | (7-6) | 3% |
| 5-HHBB(F,F)-F | (7-6) | 3% |
| 3-HH2BB(F,F)-F | (7-15) | 3% |
| 4-HH2BB(F,F)-F | (7-15) | 3% |

To the composition described above, compound (No. 14) described below was added at a proportion of 0.05% by weight.

(No. 14)

NI=114.2° C.; η=19.1 mPa·s; Δn=0.091; Δ∈=3.7.

Use Sample 5

| 3-HHB(F,F)-F | (6-3) | 9% |
|---|---|---|
| 5-HHB(F,F)-F | (6-3) | 5% |
| 3-H2HB(F,F)-F | (6-15) | 8% |
| 4-H2HB(F,F)-F | (6-15) | 8% |
| 5-H2HB(F,F)-F | (6-15) | 8% |
| 3-HBB(F,F)-F | (6-24) | 21% |
| 5-HBB(F,F)-F | (6-24) | 15% |
| 3-H2BB(F,F)-F | (6-27) | 10% |
| 5-HHBB(F,F)-F | (7-6) | 3% |
| 5-HHEBB-F | (7-17) | 2% |
| 3-HH2BB(F,F)-F | (7-15) | 3% |
| 1O1-HBBH-4 | (4-1) | 4% |
| 1O1-HBBH-5 | (4-1) | 4% |

To the composition described above, compound (No. 1) described below was added at a proportion of 0.08% by weight.

(No. 1)

NI=98.8° C.; η=34.6 mPa·s; Δn=0.114; Δ∈=8.9.

A pitch when compound (Op-05) was added to the composition described above at a proportion of 0.25% by weight was 66.4 μm.

Use Example 6

| 5-HB-F | (5-2) | 12% |
|---|---|---|
| 6-HB-F | (5-2) | 9% |
| 7-HB-F | (5-2) | 7% |
| 2-HHB-OCF3 | (6-1) | 7% |
| 3-HHB-OCF3 | (6-1) | 7% |
| 4-HHB-OCF3 | (6-1) | 7% |
| 5-HHB-OCF3 | (6-1) | 5% |
| 5-HH2B-OCF3 | (6-4) | 4% |
| 3-HHB(F,F)-OCF2H | (6-3) | 4% |
| 3-HHB(F,F)-OCF3 | (6-3) | 5% |
| 3-HHB(F,F)-F | (6-3) | 4% |
| 3-HH2B(F)-F | (6-5) | 3% |
| 3-HBB(F)-F | (6-23) | 10% |
| 5-HBB(F)-F | (6-23) | 10% |
| 5-HBBH-3 | (4-1) | 3% |
| 3-HB(F)BH-3 | (4-2) | 3% |

To the composition described above, compound (No. 11) described below was added at a proportion of 0.01% by weight.

(No. 11)

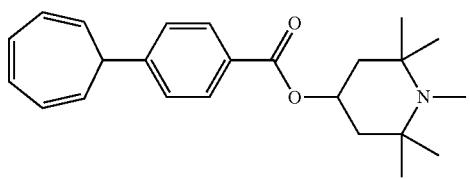

NI=83.8° C.; η=15.5 mPa·s; Δn=0.091; Δ∈=4.7.

Use Example 7

| 5-HB-CL | (5-2) | 11% |
| 3-HH-4 | (2-1) | 8% |
| 3-HHB-1 | (3-1) | 5% |
| 3-HHB(F,F)-F | (6-3) | 8% |
| 3-H2HB(F,F)-F | (6-15) | 5% |
| 3-HBB(F,F)-F | (6-24) | 15% |
| 5-HBB(F,F)-F | (6-24) | 15% |
| 3-HHEB(F,F)-F | (6-12) | 10% |
| 4-HHEB(F,F)-F | (6-12) | 3% |
| 5-HHEB(F,F)-F | (6-12) | 3% |
| 2-HBEB(F,F)-F | (6-39) | 3% |
| 3-HBEB(F,F)-F | (6-39) | 5% |
| 5-HBEB(F,F)-F | (6-39) | 3% |
| 3-HHBB(F,F)-F | (7-6) | 6% |

To the composition described above, compound (No. 12) described below was added at a proportion of 0.04% by weight.

(No. 12)

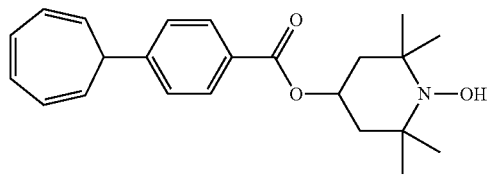

NI=80.9° C.; η=22.2 mPa·s; Δn=0.100; Δ∈=8.6.

Use Example 8

| 3-HB-CL | (5-2) | 6% |
| 5-HB-CL | (5-2) | 4% |
| 3-HHB-OCF3 | (6-1) | 5% |
| 3-H2HB-OCF3 | (6-13) | 5% |
| 5-H4HB-OCF3 | (6-19) | 15% |
| V-HHB(F)-F | (6-2) | 5% |
| 3-HHB(F)-F | (6-2) | 5% |
| 5-HHB(F)-F | (6-2) | 5% |
| 3-H4HB(F,F)-CF3 | (6-21) | 8% |
| 5-H4HB(F,F)-CF3 | (6-21) | 10% |
| 3-HHB(F,F)-F | (6-3) | 3% |
| 5-H2HB(F,F)-F | (6-15) | 5% |
| 5-H4HB(F,F)-F | (6-21) | 7% |
| 2-H2BB(F)-F | (6-26) | 5% |
| 3-H2BB(F)-F | (6-26) | 7% |
| 3-HBEB(F,F)-F | (6-39) | 5% |

To the composition described above, compound (No. 14) described below was added at a proportion of 0.03% by weight.

(No. 14)

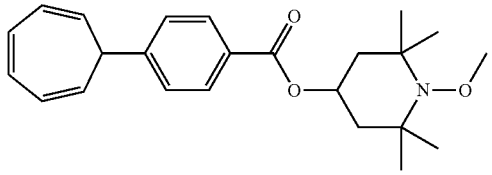

NI=67.3° C.; η=24.4 mPa·s; Δn=0.093; Δ∈=8.1.

Use Example 9

| 3-HB-CL | (5-2) | 5% |
| 5-HB-CL | (5-2) | 12% |
| 7-HB(F,F)-F | (5-4) | 3% |
| 3-HH-4 | (2-1) | 10% |
| 3-HH-5 | (2-1) | 5% |
| 3-HB-O2 | (2-5) | 15% |
| 3-HHB-1 | (3-1) | 8% |
| 3-HHB-O1 | (3-1) | 5% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 6% |
| 3-H2HB(F,F)-F | (6-15) | 5% |
| 4-H2HB(F,F)-F | (6-15) | 5% |

To the composition described above, compound (No. 1) described below was added at a proportion of 0.03% by weight.

(No. 1)

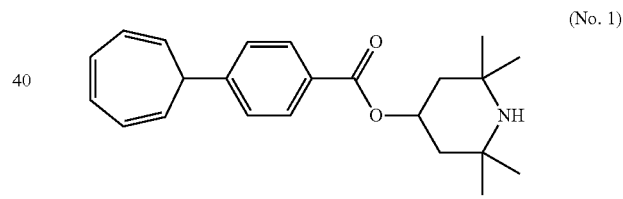

NI=70.2° C.; η=13.2 mPa·s; Δn=0.074; Δ∈=2.7.

Use Example 10

| V2-BB-1 | (2-8) | 5% |
| 5-HB-CL | (5-2) | 3% |
| 7-HB(F)-F | (5-3) | 7% |
| 3-HH-4 | (2-1) | 9% |
| 3-HH-5 | (2-1) | 10% |
| 3-HB-O2 | (2-5) | 8% |
| 3-HHEB-F | (6-10) | 8% |
| 5-HHEB-F | (6-10) | 8% |
| 3-HHEB(F,F)-F | (6-12) | 10% |
| 4-HHEB(F,F)-F | (6-12) | 5% |
| 3-GHB(F,F)-F | (6-109) | 5% |
| 4-GHB(F,F)-F | (6-109) | 6% |
| 5-GHB(F,F)-F | (6-109) | 7% |
| 2-HHB(F)-F | (6-3) | 4% |
| 3-HHB(F,F)-F | (6-3) | 5% |

To the composition described above, compound (No. 11) described below was added at a proportion of 0.05% by weight.

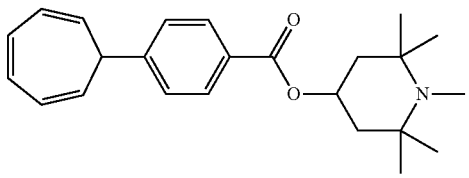
(No. 11)

NI=70.2° C.; η=18.1 mPa·s; Δn=0.071; Δ∈=6.0.

Use Example 11

| 1V2-BEB(F,F)-C | (8-15) | 6% |
| --- | --- | --- |
| 3-HB-C | (8-1) | 18% |
| 2-BTB-1 | (2-10) | 10% |
| 3-HH-V | (2-1) | 10% |
| 5-HH-VFF | (2-1) | 20% |
| 3-HHB-1 | (3-1) | 4% |
| VFF-HHB-1 | (3-1) | 8% |
| VFF2-HHB-1 | (3-1) | 11% |
| 3-H2BTB-2 | (3-17) | 5% |
| 3-H2BTB-3 | (3-17) | 4% |
| 3-H2BTB-4 | (3-17) | 4% |

To the composition described above, compound (No. 12) described below was added at a proportion of 0.06% by weight.

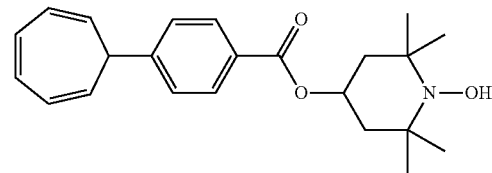
(No. 12)

NI=81.4° C.; η=10.4 mPa·s; Δn=0.129; Δ∈=6.7.

INDUSTRIAL APPLICABILITY

A compound according to the invention is useful as a light stabilizer. A liquid crystal composition containing the compound can be widely applied to a liquid crystal display device used for a personal computer, a television and so forth.

What is claimed is:

1. A compound represented by formula (1):

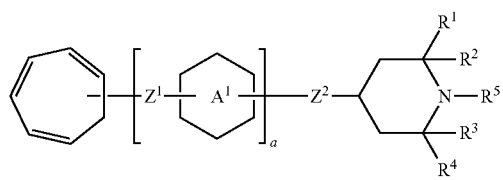
(1)

wherein, in formula (1),

R$^1$, R$^2$, R$^3$ and R$^4$ are independently hydrogen or alkyl having 1 to 4 carbons, and R$^5$ is hydrogen, hydroxy, oxy radical, alkyl having 1 to 10 carbons or alkoxy having 1 to 10 carbons;

ring A$^1$ is 1,4-cyclohexylene, 1,4-cyclohexenylene, 3,4-dihydro-2H-pyrane-2,5-diyl, 3,4-dihydro-2H-pyrane-3,6-diyl, 3,6-dihydro-2H-pyrane-2,5-diyl, tetrahydropyran-2,5-diyl, 1,3-dioxane-2,5-diyl, 1,2-phenylene, 1,3-phenylene, 1,4-phenylene, pyridine-2,5-diyl, pyrimidine-2,5-diyl, decahydronaphthalene-2,6-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl or naphthalene-2,7-diyl, and in the rings, at least one hydrogen may be replaced by fluorine, chlorine, alkyl having 1 to 5 carbons, alkoxy having 1 to 5 carbons, or alkyl having 1 to 5 carbons in which at least one hydrogen is replaced by fluorine or chlorine, and one hydrogen may be replaced by a monovalent group represented by formula (P-1);

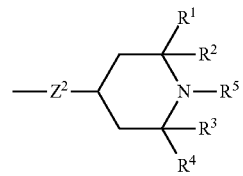
(P-1)

wherein, in formula (P-1),

R$^1$, R$^2$, R$^3$ and R$^4$ are independently hydrogen or alkyl having 1 to 4 carbons, and R$^5$ is hydrogen, hydroxy, oxy radical, alkyl having 1 to 10 carbons or alkoxy having 1 to 10 carbons;

Z$^2$ is a single bond or alkylene having 1 to 10 carbons, and in the alkylene, at least one —CH$_2$— may be replaced by —O—, —S—, —CO—, —COO— or —OCO—, and at least one —CH$_2$—CH$_2$— may be replaced by —CH=CH— or —C≡C—, and in the groups, at least one hydrogen may be replaced by fluorine or chlorine; and in formula (1), Z$^1$ and Z$^2$ are independently a single bond or alkylene having 1 to 10 carbons, and in the alkylene, at least one —CH$_2$— may be replaced by —O—, —S—, —CO—, —COO— or —OCO—, and at least one —CH$_2$—CH$_2$— may be replaced by —CH=CH— or —C≡C—, and in the groups, at least one hydrogen may be replaced by fluorine or chlorine; and a is 0, 1, 2 or 3.

2. The compound according to claim 1, wherein, in formula (1),

R$^1$, R$^2$, R$^3$ and R$^4$ are independently hydrogen or alkyl having 1 to 4 carbons, and R$^5$ is hydrogen, hydroxy, oxy radical, alkyl having 1 to 10 carbons or alkoxy having 1 to 10 carbons;

ring A$^1$ is 1,4-cyclohexylene, 1,4-cyclohexenylene, 3,4-dihydro-2H-pyrane-2,5-diyl, 3,4-dihydro-2H-pyrane-3,6-diyl, 3,6-dihydro-2H-pyrane-2,5-diyl, tetrahydropyran-2,5-diyl, 1,3-dioxane-2,5-diyl, 1,2-phenylene, 1,3-phenylene, 1,4-phenylene, pyridine-2,5-diyl, pyrimidine-2,5-diyl, decahydronaphthalene-2,6-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl or naphthalene-2,7-diyl, and in the rings, at least one hydrogen may be replaced by fluorine, chlorine, alkyl having 1 to 5 carbons, alkoxy having 1 to 5 carbons, or alkyl having 1 to 5 carbons in which at least one hydrogen is replaced by fluorine or chlorine;

$Z^1$ and $Z^2$ are independently a single bond or alkylene 1 to 10 carbons, and in the alkylene, at least one —$CH_2$— may be replaced by —O—, —S—, —CO—, —COO— or —OCO—, and at least one —$CH_2$—$CH_2$— may be replaced by —CH=CH— or —C≡C—, and in the groups, at least one hydrogen may be replaced by fluorine or chlorine; and a is 0, 1, 2 or 3.

3. The compound according to claim 1, wherein, in formula (1), $R^1$, $R^2$, $R^3$ and $R^4$ are independently hydrogen or alkyl having 1 to 4 carbons, and $R^5$ is hydrogen, hydroxy, oxy radical, alkyl having 1 to 10 carbons or alkoxy having 1 to 10 carbons;

ring $A^1$ is 1,4-cyclohexylene, 1,4-cyclohexenylene, tetrahydropyran-2,5-diyl, 1,3-dioxane-2,5-diyl, 1,2-phenylene, 1,3-phenylene, 1,4-phenylene, pyrimidine-2,5-diyl or pyridine-2,5-diyl, and in the rings, at least one hydrogen may be replaced by fluorine, chlorine, alkyl having 1 to 5 carbons, alkoxy having 1 to 5 carbons, or alkyl having 1 to 5 carbons in which at least one hydrogen is replaced by fluorine or chlorine;

$Z^1$ and $Z^2$ are independently a single bond or alkylene having 1 to 10 carbons, and in the alkylene, at least one —$CH_2$— may be replaced by —O—, —S—, —CO—, —COO— or —OCO—, and at least one —$CH_2$—$CH_2$— may be replaced by —CH=CH— or —C≡C—, and in the groups, at least one hydrogen may be replaced by fluorine or chlorine; and a is 1, 2 or 3.

4. The compound according to claim 1, wherein, in formula (1), $R^1$, $R^2$, $R^3$ and $R^4$ are independently hydrogen or alkyl having 1 to 4 carbons, and $R^5$ is hydrogen, hydroxy, oxy radical, alkyl having 1 to 10 carbons or alkoxy having 1 to 10 carbons;

ring $A^1$ is 1,4-cyclohexylene, 1,4-cyclohexenylene 1,2-phenylene, 1,3-phenylene or 1,4-phenylene, and the rings, at least one hydrogen may be replaced by fluorine, chlorine, alkyl having 1 to 5 carbons, alkoxy having 1 to 5 carbons, or alkyl having 1 to 5 carbons in which at least one hydrogen is replaced by fluorine or chlorine;

$Z^1$ and $Z^2$ are independently a single bond or alkylene having 1 to 10 carbons, and in the alkylene, at least one —$CH_2$— may be replaced by —O—, —CO—, —COO— or —OCO—, and at least one —$CH_2$—$CH_2$— may be replaced by —CH=CH—, and in the groups, at least one hydrogen may be replaced by fluorine or chlorine; and a is 1, 2 or 3.

5. The compound according to claim 1, represented by formula (1a), formula (1b) or formula (1c):

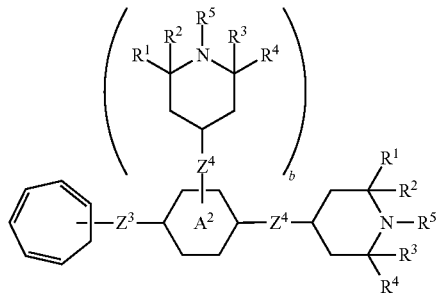

(1a)

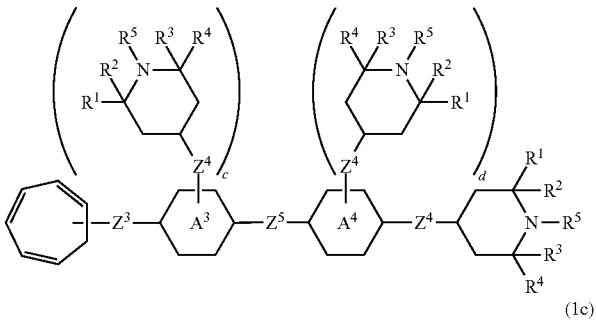

(1b)

(1c)

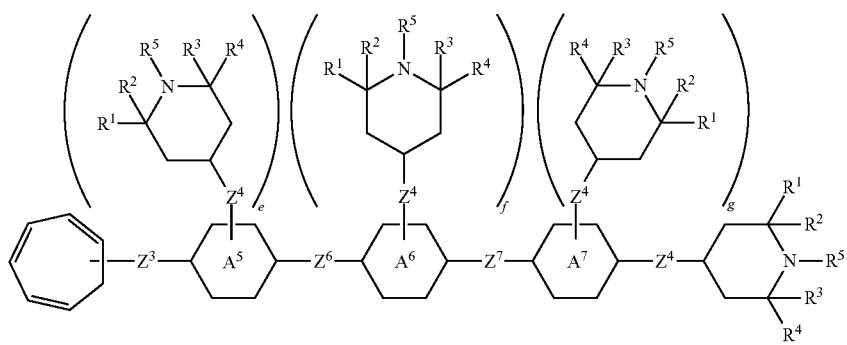

wherein, in formula (1a), formula (1b) or formula (1c), $R^1$, $R^2$, $R^3$ and $R^4$ are independently hydrogen or alkyl having 1 to 4 carbons, and $R^5$ is hydrogen, hydroxy, oxy radical, alkyl having 1 to 10 carbons or alkoxy having 1 to 10 carbons;

ring $A^2$, ring $A^3$, ring $A^4$, ring $A^5$, ring $A^6$ and ring $A^7$ are independently 1,4-cyclohexylene, 1,4-cyclohexenylene or 1,4-phenylene, and in the rings, at least one hydrogen may be replaced by fluorine or chlorine;

$Z^3$, $Z^4$, $Z^5$, $Z^6$ and $Z^7$ are independently a single bond or alkylene having 1 to 10 carbons, and in the alkylene, at least one —$CH_2$— may be replaced by —O—, —CO—, —COO— or —OCO—, and at least one —$CH_2$—$CH_2$— may be replaced by —CH=CH—, and in the groups, at least one hydrogen may be replaced by fluorine or chlorine; and b, c, d, e, f and g are 0 or 1, a sum of c and d is 0 or 1, and a sum of e, f and g is 0 or 1.

6. The compound according to claim 1, represented by formula (1d), formula (1e) or formula (1f):

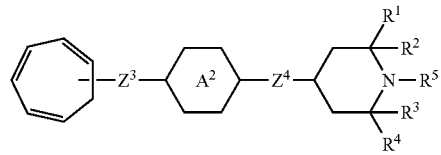
(1d)

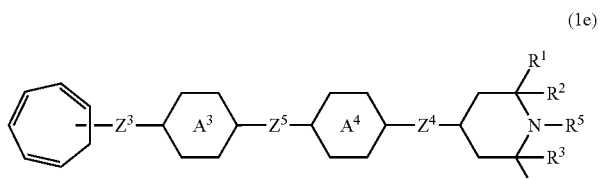
(1e)

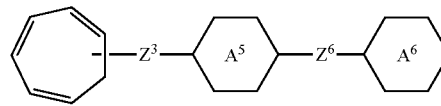
(1f)

wherein, in formula (1d), formula (1e) or formula (1f),
R$^1$, R$^2$, R$^3$ and R$^4$ are independently hydrogen or alkyl having 1 to 4 carbons, and R$^5$ is hydrogen, hydroxy, oxy radical, alkyl having 1 to 10 carbons or alkoxy having 1 to 10 carbons;
ring A$^2$, ring A$^3$, ring A$^4$, ring A$^5$, ring A$^6$ and ring A$^7$ are independently 1,4-cyclohexylene, 1,4-cyclohexenylene or 1,4-phenylene, and in the rings, at least one hydrogen may be replaced by fluorine; and
Z$^3$, Z$^4$, Z$^5$, Z$^6$ and Z$^7$ are independently a single bond, —COO—, —OCO—, —CH$_2$O—, —OCH$_2$—, —CF$_2$O—, —OCF$_2$—, —CH$_2$CH$_2$— or —CH=CH—.

7. The compound according to claim 6, wherein, in formula (1d), formula (1e) or formula (1f),
R$^1$, R$^2$, R$^3$ and R$^4$ are independently hydrogen or alkyl having 1 to 4 carbons, and R$^5$ is hydrogen, hydroxy, oxy radical, alkyl having 1 to 10 carbons or alkoxy having 1 to 10 carbons;
ring A$^2$, ring A$^3$, ring A$^4$, ring A$^5$, ring A$^6$ and ring A$^7$ are independently 1,4-phenylene or 1,4-phenylene in which at least one hydrogen is replaced by fluorine; and
Z$^3$, Z$^5$, Z$^6$ and Z$^7$ are independently a single bond, —COO—, —OCO—, —CH$_2$O—, —OCH$_2$— or —CH$_2$CH$_2$—, and Z$_4$ is —COO—.

8. The compound according to claim 1, represented by formula (1g) or formula (1h):

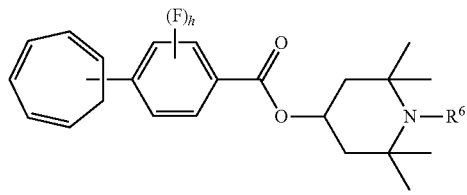
(1g)

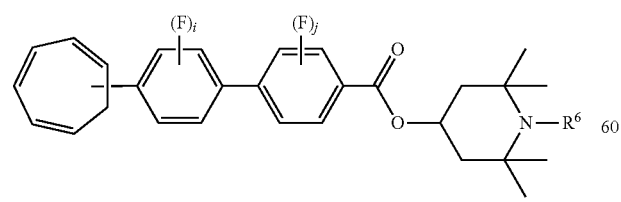
(1h)

wherein, in formula (1g) or formula (1h), R$^6$ is hydrogen, hydroxy, oxy radical, alkyl having 1 to 10 carbons or alkoxy having 1 to 10 carbons; and h, i and j are independently 0, 1 or 2.

9. The compound according to claim 1, represented by formula (1i) or formula (1j):

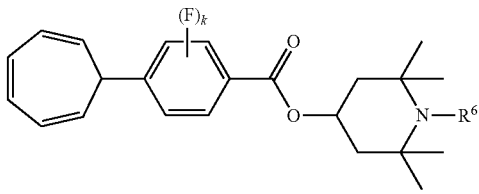
(1i)

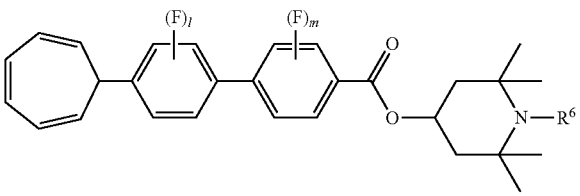
(1j)

wherein, in formula (1i) or formula (1j), R$^6$ is hydrogen, hydroxy, oxy radical, alkyl having 1 to 10 carbons or alkoxy having 1 to 10 carbons; and k, l and m are independently 0, 1 or 2.

10. The compound according to claim 1, represented by formula (1k):

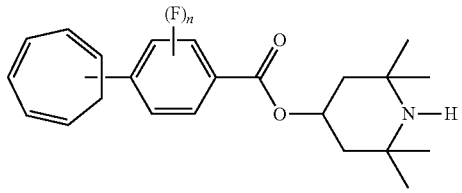
(1k)

wherein, in formula (1k), n is 0, 1 or 2.

11. The compound according to claim 1, represented by formula (1l):

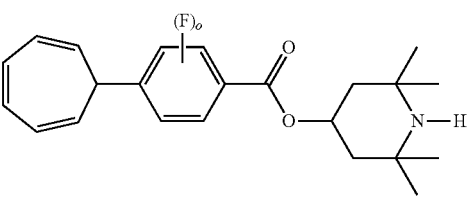
(1l)

wherein, in formula (1l), o is 0, 1 or 2.

12. A liquid crystal composition, containing at least one compound according to claim 1.

13. The liquid crystal composition according to claim 12, further containing at least one compound selected from the group of compounds represented by formula (2) to formula (4):

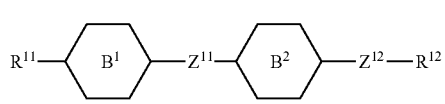
(2)

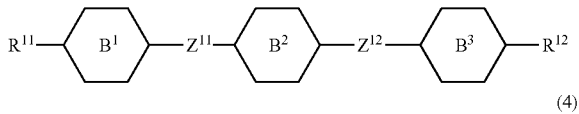
(3)

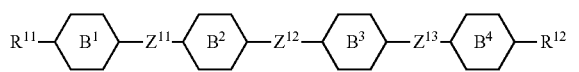
(4)

wherein, in formula (2) to formula (4),
R$^{11}$ and R$^{12}$ are independently alkyl having 1 to 10 carbons or alkenyl having 2 to 10 carbons, and in the alkyl or the alkenyl, at least one —CH$_2$— may be replaced by —O—, and at least one hydrogen may be replaced by fluorine;
ring B$^1$, ring B$^2$, ring B$^3$ and ring B$^4$ are independently 1,4-cyclohexylene, 1,4-phenylene, 2-fluoro-1,4-phenylene, 2,5-difluoro-1,4-phenylene or pyrimidine-2,5-diyl; and
Z$^{11}$, Z$^{12}$ and Z$^{13}$ are independently a single bond, —CH$_2$CH$_2$—, —CH=CH—, —C≡C— or —COO—.

14. The liquid crystal composition according to claim 12, further containing at least one compound selected from the group of compounds represented by formula (5) to formula (7):

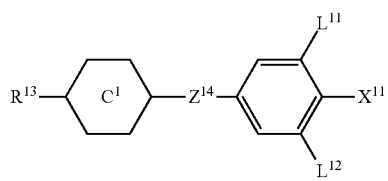
(5)

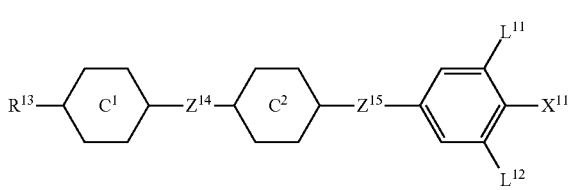
(6)

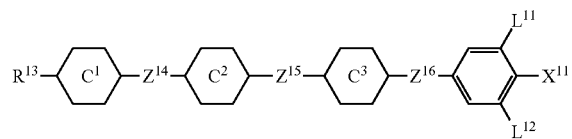
(7)

wherein, in formula (5) to formula (7),
R$^{13}$ is alkyl having 1 to 10 carbons or alkenyl having 2 to 10 carbons, and in the alkyl and the alkenyl, at least one —CH$_2$— may be replaced by —O—, and at least one hydrogen may be replaced by fluorine;
X$^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;
ring C$^1$, ring C$^2$ and ring C$^3$ are independently 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;
Z$^{14}$, Z$^{15}$ and Z$^{16}$ are independently a single bond, —CH$_2$CH$_2$—, —CH=CH—, —C≡C—, —COO—, —CF$_2$O—, —OCF$_2$—, —CH$_2$O— or —(CH$_2$)$_4$—; and
L$^{11}$ and L$^{12}$ are independently hydrogen or fluorine.

15. The liquid crystal composition according to claim 12, further containing at least one compound selected from the group of compounds represented by formula (8):

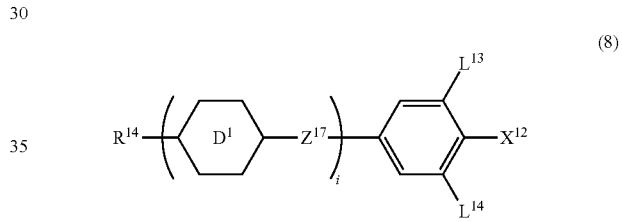
(8)

wherein, in formula (8),
R$^{14}$ is alkyl having 1 to 10 carbons or alkenyl having 2 to 10 carbons, and in the alkyl and the alkenyl, at least one —CH$_2$— may be replaced by —O—, and at least one hydrogen may be replaced by fluorine; X$^{12}$ is —C≡N or —C≡C—C≡N;
ring D$^1$ is 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;
Z$^{17}$ is a single bond, —CH$_2$CH$_2$—, —C≡C—, —COO—, —CF$_2$O—, —OCF$_2$— or —CH$_2$O—;
L$^{13}$ and L$^{14}$ are independently hydrogen or fluorine; and
i is 1, 2, 3 or 4.

16. The liquid crystal composition according to claim 12, further containing at least one compound selected from the group of compounds represented by formula (9) to formula (15):

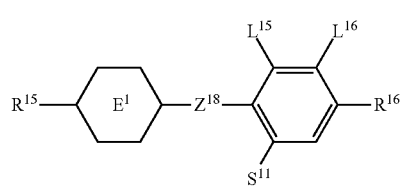
(9)

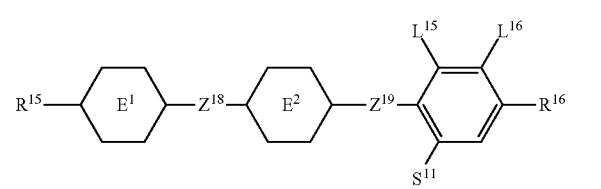
(10)

-continued

(11)
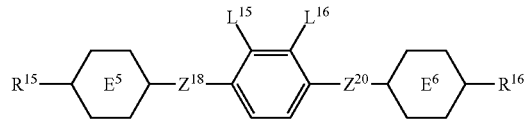

(12)
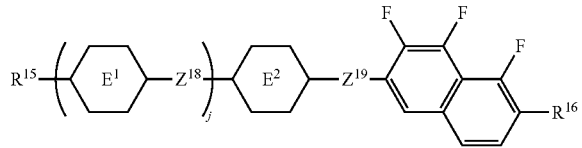

(13)
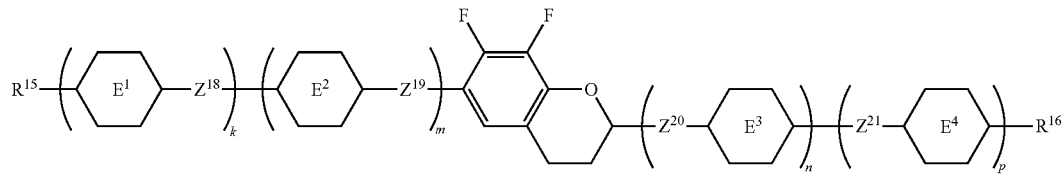

(14)
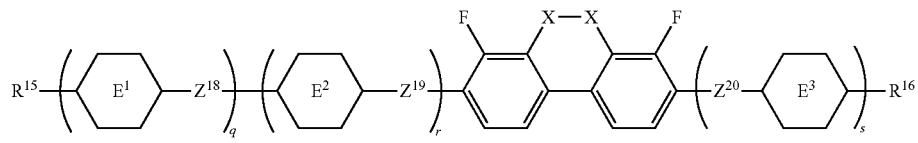

(15)
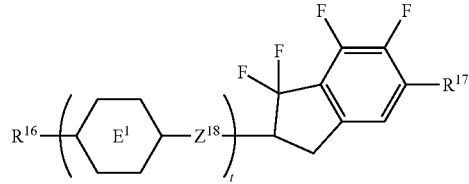

wherein, in formula (9) to formula (15), $R^{15}$ and $R^{16}$ are independently alkyl having 1 to 10 carbons or alkenyl having 2 to 10 carbons, and in the alkyl and the alkenyl, at least one —CH$_2$— may be replaced by —O—, and at least one hydrogen may be replaced by fluorine;

$R^{17}$ is hydrogen, fluorine, alkyl having 1 to 10 carbons or alkenyl having 2 to 10 carbons, and in the alkyl and the alkenyl, at least one —CH$_2$— may be replaced by —O—, and at least one hydrogen may be replaced by fluorine;

ring $E^1$, ring $E^2$, ring $E^3$ and ring $E^4$ are independently 1,4-cyclohexylene, 1,4-cyclohexenylene, 1,4-phenylene in which at least one hydrogen may be replaced by fluorine, tetrahydropyran-2,5-diyl or decahydronaphthalene-2,6-diyl;

ring $E^5$ and ring $E^6$ are independently 1,4-cyclohexylene, 1,4-cyclohexenylene, 1,4-phenylene, tetrahydropyran-2,5-diyl or decahydronaphthalene-2,6-diyl;

$Z^{18}$, $Z^{19}$, $Z^{20}$ and $Z^{21}$ are independently a single bond, —CH$_2$CH$_2$—, —COO—, —CH$_2$O—, —OCF$_2$— or —OCF$_2$CH$_2$CH$_2$—;

$L^{15}$ and $L^{16}$ are independently fluorine or chlorine;

$S^{11}$ is hydrogen or methyl;

X is —CHF— or —CF$_2$—; and j, k, m, n, p, q, r and s are independently 0 or 1, a sum of k, m, n and p is 1 or 2, a sum of q, r and s is 0, 1, 2 or 3, and t is 1, 2 or 3.

17. A liquid crystal display device, including at least one liquid crystal composition according to claim 12.

* * * * *